(12) United States Patent
Manning et al.

(10) Patent No.: US 12,050,222 B2
(45) Date of Patent: *Jul. 30, 2024

(54) SYSTEMS AND METHODS FOR SAMPLE PREPARATION, DATA GENERATION, AND PROTEIN CORONA ANALYSIS

(71) Applicant: Seer, Inc., Redwood City, CA (US)

(72) Inventors: William Manning, Redwood City, CA (US); Young Kim, Union City, CA (US); Brandon Kwan-Leong, Daly City, CA (US); Hope Liou, Pleasanton, CA (US); Xiaoyan Zhao, Foster City, CA (US); Daniel Hornburg, Foster City, CA (US); Martin Goldberg, Saratoga, CA (US)

(73) Assignee: Seer, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/365,627

(22) Filed: Aug. 4, 2023

(65) Prior Publication Data
US 2023/0384317 A1    Nov. 30, 2023

Related U.S. Application Data

(63) Continuation of application No. 18/178,288, filed on Mar. 3, 2023, which is a continuation of application
(Continued)

(51) Int. Cl.
*G01N 33/68* (2006.01)
*B01L 3/00* (2006.01)
(Continued)

(52) U.S. Cl.
CPC ........ *G01N 33/6848* (2013.01); *B01L 3/5085* (2013.01); *B01L 7/00* (2013.01);
(Continued)

(58) Field of Classification Search
CPC ........ G01N 33/6848; G01N 1/34; G01N 1/44; G01N 33/54326; G01N 33/54346; B01L 3/5085; B01L 7/00
See application file for complete search history.

(56) References Cited

U.S. PATENT DOCUMENTS

| | | |
|---|---|---|
| 4,443,319 A | 4/1984 | Chait et al. |
| 4,444,879 A | 4/1984 | Foster et al. |

(Continued)

FOREIGN PATENT DOCUMENTS

| | | |
|---|---|---|
| CN | 103703143 A | 4/2014 |
| CN | 109070040 A | 12/2018 |

(Continued)

OTHER PUBLICATIONS

Adam et al. Serum Protein Fingerprinting Coupled with a Pattern-matching Algorithm Distinguishes Prostate Cancer from Benign Prostate Hyperplasia and Healthy Men. Cancer Research. 2002;62:3609-3614.

(Continued)

*Primary Examiner* — Brian R Gordon
*Assistant Examiner* — Dwan A Gerido
(74) *Attorney, Agent, or Firm* — Wilson Sonsini Goodrich & Rosati

(57) ABSTRACT

Systems and methods for automated sample preparation and processing of protein corona are described herein, as well as its application in the discovery of advanced diagnostic tools as well as therapeutic agents.

30 Claims, 14 Drawing Sheets

Related U.S. Application Data

No. 17/216,523, filed on Mar. 29, 2021, now Pat. No. 11,630,112, which is a continuation of application No. PCT/US2020/044908, filed on Aug. 4, 2020.

(60) Provisional application No. 62/883,107, filed on Aug. 5, 2019.

(51) Int. Cl.
| | |
|---|---|
| *B01L 7/00* | (2006.01) |
| *G01N 1/34* | (2006.01) |
| *G01N 1/44* | (2006.01) |
| *G01N 33/543* | (2006.01) |
| *B82Y 5/00* | (2011.01) |
| *B82Y 25/00* | (2011.01) |
| *B82Y 30/00* | (2011.01) |
| *B82Y 35/00* | (2011.01) |
| *B82Y 40/00* | (2011.01) |

(52) U.S. Cl.
CPC ............... *G01N 1/34* (2013.01); *G01N 1/44* (2013.01); *G01N 33/54326* (2013.01); *G01N 33/54346* (2013.01); *B01L 2400/043* (2013.01); *B82Y 5/00* (2013.01); *B82Y 25/00* (2013.01); *B82Y 30/00* (2013.01); *B82Y 35/00* (2013.01); *B82Y 40/00* (2013.01)

(56) References Cited

U.S. PATENT DOCUMENTS

| | | |
|---|---|---|
| 4,483,885 A | 11/1984 | Chait et al. |
| 4,863,873 A | 9/1989 | Matson |
| 4,977,320 A | 12/1990 | Chowdhury et al. |
| 5,045,694 A | 9/1991 | Beavis et al. |
| 5,227,471 A | 7/1993 | Wright, Jr. |
| 5,245,186 A | 9/1993 | Chait et al. |
| 5,296,114 A | 3/1994 | Manz |
| 5,314,996 A | 5/1994 | Wright, Jr. |
| 5,358,618 A | 10/1994 | Ewing et al. |
| 5,366,140 A | 11/1994 | Koskenmaki et al. |
| 5,393,975 A | 2/1995 | Hail et al. |
| 5,498,545 A | 3/1996 | Vestal |
| 5,545,304 A | 8/1996 | Smith et al. |
| 5,599,432 A | 2/1997 | Manz et al. |
| 5,624,539 A | 4/1997 | Ewing et al. |
| 5,639,656 A | 6/1997 | Wright, Jr. |
| 5,652,427 A | 7/1997 | Whitehouse et al. |
| 5,788,166 A | 8/1998 | Valaskovic et al. |
| 5,833,861 A | 11/1998 | Afeyan et al. |
| 5,856,671 A | 1/1999 | Henion et al. |
| 5,872,010 A | 2/1999 | Karger et al. |
| 5,900,481 A | 5/1999 | Lough et al. |
| 5,917,184 A | 6/1999 | Carson et al. |
| 5,928,952 A | 7/1999 | Hutchins et al. |
| 5,952,653 A | 9/1999 | Covey et al. |
| 5,958,202 A | 9/1999 | Regnier et al. |
| 5,993,633 A | 11/1999 | Smith et al. |
| 6,017,693 A | 1/2000 | Yates, III et al. |
| 6,025,136 A | 2/2000 | Drmanac |
| 6,033,546 A | 3/2000 | Ramsey |
| 6,068,749 A | 5/2000 | Karger et al. |
| 6,086,243 A | 7/2000 | Paul et al. |
| 6,091,502 A | 7/2000 | Weigl et al. |
| 6,107,628 A | 8/2000 | Smith et al. |
| 6,139,734 A | 10/2000 | Settlage et al. |
| 6,140,468 A | 10/2000 | Vihko |
| 6,157,921 A | 12/2000 | Barnhill |
| 6,159,739 A | 12/2000 | Weigl et al. |
| 6,175,112 B1 | 1/2001 | Karger et al. |
| 6,187,190 B1 | 2/2001 | Smith et al. |
| 6,207,370 B1 | 3/2001 | Little et al. |
| 6,207,954 B1 | 3/2001 | Andrien, Jr. et al. |
| 6,225,047 B1 | 5/2001 | Hutchens et al. |
| 6,231,737 B1 | 5/2001 | Ramsey et al. |
| 6,240,790 B1 | 6/2001 | Swedberg et al. |
| 6,277,641 B1 | 8/2001 | Yager |
| 6,280,589 B1 | 8/2001 | Manz et al. |
| 6,284,113 B1 | 9/2001 | Bjornson et al. |
| 6,284,115 B1 | 9/2001 | Apffel |
| 6,291,183 B1 | 9/2001 | Pirrung et al. |
| 6,306,087 B1 | 10/2001 | Barnhill et al. |
| 6,309,816 B1 | 10/2001 | Zhang et al. |
| 6,318,970 B1 | 11/2001 | Backhouse |
| 6,322,682 B1 | 11/2001 | Arvidsson et al. |
| 6,327,410 B1 | 12/2001 | Walt et al. |
| 6,329,209 B1 | 12/2001 | Wagner et al. |
| 6,342,142 B1 | 1/2002 | Ramsey |
| 6,358,692 B1 | 3/2002 | Jindal et al. |
| 6,361,944 B1 | 3/2002 | Mirkin et al. |
| 6,363,383 B1 | 3/2002 | Kindo et al. |
| 6,368,562 B1 | 4/2002 | Yao |
| 6,375,817 B1 | 4/2002 | Taylor et al. |
| 6,379,791 B1 | 4/2002 | Cernohous et al. |
| 6,379,971 B1 | 4/2002 | Schneider et al. |
| 6,413,780 B1 | 7/2002 | Bach et al. |
| 6,427,141 B1 | 7/2002 | Barnhill |
| 6,558,955 B1 | 5/2003 | Kristal et al. |
| 6,593,298 B2 | 7/2003 | Jackowski et al. |
| 6,599,877 B2 | 7/2003 | Jackowski et al. |
| 6,602,855 B2 | 8/2003 | Jackowski et al. |
| 6,617,308 B2 | 9/2003 | Jackowski et al. |
| 6,620,786 B2 | 9/2003 | Jackowski et al. |
| 6,620,787 B2 | 9/2003 | Jackowski et al. |
| 6,627,606 B2 | 9/2003 | Jackowski et al. |
| 6,627,607 B2 | 9/2003 | Jackowski et al. |
| 6,627,608 B2 | 9/2003 | Jackowski et al. |
| 6,649,419 B1 | 11/2003 | Anderson |
| 6,658,395 B1 | 12/2003 | Barnhill |
| 6,675,104 B2 | 1/2004 | Paulse et al. |
| 6,677,303 B2 | 1/2004 | Jackowski et al. |
| 6,703,366 B2 | 3/2004 | Jackowski et al. |
| 6,714,925 B1 | 3/2004 | Barnhill et al. |
| 6,730,517 B1 | 5/2004 | Koster et al. |
| 6,756,476 B2 | 6/2004 | Jackowski et al. |
| 6,759,010 B2 | 7/2004 | Lewis et al. |
| 6,855,251 B2 | 2/2005 | Moon et al. |
| 6,858,842 B2 | 2/2005 | Moon et al. |
| 6,863,790 B1 | 3/2005 | Moini et al. |
| 6,942,968 B1 | 9/2005 | Dickinson et al. |
| 6,969,615 B2 | 11/2005 | Knezevic et al. |
| 7,007,710 B2 | 3/2006 | Heller et al. |
| 7,105,812 B2 | 9/2006 | Zhao et al. |
| 7,375,234 B2 | 5/2008 | Sharpless et al. |
| 7,425,700 B2 | 9/2008 | Stults et al. |
| 7,442,921 B2 | 10/2008 | Franzen |
| 7,460,960 B2 | 12/2008 | Lee et al. |
| 7,749,299 B2 | 7/2010 | Vanheusden et al. |
| 8,021,891 B2 | 9/2011 | Rotello et al. |
| 8,795,960 B2 | 8/2014 | Seul et al. |
| 8,906,608 B2 | 12/2014 | Boschetti et al. |
| 9,005,994 B2 | 4/2015 | Huo |
| 9,234,895 B2 | 1/2016 | Hood et al. |
| 9,549,901 B2 | 1/2017 | Shi et al. |
| 9,689,039 B2 | 6/2017 | Wong et al. |
| 9,758,811 B2 | 9/2017 | Brown et al. |
| 10,022,334 B2 | 7/2018 | Farokhzad et al. |
| 10,525,013 B2 | 1/2020 | Farokhzad et al. |
| 10,866,242 B2 | 12/2020 | Farokhzad et al. |
| 11,408,898 B2 | 8/2022 | Farokhzad et al. |
| 11,428,688 B2 | 8/2022 | Xia et al. |
| 11,435,360 B2 | 9/2022 | Farokhzad et al. |
| 11,567,086 B2 | 1/2023 | Farokhzad et al. |
| 11,630,112 B2 * | 4/2023 | Manning .......... G01N 33/54326 422/502 |
| 11,850,309 B2 | 12/2023 | Farokhzad et al. |
| 11,906,526 B2 | 2/2024 | Manning et al. |
| 2001/0014461 A1 | 8/2001 | Hutchens et al. |
| 2001/0041357 A1 | 11/2001 | Fouillet et al. |
| 2001/0044104 A1 | 11/2001 | Warrington et al. |
| 2002/0009394 A1 | 1/2002 | Koster et al. |
| 2002/0010552 A1 | 1/2002 | Rienhoff et al. |
| 2002/0036140 A1 | 3/2002 | Manz et al. |

(56) References Cited

U.S. PATENT DOCUMENTS

| | | |
|---|---|---|
| 2002/0039747 A1 | 4/2002 | Lubman et al. |
| 2002/0041827 A1 | 4/2002 | Yager et al. |
| 2002/0048777 A1 | 4/2002 | Ali et al. |
| 2002/0054289 A1 | 5/2002 | Thibault et al. |
| 2002/0094533 A1 | 7/2002 | Hess et al. |
| 2002/0095260 A1 | 7/2002 | Huyn |
| 2002/0102578 A1* | 8/2002 | Dickinson .......... G01N 21/6452 435/287.2 |
| 2002/0119490 A1 | 8/2002 | Aebersold et al. |
| 2002/0127237 A1 | 9/2002 | Salceda et al. |
| 2002/0127727 A1 | 9/2002 | Bach et al. |
| 2002/0137086 A1 | 9/2002 | Olek et al. |
| 2002/0142481 A1 | 10/2002 | Andersson et al. |
| 2002/0177140 A1 | 11/2002 | Salceda et al. |
| 2002/0193950 A1 | 12/2002 | Gavin et al. |
| 2003/0004402 A1 | 1/2003 | Hitt et al. |
| 2003/0013120 A1 | 1/2003 | Patz et al. |
| 2003/0032043 A1 | 2/2003 | Pohl et al. |
| 2003/0039983 A1 | 2/2003 | Sun et al. |
| 2003/0064377 A1 | 4/2003 | Sun et al. |
| 2003/0077611 A1 | 4/2003 | Slepnev |
| 2003/0078739 A1 | 4/2003 | Norton et al. |
| 2003/0089605 A1 | 5/2003 | Timperman |
| 2003/0111596 A1 | 6/2003 | Becker et al. |
| 2003/0129760 A1 | 7/2003 | Aguilera et al. |
| 2003/0132114 A1 | 7/2003 | Mischak et al. |
| 2003/0134304 A1 | 7/2003 | Van Der Greef et al. |
| 2003/0148295 A1 | 8/2003 | Wan et al. |
| 2003/0148922 A1 | 8/2003 | Knapp et al. |
| 2003/0153007 A1 | 8/2003 | Chen et al. |
| 2003/0175707 A1 | 9/2003 | Sun et al. |
| 2003/0194739 A1 | 10/2003 | Ali et al. |
| 2003/0199001 A1 | 10/2003 | Pitt et al. |
| 2003/0224531 A1 | 12/2003 | Brennen et al. |
| 2003/0228639 A1 | 12/2003 | Wright et al. |
| 2004/0005634 A1 | 1/2004 | Patz, Jr. et al. |
| 2004/0018519 A1 | 1/2004 | Wright, Jr. |
| 2004/0029194 A1 | 2/2004 | Parish et al. |
| 2004/0033591 A1 | 2/2004 | Lubman et al. |
| 2004/0043436 A1 | 3/2004 | Vlahou et al. |
| 2004/0053333 A1 | 3/2004 | Hitt et al. |
| 2004/0075050 A1 | 4/2004 | Rossier et al. |
| 2004/0106131 A1 | 6/2004 | Roy et al. |
| 2004/0132122 A1 | 7/2004 | Banerjee et al. |
| 2004/0147040 A1 | 7/2004 | Bluggel et al. |
| 2004/0153249 A1 | 8/2004 | Zhang et al. |
| 2005/0059013 A1 | 3/2005 | Chan et al. |
| 2005/0072915 A1 | 4/2005 | Stults et al. |
| 2005/0130240 A1 | 6/2005 | Lin et al. |
| 2005/0181513 A1 | 8/2005 | Lopez-Avila et al. |
| 2005/0244973 A1 | 11/2005 | Andel, III et al. |
| 2005/0272049 A1 | 12/2005 | Banerjee et al. |
| 2006/0081539 A1 | 4/2006 | Safar et al. |
| 2006/0186048 A1 | 8/2006 | Tan |
| 2006/0186049 A1 | 8/2006 | Boyes et al. |
| 2007/0009970 A1 | 1/2007 | Heller et al. |
| 2007/0072250 A1 | 3/2007 | Kim et al. |
| 2007/0178504 A1 | 8/2007 | Colpitts et al. |
| 2007/0184456 A1 | 8/2007 | Chee et al. |
| 2007/0224644 A1 | 9/2007 | Liotta et al. |
| 2008/0160546 A1 | 7/2008 | Colpitts et al. |
| 2008/0277578 A1 | 11/2008 | Ferrari et al. |
| 2009/0004687 A1 | 1/2009 | Mansfield et al. |
| 2009/0054222 A1 | 2/2009 | Zhang et al. |
| 2009/0090855 A1 | 4/2009 | Kobold et al. |
| 2009/0253181 A1 | 10/2009 | Vangbo et al. |
| 2009/0291454 A1 | 11/2009 | Sim et al. |
| 2009/0298710 A1 | 12/2009 | Farokhzad et al. |
| 2009/0305392 A1 | 12/2009 | Alfredsson et al. |
| 2010/0267108 A1 | 10/2010 | Jordaan et al. |
| 2010/0285490 A1 | 11/2010 | Dees et al. |
| 2011/0027894 A1 | 2/2011 | Farias-Eisner et al. |
| 2011/0076735 A1 | 3/2011 | Jovanovich et al. |
| 2011/0111443 A1 | 5/2011 | Nishimura et al. |
| 2011/0306514 A1 | 12/2011 | Hewitt et al. |
| 2012/0043208 A1 | 2/2012 | Jin et al. |
| 2012/0046184 A1 | 2/2012 | Dawson et al. |
| 2012/0088249 A1 | 4/2012 | Jovanovich et al. |
| 2012/0156135 A1 | 6/2012 | Farokhzad et al. |
| 2012/0171694 A1 | 7/2012 | Mansfield et al. |
| 2012/0196304 A1 | 8/2012 | Dees et al. |
| 2012/0328594 A1 | 12/2012 | McKenna et al. |
| 2013/0058923 A1 | 3/2013 | Huo |
| 2013/0084561 A1 | 4/2013 | Coull et al. |
| 2014/0080119 A1 | 3/2014 | Stein et al. |
| 2014/0323330 A1 | 10/2014 | Bergo |
| 2014/0374584 A1 | 12/2014 | Stults et al. |
| 2015/0376678 A1 | 12/2015 | Krizman et al. |
| 2016/0327554 A1 | 11/2016 | Hung et al. |
| 2017/0010283 A1* | 1/2017 | Karl .................. G01N 33/6893 |
| 2017/0074869 A1 | 3/2017 | Krijgsveld et al. |
| 2017/0131276 A1 | 5/2017 | Johnston |
| 2017/0216218 A1 | 8/2017 | Farokhzad et al. |
| 2018/0136231 A1 | 5/2018 | Borrebaeck et al. |
| 2018/0172694 A1* | 6/2018 | Farokhzad .......... G01N 33/6848 |
| 2018/0356414 A1 | 12/2018 | Strano et al. |
| 2018/0361000 A1 | 12/2018 | Weissleder et al. |
| 2019/0033327 A1 | 1/2019 | Beligere et al. |
| 2019/0117799 A1 | 4/2019 | Xu et al. |
| 2019/0195903 A1* | 6/2019 | Leboudec .......... G01N 35/0092 |
| 2019/0301985 A1 | 10/2019 | Tao et al. |
| 2020/0085758 A1 | 3/2020 | Farokhzad et al. |
| 2020/0138728 A1 | 5/2020 | Farokhzad et al. |
| 2021/0072255 A1 | 3/2021 | Farokhzad et al. |
| 2021/0098083 A1 | 4/2021 | Ma et al. |
| 2021/0132071 A1 | 5/2021 | Kostarelos et al. |
| 2021/0215685 A1 | 7/2021 | Xia et al. |
| 2021/0215709 A1 | 7/2021 | Zhao et al. |
| 2021/0293801 A1 | 9/2021 | Farokhzad et al. |
| 2021/0299060 A1 | 9/2021 | Farokhzad et al. |
| 2021/0311064 A1 | 10/2021 | Farokhzad et al. |
| 2022/0226510 A1 | 7/2022 | Xu et al. |
| 2022/0260559 A1 | 8/2022 | Blume et al. |
| 2022/0334123 A1 | 10/2022 | Farokhzad et al. |
| 2022/0365096 A1 | 11/2022 | Farokhzad et al. |
| 2023/0076807 A1 | 3/2023 | Zhao et al. |
| 2023/0076840 A1 | 3/2023 | Farokhzad et al. |
| 2023/0160882 A1 | 5/2023 | Siddiqui et al. |
| 2023/0204596 A1 | 6/2023 | Manning et al. |
| 2023/0212647 A1 | 7/2023 | Farokhzad et al. |
| 2023/0213504 A1 | 7/2023 | Farokhzad et al. |
| 2023/0253113 A1 | 8/2023 | Guturu et al. |
| 2023/0324401 A1 | 10/2023 | Farokhzad et al. |
| 2023/0408503 A1 | 12/2023 | Hornburg et al. |
| 2023/0417744 A1 | 12/2023 | Xia et al. |
| 2024/0044884 A1 | 2/2024 | Farokhzad et al. |
| 2024/0044885 A1 | 2/2024 | Farokhzad et al. |

FOREIGN PATENT DOCUMENTS

| | | |
|---|---|---|
| EP | 0881494 A1 | 12/1998 |
| EP | 1308520 A2 | 5/2003 |
| EP | 1512970 A1 | 3/2005 |
| EP | 2209893 A1 | 7/2010 |
| EP | 3510402 A1 | 7/2019 |
| EP | 3554681 A1 | 10/2019 |
| JP | 2009524828 A | 7/2009 |
| JP | 2012172981 A | 9/2012 |
| JP | 2012529268 A | 11/2012 |
| JP | 2017512988 A | 5/2017 |
| WO | WO-9525281 A1 | 9/1995 |
| WO | WO-0023111 A1 | 4/2000 |
| WO | WO-0063683 A1 | 10/2000 |
| WO | WO-0065472 A1 | 11/2000 |
| WO | WO-0125791 A2 | 4/2001 |
| WO | WO-0136977 A2 | 5/2001 |
| WO | WO-0157263 A1 | 8/2001 |
| WO | WO-0157518 A2 | 8/2001 |
| WO | WO-0171360 A1 | 9/2001 |
| WO | WO-0204957 A2 | 1/2002 |
| WO | WO-0206829 A2 | 1/2002 |
| WO | WO-0208760 A1 | 1/2002 |
| WO | WO-0227329 A2 | 4/2002 |
| WO | WO-0246448 A2 | 6/2002 |

(56) References Cited

FOREIGN PATENT DOCUMENTS

| | | |
|---|---|---|
| WO | WO-02097703 A2 | 12/2002 |
| WO | WO-03014302 A2 | 2/2003 |
| WO | WO-03031031 A1 | 4/2003 |
| WO | WO-03038055 A2 | 5/2003 |
| WO | WO-03042774 A2 | 5/2003 |
| WO | WO-03057014 A2 | 7/2003 |
| WO | WO-03058198 A2 | 7/2003 |
| WO | WO-03072710 A2 | 9/2003 |
| WO | WO-03083442 A2 | 10/2003 |
| WO | WO-03086445 A1 | 10/2003 |
| WO | WO-03089937 A2 | 10/2003 |
| WO | WO-03091695 A2 | 11/2003 |
| WO | WO-03097799 A2 | 11/2003 |
| WO | WO-2004012588 A2 | 2/2004 |
| WO | WO-2004013609 A2 | 2/2004 |
| WO | WO-2004030511 A2 | 4/2004 |
| WO | WO-2004055519 A2 | 7/2004 |
| WO | WO-2004061407 A2 | 7/2004 |
| WO | WO-2004061410 A2 | 7/2004 |
| WO | WO-2004068130 A2 | 8/2004 |
| WO | WO-2004102190 A1 | 11/2004 |
| WO | WO-2005011474 A2 | 2/2005 |
| WO | WO-2005020125 A2 | 3/2005 |
| WO | WO-2005024409 A1 | 3/2005 |
| WO | WO-2007010252 A1 | 1/2007 |
| WO | WO-2007089731 A2 | 8/2007 |
| WO | WO-2007091077 A1 | 8/2007 |
| WO | WO-2008045526 A2 | 4/2008 |
| WO | WO-2010097785 A1 | 9/2010 |
| WO | WO-2010148365 A3 | 5/2011 |
| WO | WO-2011088128 A2 | 7/2011 |
| WO | WO-2012006385 A2 | 1/2012 |
| WO | WO-2012068226 A3 | 8/2012 |
| WO | WO-2012106385 A2 | 8/2012 |
| WO | WO-2012170711 A1 | 12/2012 |
| WO | WO-2013022995 A2 | 2/2013 |
| WO | WO-2015118152 A1 | 8/2015 |
| WO | WO-2018046542 A1 * | 3/2018 ......... G01N 33/5432 |
| WO | WO-2018067872 A1 | 4/2018 |
| WO | WO-2018112460 A1 | 6/2018 |
| WO | WO-2020096631 A2 | 5/2020 |
| WO | WO-2020198209 A1 | 10/2020 |
| WO | WO-2021026172 A1 | 2/2021 |

OTHER PUBLICATIONS

Adkins, Joshua N., et al., "Toward a human blood serum proteome: analysis by multidimensional separation coupled with mass spectrometry". The American Society for Biochemistry and Molecular Biology, Inc., MCP Paper (Nov. 15, 2002); 947-955.
Alavi et al.: Applying Automated Machine Learning to Accelerate Large-Scale Proteomics Data Analysis. Seer, Inc., Redwood City, CA; and Massachusetts General Hospital, Boston, MA. poster 1 page (2023).
Alavi et al.: Applying Automated ML for Classification and Regression in Large-Scale Clinical Proteomics Datasets. Seer, Inc., Redwood City, CA, poster 1 page (2023).
Alavi et al.: Challenges in Large Scale Proteomics Data Analysis: A Survey of Characterization and Correction Solutions for Batch Effects. Seer, Inc., Redwood City, CA, online video available at https://seer.bio/resources/video-gallery/?tx_category=publications &wchannelid=dfl89n6go7&wmediaid=d4eyac11ff (2022).
Alavi et al.: Challenges in Large Scale Proteomics Data Analysis: A Survey of Characterization and Correction Solutions for Batch Effects. Seer, Inc., Redwood City, CA, poster 1 page (2022).
Anderson, et al. A comparison of selected mRNA and protein abundances in human liver. Electrophoresis. Mar.-Apr. 1997;18(3-4):533-7.
Anderson, et al. The Human Plasma Proteome, Molecular & Cellular Proteomics, 2002, 845-867.
ANderson: The clinical plasma proteome: a survey of clinical assays for proteins in plasma and serum. Clin Chem 56(2):177-185 (2010).

Andriole et al.: Mortality results from a randomized prostate-cancer screening trial. N Engl J Med. 360(13):1310-1319 doi:10.1056/NEJMoa0810696 (2009).
Arvizo et al.: Identifying new therapeutic targets via modulation of protein corona formation by engineered nanoparticles. PLoS One 7(3):e33650, pp. 1-8 doi:10.1371/journal.pone.0033650 (2012).
Auluck et al.: A Cloud-Scalable Software Suite for Large-Scale Proteogenomics Data Analysis and Visualization. Seer, Inc., Redwood City, CA, poster 1 page (2022).
Auriola, Seppo et al., "Enhancement of sample loadings for the analysis of oligosaccharides isolated from Pseudomonas aeruginosa using transient isotachophoresis- electrospray -mass spectrometry". Electrophoresis (1998), 19:2665-2676.
Banez, Lionel L., et al., "Diagnostic potential of serum proteomic patterns in prostate cancer". The Journal of Urology (2003) 170:442-446.
Barkman et al.: Fabricated micro-nano devices for in vivo and in vitro biomedical applications. Wiley Interdiscip Rev Nanomed Nanobiotechnol 5(6):544-568 doi:10.1002/wnan.1236 (2013).
Baumann et al.: Standardized approach to proteome profiling of human serum based on magnetic bead separation and matrix-assisted laser desorption/ionization time-of-flight mass spectrometry. Clin Chem. 51(6):973-980 doi:10.1373/clinchem.2004.047308 (2005).
Benz et al.: Deep Plasma Proteomics at Scale with Proteograph™ Product Suite: A Performance Evaluation with Label-free and TMT Multiplexing Methods. Seer, Inc., Redwood City, CA; Sanford Burnham Prebys Medical Discovery Institute, La Jolla, CA 92037, USA, poster 1 page (2022).
Bertero, M., "Linear inverse and ill-posed problems". In Advances in Electronics and Electronic Physics. Academic Press (1989), NY.
Bigbee et al.: Tumor Markers and Immunodiagnosis. Holland-Frei Cancer Medicine, 6th edition Hamilton (ON):BC Decker; Chapter 13, pp. 209-220 (2003).
Billingsley, Janice, "Research offers hope in fight against ovarian cancer". Health & Science (Feb. 8, 2002) 3 pages.
Breiman, L., "Random Forests," Machine Learning, 2001, vol. 45, pp. 5-32.
Burgess, et al., Nanoparticle-Based Method Identifies 2200 Proteins In A Cardiovascular Disease Study Covering Known Biomarkers Among Other Differentially Expressed Proteins. Seer, Inc. Nov. 2021. 1 Page.
Buys et al.: Effect of screening on ovarian cancer mortality: the Prostate, Lung, Colorectal and Ovarian (PLCO) Cancer Screening Randomized Controlled Trial. JAMA 305(22):2295-2303 doi:10.1001/jama.2011.766 (2011).
Calvo et al.: Clinical proteomics: from biomarker discovery and cell signaling profiles to individualized personal therapy. Biosci Rep. 25(1-2):107-125 doi:10.1007/s10540-005-2851-3 (2005).
Campos, et al., In-Depth Plasma Proteomics Profiling With Nanoparticle-Based Proteograph Workflow: A Performance Evaluation Of Label-Free And TMT Multiplexing Approaches. Seer, Inc. Nov. 2021. 1 Page.
Canovi et al.: Applications of surface plasmon resonance (SPR) for the characterization of nanoparticles developed for biomedical purposes. Sensors (Basel). 12(12):16420-16432 doi:10.3390/s121216420 (2012).
Cao, Ping et al., "Analysis of peptides, proteins, protein digests, and whole human blood by capillary electrophoresis/electrospray ionization-mass spectrometry using an in-capillary electrode sheath less interface". J Am Soc Mass Spectrometry (1998), 9:1081-1088.
Capriotti et al.: Analytical methods for characterizing the nanoparticle-protein corona. Chromatographia 77(11-12):755-769 DOI: 10.1007/s10337-014-2677-x (2014).
Cazares, L. H., et al., "Normal, benign, preneoplastic, and malignant prostate cells have distinct protein expression profiles resolved by surface enhanced laser desorption/ionization mass spectrometry". Clinical Cancer Research (Aug. 2002) 8:2541-2552.
CBS News, "Setback for a silent killer". CBS News.com (Apr. 2, 2002), 2 pages.
Chambers, et al., "Proteomics: A New Approach to the Study of Disease". Journal of Pathology 2000; 192:280-288.

(56) References Cited

OTHER PUBLICATIONS

Chang, et al., Proteomic Profiling Of Prostate Cancer Plasma Specimens Using Proteograph And TIMS Technology. Seer, Inc. Nov. 2021. 1 Page.
Chen et al.: Balancing deep proteome coverage with limited sample amounts using Seer's ProteographTM Product Suite. Application Note, Seer, Inc., Redwood City, CA, pp. 1-6 (2023).
Chen et al.: Balancing deep proteome coverage with limited sample amounts using Seer's ProteographTM Product Suite. Seer, Inc., Redwood City, CA, poster 1 page (2023).
Chintamaneni et al.: Biomarkers in Alzheimer's disease: a review. ISRN Pharmacol. 2012:984786:1-6 doi:10.5402/2012/984786 (2012).
Chung et al.: Novel serum protein biomarker panel revealed by mass spectrometry and its prognostic value in breast cancer. Breast Cancer Res. 16(3):R63:1-12 doi:10.1186/bcr3676 (2014).
Clarke et al.: Characterization of renal allograft rejection by urinary proteomic analysis. Ann Surg. 237(5):660-664; discussion 664-665. doi:10.1097/01.SLA.0000064293.57770.42 (2003).
Covey, Thomas R., et al., "Structural characterization of protein tryptic peptides liquid via chromatography/mass spectrometry and collision-induced dissociation of their doubly charged molecular ions". Anal. Chern. (1991 ), 63:1193-1200.
Cramer et al.: Ovarian cancer biomarker performance in prostate, lung, colorectal, and ovarian cancer screening trial specimens. Cancer Prev Res (Phila) 4(3):365-374 doi:10.1158/1940-6207.CAPR-10-0195 (2011).
CRISP—Computer retrieval of information on scientific projects [abstract], https://www.yumpu.com/en/document/read/24805060/crisp-computer-retrieval-of-information-on-scientific-projects- Downloaded May 9, 2002, 2 pages.
Dai et al.: Combining proteograph technology with zeno swath dia acquisition enables the potential for deep, unbiased discovery of biomarkers in blood. PrognomiQ Inc., 1900 Alameda de las Pulgas, Suite 100, San Mateo, California, USA, poster 1 page (2022).
Diamandis, Eleftherios P., "Point proteomic patterns in biological fluids: do they represent the future of cancer diagnostics?". Clinical Chemistry (2003) 49(8) 1272-1278.
Donovan, et al., Deep, Rapid and Unbiased Plasma Proteomics with the Proteograph™ Product Suite Enables Proteogenomic Studies with Differential Analysis of Proteoforms. Seer, Inc. Sep. 2021. 5 Pages.
Donovan et al.: Functionally distinct BMP1 isoforms show an opposite pattern of abundance in plasma from non-small cell lung cancer subjects and controls. PLoS One. 18(3): e0282821, pp. 1-11. doi:10.1371/journal.pone.0282821 (2023).
Donovan et al.: Peptide-centric analyses of human plasma enable increased resolution of biological insights into non-small cell lung cancer relative to protein-centric analysis. Seer, Inc. Biorxiv 2022. 01.07.475393, pp. 1-21 doi:10.1101/2022.01.07.475393 (2022).
Donovan et al.: Proteoform inference using a proteogenomic approach in non-small cell lung cancer and healthy control plasma proteomes reveals disease-associated protein isoforms. Seer Inc., Redwood City, CA USA, poster 1 page (2022).
Editorial, "Proteomic diagnostics tested". Nature (Jun. 3, 2004), 429(3), 487.
Ellenberger et al.: Robust, high throughput and deep plasma proteomics workflow with engineered nanoparticle panels. Seer, Inc., Redwood City, CA, poster 1 page (2022).
Ellenberger et al.: Robust in-depth label-free plasma proteomics with engineered nanoparticle panels: An evaluation of micro-pillar array columns. and FAIMS peptide separation. Seer, Inc., Redwood City, CA, poster 1 page (2022).
Espina et al.: Use of proteomic analysis to monitor responses to biological therapies. Expert Opin Biol Ther. 4(1):83-93 doi: 10.1517/14712598.4.1.83 (2004).
Etzioni, Ruth, et al., "Combining biomarkers to detect disease with application to prostate cancer". Biostatistics (2003), 4(4), 523-538.
Faunce et al.: Integrated research into the nanoparticle-protein corona: a new focus for safe, sustainable and equitable development of nanomedicines. Nanomedicine (Lond). 3(6):859-866 doi:10.2217/17435889.3.6.859 (2008).
Fengming et al.: Biomarkers of inflammatory bowel disease. Dis Markers 2014:710915:1-11 doi:10.1155/2014/710915 (2014).
Ferdosi et al.: Engineered nanoparticles enable deep proteomics studies at scale by leveraging tunable nano-bio interactions. PNAS USA 119(11):e2106053119, pp. 1-11 doi:10.1073/pnas.2106053119 (2022).
Ferdosi et al.: Enhanced Competition at the Nano-Bio Interface Enables Comprehensive Characterization of Protein Corona Dynamics and Deep Coverage of Proteomes. Adv Mater. e2206008, pp. 1-11 doi:10.1002/adma.202206008 (2022).
Ferdosi et al.: Multi-nanoparticle Workflow Enables Deep Plasma Proteomics at Scale, with Enhanced Precision, and Depths of Coverage. Seer, Inc. (Mar. 2022).
Ferdosi, et al., Proteograph™ multi-nanoparticle proteins coronas enable deep plasma proteomics studies at scale with unmatched sensitivity in combination with trapped ion mobility. Seer, Inc. Mar. 2021. 1 Page.
Ferdosi et al.: The Nanoparticle-Based Plasma Proteomics Workflow enables the Investigation of Glycoproteome. Seer, Inc., Redwood City, CA, poster 1 page (2022).
Ferdosi et al.: The Nanoparticle-Based Plasma Proteomics Workflow enables the Investigation of Glycoproteome. Seer, Inc., Redwood City, CA, poster 1 page (2023).
Ferdosi, et al., Unlocking Plasma Proteomics at Scale: A multi nanoparticle approach to improve the depth of coverage. Seer, Inc. Oct. 2021. 1 Page.
Ferrucci JT. Colon screening with virtual colonoscopy: Promise, Polyps, Politics. AJR, vol. 177, 2001, pp. 975-988.
Figeys, Daniel et al., "High sensitivity analysis of proteins and peptides by capillary electrophoresis-tandem mass spectrometry: recent developments in technology and applications". Electrophoresis, (1998), 19:885-892.
Findeisen et al.: Preanalytical impact of sample handling on proteome profiling experiments with matrix-assisted laser desorption/ionization time-of-flight mass spectrometry. Clin Chem. 51(12):2409-2411 doi:10.1373/clinchem.2005.054585 (2005).
Flory et al.: A Highly Scaled Proteomic Discovery Study for Prostate Cancer Diagnostic Signatures Using Proteograph TM Workflow with Trapped Ion Mobility Mass Spectrometry. Oregon Health and Science University, Knight Cancer Institute, Cancer Early Detection Advanced Research Center; University of Texas Health Science Center at San Antonio Health; Fred Hutchinson Cancer Research Center; Bruker Daltonics, Billerica; Seer Inc., poster 1 page (2022).
Foroozandeh et al.: Merging worlds of nanomaterials and biological environment: factors governing protein corona formation on nanoparticles and its biological consequences. Nanoscale Res Lett. 10(221):1-12 doi:10.1186/s11671-015-0922-3 (2015).
Fung, Eric T., et al., "Classification of cancer types by measuring variants of host response proteins using SELDI serum assays," Int. J. Cancer (2005) 115:783-789.
Fung, et al. ProteinChip(R) clinical proteomics: Computational challenges and solutions. Biotechniques. 2002; 32(3): S34-S41.
Gajadhar et al.: An integrated data processing and visualization suite leveraging cloud scalable architecture for large-cohort proteogenomics data analysis and interpretation. Seer, Inc., Redwood City, CA, poster 1 page (Jun. 2022).
Gajadhar et al.: Unbiased human biofluids analysis using a scalable, deep, automated, multi-nanoparticle-based proteomics workflow. Seer, Inc., Redwood City, CA, poster 1 page (2023).
Garcia et al.: A high-throughput and robust nanoparticle-based label-free mass spectrometry workflow for deep plasma proteomics at scale. Seer, Inc., Redwood City, CA, poster 1 page (2023).
Geracimos, A., "Outwitting Ovarian Cancer". Conelogic Systems, Inc., Press Release dated Apr. 16, 2002, 4 pages.
Geromanos, S., et al., "Injection adaptable Fine Ionization Source ('JaFIS') for Continuous Flow Nano-electrospray". Rapid Commun. Mass Spectrom (1998) 12:551-556.

(56) References Cited

OTHER PUBLICATIONS

Go from data to insight with the proteograph analysis suite. Seer. bio. Aug. 2021. Available at: https://seer.bio/resources/document-library/.

Guerrier et al.: A simplified monobuffer multidimensional chromatography for high-throughput proteome fractionation. J Chromatogr A. 1073(1-2):25-33 doi:10.1016/j.chroma.2004.10.002 (2005).

Guo, Xu et al., "Analysis of metallonthioneins by means of capillary electrophoresis coupled to electrospray mass spectrometry with sheathless interfacing" Rapid Commun. Mass Spectrom. (1999), 13:500-507.

Guturu et al.: High-throughput plasma proteomics to identify diabetes associated protein biomarkers and pQTLs. 1. Seer, Inc., Redwood City, CA; and 2. Weill Cornell Medicine-Qatar, Doha, State of Qatar, poster 1 page (2023).

Guturu et al.: Systematic analysis of Dia LC-MS protein rollup strategies and their impact on phenotype association and proteogenomic applications. Seer, Inc., Redwood City, CA; and Massachusetts General Hospital, Boston, MA. poster 1 page (2023).

Gygi, et al. Correlation between protein and mRNA abundance in yeast. Mol Cell Biol. Mar. 1999;19(3):1720-30.

Hakimi et al.: Robust and Deep Plasma Proteomics using a Multi Nanoparticle-based Workflow coupled with an Orbitrap Exploris 480 Mass Spectrometry and FAIMS Pro Interface. ThermoFisher Scientific, San Jose, CA; and Seer, Inc., Redwood City, CA, poster 1 page (2023).

Haran, Christine, "The promise of proteins—Do these tricky molecules hold the answers to cancer?". (Oct. 2002) 43-47.

Harrison, Harold H., et al., "Multiple serum protein abnormalities in carbohydrate-deficient glycoprotein syndrome: pathognomomic finding of two-dimensional electrophoresis?". Clinical Chemistry (1992), 38:1390-1392.

Havugimana et al., A census of human soluble protein complexes, Cell, 150(5): 1068-1081, 2012.

Hayes, Roger N., et al. "Collision-Induced Dissociation". Methods in Enzymology, (1990), vol. 193, pp. 237-263.

Henry, Celia, "Diagnosing ovarian cancer—Proteomics shows promise of early detection of deadly disease". Science (Feb. 18, 2003) 18.

Henzel et al. Identifying proteins from two-dimensional gels by molecular mass searching of peptide fragments in protein sequence databases. PNAS, 1993, vol. 90, pp. 5011-5015.

Hilario, Melanie, et al., "Machine learning approaches to lung cancer prediction from mass spectra". Protoemics (2003) 3:1716-1719.

Hollon, Tom "Software Zeroes in on ovarian cancer". The Scientist (Apr. 15, 2002) 16(8):16.

Hong et al.: Discrimination Analysis of Mass Spectrometry Proteomics for Lung Adenocarcinoma Detection. Laboratory Medicine 42(6):6, pp. 344-349. doi:10.1309/LMXWEJV3FFDR0DHH (2011).

Hornburg, et al., Deep Plasma Proteomics at Scale: A machine learning enhanced multi nanoparticle approach to improve the depth of plasma proteome coverage. Seer, Inc. Nov. 2021. 1 Page.

Hornburg et al.: Enhanced Competition at the Nano-Bio Interface Enables Comprehensive Characterization of Protein Corona Dynamics and Deep Coverage of Proteomes. Seer Inc., Redwood City, CA USA, poster 1 page (2022).

Hornburg, et al., Enhanced competitive protein exchange at the nano-bio interface enables ultra-deep coverage of the human plasma proteome. Seer, Inc. Jan. 2022. pp. 1-18.

Hornburg et al.: Evaluation of an unbiased, deep, and scalable nanoparticle-based proteomics workflow for limited plasma sample volume from model organisms. Seer, Inc., Redwood City, CA, poster 1 page (2022).

Houerbi et al.: Deep Profiling of the Spaceflight Plasma Proteome reveals Changes in Reactive Oxygen Species, Extracellular Matrix and Lipid Metabolism. Weill Cornell Medicine, New York, NY; Seer, Inc., Redwood City, CA; Colorado State University, Fort Collins, CO; and SpaceX, Hawthorne, CA, poster 1 page (2022).

Huang et al.: Deep, Rapid and Unbiased Plasma Proteomics with Differential Analysis of Proteoforms Enabling Proteogenomic Studies in a NSCLC Lung Cancer Study. Seer, Inc. (Mar. 2022).

Huang et al.: Deep, Rapid and Unbiased Plasma Proteomics with Peptide Correlation Analysis Enabling Proteoform Inference and Differential analysis in a NSCLC Lung Cancer Study. Seer, Inc., Redwood City, CA, poster 1 page (2022).

Huang et al.: Deep, unbiased and quantitative mass spectrometry-based plasma proteome analyses of adaptive response to COVID-19 vaccine. 1. Seer, Inc., Redwood City, CA, USA; 2. Plexium, San Diego, CA, USA; 3. Federal University of Rio Grande do Sul, Porto Alegre, Brazil; and 4. Sanford Burnham Prebys, La Jolla, CA, USA, poster 1 page (2023).

Huang et al.: Deep, Unbiased and Quantitative mass spectrometry-based plasma proteome analyses of adaptive response to COVID-19 vaccine. Seer, Inc., Redwood City, CA, poster 1 page (2023).

Huang et al.: Proteoform detection in deep plasma proteomics through peptide expression correlation. Seer, Inc., Redwood City, CA, poster 1 page (2023).

Huo et al.: Developing a nanoparticle test for prostate cancer scoring. J Transl Med. 10(44):1-8 doi:10.1186/1479-5876-10-44 (2012).

Johannes, Laura, "Tiny protein may lead to better screen test for prostate cancer". Dow Jones (Nov. 4, 2003), 1-2.

Just et al.: A novel cloud-native pipeline enabling deep, unbiased proteomics at extreme scale. Seer, Inc., Redwood City, CA, poster 1 page (2023).

Just et al.: Matrix-Matched Calibration Curves Provide Verification of Quantitative Data-Independent Acquisition Techniques for Deep Plasma Proteomics. Seer, Inc., Redwood City, CA, poster 1 page (2022).

Kaiser, Thorsten et al., "Capillary electrophoresis coupled to mass spectrometer for automated and robust polypeptide determination in body fluids for clinical use". Electrophoresis (2004), 25:2044-2055.

Kaiser, Thorsten et al., "Capillary electrophoresis coupled to mass spectrometry to establish polypeptide patterns in dialysis fluids". Journal of Chromatography A (2003 ), 1013:157-171.

Kajita, Yoshihiro, et al., "Clinical Study on Increased Serum Thyroxine-Binding Globulin in Cancerous State," Endocrinol. Japon (1981) 28 (6): 785-791.

Keshishian, Hasmik et al. Multiplexed, Quantitative Workflow for Sensitive Biomarker Discovery in Plasma Yields Novel Candidates for Early Myocardial Injury. Molecular & cellular proteomics : MCP vol. 14,9 (2015): 2375-93. doi:10.1074/mcp.M114.046813.

Khadka et al.: An unbiased multi-omics approach for the detection of pancreatic cancer biomarkers utilizing ion-mobility mass spectrometry and nanoparticle-based proteograph technology. PrognomiQ Inc., 1900 Alameda de las Pulgas, Suite 100, San Mateo, CA, USA, poster 1 page (2022).

Kiehntopf et al.: Use of SELDI-TOF mass spectrometry for identification of new biomarkers: potential and limitations. Clin Chem Lab Med. 45(11):1435-1449 doi:10.1515/CCLM.2007.351 (2007).

Kitano, et al., Cloud scalable omics data analysis pipeline using serverless task infrastructure. Seer, Inc. Nov. 2021. 1 Page.

Kluger et al.: Ultra-high coverage of the serum proteome using a multi-nanoparticle based workflow. Seer Evotec poster, 1 page (2022).

Koene et al.: Serum protein profiles as potential biomarkers for infectious disease status in pigs. BMC Vet Res. 8(32):1-14 doi:10.1186/1746-6148-8-32 (2012).

Kojima et al.: Detection of elevated proteins in peritoneal dissemination of gastric cancer by analyzing mass spectra data of serum proteins. J Surg Res. 155(1):13-17 doi:10.1016/j.jss.2008.07.024 (2009).

Koo et al., Amyloid diseases: abnormal protein aggregation in neurodegeneration Proc. Natl. Acad. Sci. U.S. A 96:9989-9990, 1999.

Koo et al.: Liquid flow in microchannels: experimental observations and computational analyses of microfluidics effects. Journal of Micromechanics and Microengineering 13(5):568-579 (2003).

(56) References Cited

OTHER PUBLICATIONS

Kozak et al.: Identification of biomarkers for ovarian cancer using strong anion-exchange ProteinChips: potential use in diagnosis and prognosis. Proc Natl Acad Sci USA 100(21):12343-12348 doi:10.1073/pnas.2033602100 (2003).
Kundin, W.D., et al., "Cancer Serum Index: A useful Nonspecific Test as a Parameter in Multimodality Screening and Assessment of Patients With Cancer of the Prostate," The Prostate (1981) 2:207-217.
Lacar et al.: Accelerating throughput with the ProteographTM XT Assay. Seer, Inc., Application Note (CF-1059 Rev A), pp. 1-8 (2023).
Lebrecht et al.: Surface-enhanced Laser Desorption/Ionisation Time-of-flight Mass Spectrometry to Detect Breast Cancer Markers in Tears and Serum. Cancer Genomics Proteomics. 6(2):75-83 (2009).
Lee et al.: Revealing urologic diseases by proteomic techniques. J Chromatogr B Analyt Technol Biomed Life Sci. 815(1-2):203-213 doi:10.1016/j.jchromb.2004.11.008 (2005).
Lehrer, S., et al., "Putative protein markers in the sera of men with prostatic neoplasms". BJU International (2003) 92:223-225.
Leong et al.: Profiling of apoptotic changes in human breast cancer cells using SELDI-TOF mass spectrometry. Cell Physiol Biochem. 20(5):579-590 doi:10.1159/000107541 (2007).
Levitan et al.: Evaluation of engineered multi-nanoparticle-based proteomics analysis for unbiased, deep, and rapid analysis of fetal bovine serum derived cell culture media. Seer, Inc., Redwood City, CA, poster 1 page (2022).
Li et al.: A high-throughput and robust multi nanoparticle-based label-free mass spectrometry workflow for deep plasma proteomics at scale. Seer, Inc., Redwood City, CA, poster 1 page (2023).
Li et al.: LC-MS MS1 image map classification enables real-time sample quality control for nanoparticle-based deep untargeted proteomics. Seer, Inc., Redwood City, CA, poster 1 page (2023).
Li, et al. "Proteomics and Bioinformatics approaches for identification of serum biomakers to detect breast cancer". Clinical Chemistry. 2002; 48(8): 1296-1304.
Li, Jinong et al., "Detection of prostate cancer using serum proteomics pattern in a histologically confirmed population". The Journal of Urology (May 2004), 171:1782-1787.
Lilien et al.: Probabilistic disease classification of expression-dependent proteomic data from mass spectrometry of human serum. J Comput Biol. 10(6):925-946 doi:10.1089/106652703322756159 (2003).
Lin et al.: Plasma proteomic pattern as biomarkers for ovarian cancer. Int J Gynecol Cancer 16 Suppl 1:139-146 doi:10.1111/j.1525-1438.2006.00475.x (2006).
Liotta, Lance, A., et al., "Written in Blood". Nature, (Oct. 30, 2003), vol. 425, p. 905.
Liu et al.: MALDI-TOF MS combined with magnetic beads for detecting serum protein biomarkers and establishment of boosting decision tree model for diagnosis of hepatocellular carcinoma. Am J Clin Pathol. 134(2):235-241 doi:10.1309/AJCPA6C6NOGFLYIR (2010).
Liu et al.: Proteomic profiling of hepatitis B virus-related hepatocellular carcinoma with magnetic bead-based matrix-assisted laser desorption/ionization time-of-flight mass spectrometry. Acta Biochim Biophys Sin (Shanghai) 43(7):542-550 doi:10.1093/abbs/gmr044 (2011).
Magni et al.: Biomarkers discovery by peptide and protein profiling in biological fluids based on functionalized magnetic beads purification and mass spectrometry. Blood Transfus. 8 Suppl 3(Suppl 3):s92-s97 doi:10.2450/2010.015S (2010).
Mani et al.: Data mining strategies to improve multiplex microbead immunoassay tolerance in a mouse model of infectious diseases. PLoS One 10(1):e0116262:1-19. doi:10.1371/journal.pone.0116262 (2015).
Markey, Mia K., et al. "Decision tree classification of proteins identified by mass spectrometry of blood serum samples from people with and without lung cancer" Proteomics (2003) 3:1678-1679.

Marshall, John, et al., "Processing of serum proteins underlies the mass spectral fingerprinting of myocardial infraction". Journal of Proteome Research (Jan. 20, 2003) 12 pages.
May: Digging Deep to Release the Power of the Proteome. Inside Precision Medicine, pp. 1-11 [retrieved online from https://www.insideprecisionmedicine.com/topics/translational-research/proteomics/digging-deep-to-release-the-power-of-the-proteome/] (2023).
Mehan et al.: Chapter 20. Highly Multiplexed Proteomic Platform for Biomarker Discovery, Diagnostics, and Therapeutics. Complement Therapeutics, Advances in Experimental Medicine and Biology, Lambris, J. D. et al. (eds.), Springer Science+Business Media, New York, pp. 283-300. doi:10.1007/978-1-4614-4118-2 (2013).
Mertens et al.: On the use of double cross-validation for the combination of proteomic mass spectral data for enhanced diagnosis and prediction. Statistics & Probability Letters 81(7):759-766 (2011).
Mian, Shahid, et al., "A prototype methodology combining surface-enhanced laser desorption/ionization protein chip technology and artificial neural network algorithms to predict the chemoresponsiveness of breast cancer cell lines exposed to Paclitaxel and Doxorubicin under in vitro conditions". Proteomics (2003) 3:1725-1737.
Milani et al.: Reversible versus irreversible binding of transferrin to polystyrene nanoparticles: soft and hard corona. ACS Nano. 6(3):2532-2541 doi:10.1021/nn204951s (2012).
Miller, et al. "Antibody microarray profiling of human prostate cancer sera: Antibody screening and identification of potential biomarkers." Proteomics. vol. 3, pp. 56-63, (2003).
Mobley, J.A., et al., "Monitoring The Serological Proteome: The Latest Modality in Prostate Cancer Detection," The Journal of Urology (Jul. 2004) vol. 172: 331-337.
Mohtashemi et al.: Improving LC-MS Data Analysis Pipelines to Leverage Distributed Compute Engines. Seer, Inc., Redwood City, CA, poster 1 page (2022).
Mohtashemi, et al., Mass spectrometry data acquisition with machine learning methods for deep plasma protein characterization. Seer, Inc. Nov. 2021. 1 Page.
Moss et al.: Integrated Plasma Multi-Omics Using Nanoparticle Technology and Single Shot Capillary MS. University of Wisconsin-Madison, Madison, WI, 53706, USA; Morgridge Institute for Research, Madison, WI ,53715, USA; and Seer, Redwood City, CA, poster 1 page (2022).
Motamedchaboki et al.: Deep plasma protein profiling in Alzheimer's disease (AD) with a novel unbiased and scalable proteogenomics approach. Seer, Inc., Redwood City, CA, poster 1 page (2022).
Nakamura et al.: Differential profiling analysis of proteins involved in anti-proliferative effect of interferon-alpha on renal cell carcinoma cell lines by protein biochip technology. Int J Oncol. 28(4):965-970 (2006).
Nanni et al.: Serum protein profiling in patients with inflammatory bowel diseases using selective solid-phase bulk extraction, matrix-assisted laser desorption/ionization time-of-flight mass spectrometry and chemometric data analysis. Rapid Commun Mass Spectrom. 21(24):4142-4148 doi:10.1002/rcm.3323 (2007).
Neuhoff, et al. "Mass spectrometry for the detection of differentially espressed proteins: a comparison of surface-enhanced laser desorption/ionization and capillay electrophoresis/mass spectrometry". Rapid Cornmun. Mass Spectrom. 2004; 18(2): 149-156.
Neusub, Christian et al., "A robust approach for the analysis of peptides in the low femtomole range by capillary electrophoresis-tandem mass spectrometry". Electrophoresis (2002), 23:3149-3159.
Neville, Padraic, et al., "Generalizable mass spectrometry mining used to identify disease state biomarkers from blood serum". Proteomics (2003) 3:1710-1715.
Notice of Allowance dated Apr. 2, 2008 for U.S. Appl. No. 11/178,262.
Notice of Allowance dated Nov. 1, 2010 for U.S. Appl. No. 12/172,988.
Office action dated Jan. 26, 2005 for U.S. Appl. No. 10/645,863.
Office action dated Feb. 1, 2007 for U.S. Appl. No. 10/760,100.
Office action dated Feb. 10, 2012 for U.S. Appl. No. 13/018,622.
Office action dated Mar. 2, 2016 for U.S. Appl. No. 14/166,626.
Office action dated Apr. 19, 2005 for U.S. Appl. No. 10/645,863.
Office action dated Jun. 15, 2005 for U.S. Appl. No. 10/645,863.
Office action dated Jun. 23, 2016 for U.S. Appl. No. 14/166,626.
Office Action dated Sep. 26, 2007 for U.S. Appl. No. 11/178,262.

(56) References Cited

OTHER PUBLICATIONS

Office action dated Dec. 31, 2012 for U.S. Appl. No. 13/018,622.
Oka, Amita R et al. Functional Proteomic Profiling of Phosphodiesterases Using SeraFILE Separations Platform. International journal of proteomics vol. 2012 (2012): 515372. doi:10.1155/2012/515372.
Ornstein, David K., et al., "Serum Proteomic Profiling Can Discriminate Prostate Cancer From Benign Prostates in Men With Total Prostate Specific Antigen Levels Between 2.5 And 15.0 NG/ML," The Journal of Urology (Oct. 2004) vol. 172: 1302-1305.
Page et al.: A Cloud-Scalable Software Suite for Large-Scale Proteogenomics Data Analysis and Visualization. Seer, Inc., Redwood City, CA, poster 1 page (2023).
Paroni, Rita et al., "Creatinine determination in serum by capillary electrophoresis". Electrophoresis (2004), 25:463-468.
Patterson, S.D., Proteomics: the industrialization of protein chemistry. Current Opinion in Biotechnology, 2000; 11: 413-418.
Pease et al.: Deep and unbiased proteomics analysis reveals differences between serum and plasma proteome in matched donors. Seer, Inc., Redwood City, CA, poster 1 page (2022).
Pease et al.: Evaluation of blood-based sample types for deep plasma proteomics. Application Note, Seer, Inc., Redwood City, CA, pp. 1-4 (2023).
Pena et al.: Evaluation of deep plasma proteomic analysis with the ProteographTM workflow and TMT sample labeling. 1. Proteomics Shared Resource at Sanford Burnham Prebys, La Jolla, CA; and 2. Seer, Inc., Redwood City, CA, pp. 1-5 (2023).
Petricoin III, E. F., et al., "Serum proteomic patterns for detection of prostate cancer". JNCI (2002), 94(20):1576-1578.
Petricoin III, E. F., et al., "Use of proteomic patterns in serum to identify ovarian cancer". The Lancet (2002), 359:572-577.
Platt et al.: A Cloud-scalable Software Suite for Large-Scale Proteogenomics Data Analysis and Visualization. Seer, Inc., Redwood City, CA, poster 1 page (2022).
Purohit, Parol V., et al., "Discriminant models for high-throughput proteomics mass spectrometer data". Proteomics (2003) 3: 1699-1703.
Qu, Yinsheng, et al., "Boosted decision tree analysis of surface-enhanced laser desorption/ionization mass spectral serum profiles discriminates prostate cancer from noncancer patients". Clinical Chemistry (2002), 48(10): 1835-1843.
Reddy, et al. "SELDI Proteinchip(R) array technology: protein-based predictive medicine and drug discovery applications. Journal of Biomedicine & Biotechnology". 2003 (4): 237-241.
Reixach, et al. Tissue damage in the amyloidoses: Transthyretin monomers and nonnative oligomers are the major cytotoxic species in tissue culture. Proc Natl Acad Sci U S A. Mar. 2, 2004;101(9):2817-22. Epub Feb. 23, 2004.
Riley et al.: A Cloud-Scalable Software Suite for Large-Scale Proteogenomics Data Analysis and Visualization. Seer, Inc., Redwood City, CA, poster 1 page (2023).
RNA (ribonucleic acid), 1988. Illustrated Dictionary of Science, Andromeda. Retrieved online on Feb. 8, 2012 http://www.credoreference.com/etry/andidsci/rna_ribonucleic_acid.
Robey, Edwin L., et al., "Cancer Serum Index And Prostatic Acid Phosphatase For Detection Of Progressive Prostatic Cancer," The Journal of Urology (Oct. 1985) vol. 134: 787-790.
Rohde, E. et al., "Comparison of protein mixtures in aqueous humor by membrane preconcentration—capillary electrophoresis—mass spectrometry". Electrophoresis (1998), 19:2361-2370.
Rostenberg, Israel, et al., "Gc Globulin and Prealbumin Serum Levels in Patients With Cancer and Benign Inflammatory Diseases and in Asymptomatic Smokers," Journal of the National Cancer Institute (Feb. 1997) vol. 62 No. 2:299-300.
Rubin, Rita, "Blood test may spot ovarian cancer earlier" Health & Science (Feb. 8, 2002) 2 pages.
Rui, et al., Use of serological proteomic methods to find biomarkers associated with breast cancer. Proteomics, Apr. 2003; 3(4): 433-439.
Sacanna et al.: Thermodynamically stable pickering emulsions. Phys Rev Lett. 98(15):158301 doi:10.1103/PhysRevLett.98.158301 (2007).
Sakulkhu et al.: Protein corona composition of superparamagnetic iron oxide nanoparticles with various physico-chemical properties and coatings. Sci Rep. 4:5020:1-9 doi: 10.1038/srep05020 (2014).
Sassi, Alexander P., et al., "An automated, sheathless capillary electrophoresis-mass spectrometry platform for discovery of biomarkers in human serum". Electrophoresis (2005), 26:1500-1512.
Schroder, et al. Screening and prostate-cancer mortality in a randomized European study. N Engl J Med. Mar. 26, 2009;360(13):1320-8. doi: 10.1056/NEJMoa0810084. Epub Mar. 18, 2009.
Schultz, Gary A. et al., "Development of a proteome marker model for ovarian cancer using direct analysis of diluted serum by automated nanoelectrospray TOFMS" ASMS (2003) 2 pages.
Schwamborn et al.: Serum proteomic profiling in patients with bladder cancer. Eur Urol. 56(6):989-997 doi:10.1016/j.eururo.2009.02.031 (2009).
Schweigert, Florian J., et al., "Transthyretin, a Biomarker for Nutritional Status and Ovarian Cancer," Cancer Research (Feb. 1, 2005) 65 (3): 1114.
Seer, Inc. A New Gateway to the Proteome—Unbiased, Deep, Rapid Proteomics at Scale, YouTube, Mar. 20, 2021 URL: https://www.youtube.com/watch?v=dDe--0QMAX8.
Seer, Inc. A New Gateway to the Proteome, YouTube, Mar. 20, 2021, https://www.youtube.com/watch?v=O-goKi6_1P8.
Seer, Inc. Comparison Of Proteograph Product Suite to Peptide Fractionation, YouTube, Mar. 2021, https://www.youtube.com/watch?v=eUliHi7FB_I.
Seer, Inc. Customer Stories—Mark Flory Ph.D., OHSU/Knight Cancer Research Institute/CEDAR, YouTube, Apr. 30, 2021, https://www.youtube.com/watch?v=C3BTvhOzx0M.
Seer, Inc. Initialize and Prepare the SP100, YouTube, May 25, 2021 URL: https://www.youtube.com/watch?v=aID-8qhC9hY.
Seer, Inc. Loading Reagents and Plasticware onto the SP100 Work Deck, YouTube, May 25, 2021 URL: https://www.youtube.com/watch?v=ND3QYKvGub8.
Seer, Inc. Performing SP100 Clean-up and the Sample Plate Layout, YouTube, May 25, 2021 URL: https://www.youtube.com/watch?v=S070uN-KgTs.
Seer, Inc. Plasma Protein Profiling of Alzheimer's and Mild Cognitive Impairment, YouTube, Mar. 20, 2021 URL: https://www.youtube.com/watch?v=YLEa_7pfDuQ.
Seer, Inc. Preparing and Loading the Nanoparticles, Samples, and Controls, YouTube, May 25, 2021 URL: https://www.youtube.com/watch?v=I2MTSxjMaF4.
Seer, Inc.: Press release PPT, with online publications (published Sep. 2022).
Seer Inc., Proteograph Assay quick reference work deck layout [retrieved online Jan. 2022].
Seer, Inc. Proteograph Product Suite—Detailed 10 Minute Overview, YouTube, Mar. 20, 2021, https://www.youtube.com/watch?v=jWPKiL9fsBw.
Seer, Inc. Proteograph Product Suite—Short 3 Minute Overview, YouTube, Mar. 20, 2021, https://www.youtube.com/watch?v=u0cWT-FeEI4.
Seer, Inc. Proteograph Product Suite with the Bruker tims TOF Platform, YouTube, Apr. 10, 2021, https://www.youtube.com/watch?v=upzRuK3OAbc.
Seer, Inc. Proteograph Safety Data Sheet. URL: https://seer.bio/wp-content/uploads/2021/12/Proteograph-Assay-SDS.pdf Published Nov. 2021 (retrieved online Feb. 2022) 122 Pages.
Seer, Inc., Proteograph Training Series: Initialize and prepare the SP100, YouTube, Jan. 4, 2022, https://www.youtube.com/watch?v=jUzl-VSD23k.
Seer, Inc. Proteograph™ Training Series: Loading Reagents and Plasticware onto the SP100 Work Deck, YouTube, Jan. 4, 2022, https://www.youtube.com/watch?v=gAYy7Usa0XI.
Seer, Inc. Proteograph Training Series: Preparing and Loading the nanoparticles, samples, and controls, YouTube, Jan. 4, 2022, https://www.youtube.com/watch?v=GYnleXjmDml.
Seer, Inc., Proteograph Training Series: Preparing Materials. YouTube, Jan. 4, 2022, https://www.youtube.com/watch?v=vHId2oQRavA.
Seer, Inc., Proteograph Training Series: SP100 automation instrument [Functions & Components], YouTube, Jan. 4, 2022, https://www.youtube.com/watch?v=-8v2_Bqoi4Y.

(56) References Cited

OTHER PUBLICATIONS

Seer, Inc. Proteograph Training Series: SP100 Clean-up & Sample Plate Layout, YouTube, Jan. 4, 2022, https://www.youtube.com/watch?v=noXIYMZc0FI.
Seer, Inc. Proteograph Training Series: Starting the proteograph assay method, YouTube, Jan. 4, 2022, https://www.youtube.com/watch?v=nLqZT623u1M.
Seer, Inc., Proteograph Traning Series: Setting up the proteograph method, YouTube, Jan. 4, 2022, https://www.youtube.com/watch?v=XastVfF_wls.
Seer, Inc. ProteographTM Analysis Suite User Guide. URL: https://seer.bio/wp-content/uploads/2021/12/PAS_User_Guide_CF-1003-B.pdf Published Oct. 2021 (retrieved online Feb. 2022) 103 Pages.
Seer, Inc. ProteographTM Assay Quick Reference Work Deck Layout. CF-1020 Rev A URL: https://seer.bio/wp-content/uploads/2021/12/Seer_ProteographAssay_Quick_Reference_RevA.pdf (retrieved online Feb. 2022) 2 Pages.
Seer, Inc. ProteographTM Product Suite: An automated workflow that scales with your studies, YouTube, Jan. 4, 2022 URL: https://www.youtube.com/watch?v=hb16g8JfWnU.
Seer, Inc. ProteographTM Quickstart Series: How to Load Plastics and Reagents onto the SP100, YouTube, Jan. 7, 2022 URL: https://www.youtube.com/watch?v=ay4LDy5J0uw.
Seer, Inc. ProteographTM Quickstart Series: How to Prepare and Load the Nanoparticles, Samples & Controls, YouTube, Jan. 7, 2022 URL: https://www.youtube.com/watch?v=oP40VjQ8yoE.
Seer, Inc. ProteographTM Quickstart Series: Initialize and Prepare the SP100, YouTube, Jan. 7, 2022 URL: https://www.youtube.com/watch?v=qmvy7QKbjRI.
Seer, Inc. ProteographTM Quickstart Series: SP100 Clean-up & Sample Plate Layout, YouTube, Jan. 7, 2022 URL: https://www.youtube.com/watch?v=HSnXFkxq-Fw.
Seer, Inc. ProteographTM Quickstart Series: Starting the Proteograph Assay Method, YouTube, Jan. 7, 2022 URL: https://www.youtube.com/watch?v=aoJoWMDSWjg.
Seer, Inc. ProteographTM Quickstart Series: Step-by-Step on Preparing Materials, YouTube, Jan. 7, 2022 URL:https://www.youtube.com/watch?v=UVIt4AcjsSg.
Seer, Inc. ProteographTM Quickstart Series: Step-by-Step on SP100 Automation Instrument, YouTube, Jan. 7, 2022 URL: https://www.youtube.com/watch?v=zBrCzhmLiJU.
Seer, Inc.: Release Notes, Proteograph™ Analysis Suite v2.0, pp. 1-2 (published Aug. 3, 2022).
Seer, Inc.: Safety Data Sheet. Nov. 2021. Available at: https://seer.bio/wp-content/uploads/2021/12/Proteograph-Assay-SDS.pdf.
Seer, Inc. Seer's Nanoparticle Approach: A Novel Approach to Unbiased, Deep, Rapid and Scalable Proteomics, YouTube, Mar. 20, 2021, https://www.youtube.com/watch?v=ArvpW3IPfA0.
Seer, Inc. SP100 Automation Instrument Site Preparation Guide (CF-1017 B). URL: https://seer.bio/wp-content/uploads/2022/02/SP100_Site_Prep_Guide_CF_1017_B-1.pdf Published Jun. 2021 (retrieved online Feb. 2022) 15 Pages.
Seer, Inc. SP100 Automation Instrument Site Preparation Guide (Int. CF-1014 A). URL: https://seer.bio/wp-content/uploads/2022/02/SP100_Site_Prep_Guide_International_CF_1015_A.pdf Published Dec. 2021 (retrieved online Feb. 2022) 15 Pages.
Seer, Inc. Starting the Proteograph Assay Method, YouTube, May 25, 2021 URL: https://www.youtube.com/watch?v=R94DH7OAOKA.
Seer, Inc. Support Frequently Asked Questions. URL: https://seer.bio/support/faq/ (retrieved online Feb. 2022) 6 Pages.
Seer, Inc. The Challenge in Proteomics Today: Why We Need Unbiased, Deep, Rapid and Scalable Proteomics, YouTube, Mar. 20, 2021, https://www.youtube.com/watch?v=Pq8qbict1dl.
Seer Inc., The proteograph product suite: See the proteome in a way that has never been possible before. Seer.bio. Mar. 2021. Available at: https://seer.bio/resources/document-library/.
Seer, Inc. Unbiased Biomarker Discovery Research with the Porteograph Product Suite, YouTube, Jul. 23, 2021, https://www.youtube.com/watch?v=AodyEDMIdmk.
Seer: Large-scale plasma proteomics with the ProteographTM XT workflow. Seer, Inc., Technical Note (CF-1059 REV A), pp. 1-8 (2023).
Seer Nanoparticle Technology—Brief 1 Minute Overview, YouTube, Mar. 20, 2021, https://www.youtube.com/watch?v=qYFmTuz84IA.
Seer: Proteograph Product Suite: An Automated Workflow that scales with your studies. Seer, Inc., online video presentation available at https://seer.bio/resources/video-gallery/?tx_category=publications&wchannelid=dfl89n6go7&wmediaid=7ac7qj2qpi (2022).
Service, R.F., "Recruiting genes, proteins for a revolution in diagnostics". Science (Apr. 11, 2003), 300:236-239.
Siddiqui, et al., Application of the Proteograph™ Product Suite to the Identification of Differential Protein Isoform Plasma Abundance in Early Lung Cancer vs. Healthy Controls. Seer, Inc. Mar. 2021. 1 Page.
Siddiqui et al.: Deep and Unbiased Plasma Protein Profiling of Alzheimer's and Mild Cognitive Impairment Subjects with a Novel Multi-nanoparticle Approach. Seer, Inc. (Mar. 2022).
Siddiqui et al.: Deep plasma protein profiling in Alzheimer's subjects with a novel unbiased and scalable proteogenomics approach. Seer Inc., Redwood City, CA USA, poster 1 page (2022).
Siddiqui et al.: Large-scale, deep plasma proteomics: An 1800 sample study of Alzheimer's disease. 1. Seer, Inc., Redwood City, CA, USA; and 2. Massachusetts General Hospital, Boston, MA, USA, poster 1 page (2023).
Siddiqui, et al., Plasma Proteomics at Scale Enabling Lung Cancer, Alzheimer's Disease and Proteogenomics Studies with the Proteograph™ Product Suite. Seer, Inc. Mar. 2021. 1 Page.
Silva, Chris, "Small company, big partners—Bethesda-based Correlogic Systems enlists allies in quest to bring its concern detection test to market" Washington Business Journal (Aug. 30-Sep. 5, 2002) 2 pages.
Singh et al., Gene expression correlates of clinical prostate cancer behavior. Cancer Cell. 1(2):203-209 (2002).
Somorjai, R. L., et al., "Class prediction and discovery using gene microarray and proteomics mass spectroscopy data: cruses, caveats, cautions". Bioinfomatrics (2003) 19(12): 1484-1491.
Sorace, James M., et al., "A data review and re-assessment of ovarian cancer serum proteomic profiling". BMC Bioinformatics (2003) 4(24):1-13.
Sorlie et al. Gene expression patterns of breast carcinomas distinguish tumor subclasses with clinical implications. Pnas USA 98:10869-10874 (2001).
Sparano et al.: Prospective Validation of a 21-Gene Expression Assay in Breast Cancer. N Engl J Med. 373(21):2005-2014 doi:10.1056/NEJMoa1510764 (2015).
Srinivas, et al., Proteomics for Cancer Biomarker Discovery. Clinical Chemistry, Aug. 2002; 48(8):1160-1169.
Strittmatter, E. F., et al., "High mass measurement accuracy determination for proteomics using multivariate regression fitting: application to electrospray ionization time-of-flight mass spectrometry". Anal. Chern., (2003), 75(3):460-468.
Stroink, Thorn et al., "On-line coupling of size exclusion and capillary zone electrophoresis via a reversed-phase CI8 trapping column for the analysis of structurally related enkephalines in cerebrospinal fluid". Electrophoresis (2003), 24:897-903.
Stukalov et al.: Dissecting the dynamics of protein corona formation on nanoparticles allows reconstructing deep plasma protein concentrations and discovering novel proteoforms. Seer, Inc., Redwood City, CA, poster 1 page (2023).
Stukalov et al.: Experimental & Computational Approach to Profile Nanoparticle-Protein Interactions for Deep Plasma Proteomics. Seer Inc., Redwood City, CA USA, poster 1 page (2022).
Suhre et al.: Nanoparticle Enrichment Mass-Spectrometry Proteomics Identifies Protein Altering Variants for Precise pQTL Mapping. Cold Spring Harbor Laboratory, bioRxiv pre-print, pp. 1-28. doi:10.1101/2023.04.20.537640 (2023).
Svedberg, Malin et al., "Sheathless Electrospray from Polymer Microchips", Analytical Chemistry, vol. 75, No. 15, Aug. 1, 2003, pp. 3934-3940.
Tan et al.: Multi-dimensional on-particle detection technology for multi-category disease classification. Chem Commun (Camb). 52(17):3490-3493 doi:10.1039/c5cc09419d (2016).

(56) References Cited

OTHER PUBLICATIONS

Tatay, Jacob W., "Multiple approaches to data-mining of proteomic data based on statistical and pattern classification methods". Proteomics (2003) 3: 1704-1709.

Terracciano et al.: Peptidome profiling of induced sputum by mesoporous silica beads and MALDI-TOF MS for non-invasive biomarker discovery of chronic inflammatory lung diseases. Proteomics 11(16):3402-3414 doi:10.1002/pmic.201000828 (2011).

Thompson, Ian M., et al., "Prevalence of Prostate Cancer among Men with a Prostate-Specific Antigen Level 4.0 ng per Milliliter," The New England Journal of Medicine (May 27, 2004) vol. 350 No. 22: 2239-2246.

Tibshirani. Regression shrinkage and selection via the lasso. Journal of the Royal Statistical Society Series B (Methodological) 58:267-288 (1996).

Tihonov, A. N., "Solution of incorrectly formulated problems and the regularization method". Soviet Math. Doklady (1963), 4: 1035-1038.

Tirumalai, Radhakrishna S. et al., "Characterization of the low molecular weight human serum proteome", Molecular & Cellular Proteomics 2.10 (Aug. 13, 2003), 1096-1103.

Tiss et al.: Serum peptide profiling using MALDI mass spectrometry: avoiding the pitfalls of coated magnetic beads using well-established ZipTip technology. Proteomics 7 Suppl 1:77-89 doi:10.1002/pmic.200700746 (2007).

Touchette, Nancy, "Diagnosing Ovarian Cancer by Proteomics". Genome News Network (2003), 3 pages URL: http://www.genomenewsnetwork.org/articles/11_03/ovarian_cancer.shtml.

Trendspotting: Top Diagnostics Issues in 2023. Diagnostics World, pp. 1-4 [retrieved online Jan. 18, 2023 from https://www.diagnosticsworldnews.com/news/2023/01/05/trendspotting-top-diagnostics-issues-in-2023] 2023.

Tuli et al.: LC-MS Based Detection of Differential Protein Expression. J Proteomics Bioinform. 2:416-438 doi:10.4172/jpb.1000102 (2009).

U.S. Appl. No. 17/215,923 Non-Final Office Action dated Feb. 10, 2022.

U.S. Appl. No. 17/215,923 Notice of Allowance dated May 26, 2022.

U.S. Appl. No. 17/215,952 Non-Final Office Action dated May 12, 2022.

U.S. Appl. No. 17/215,978 Final Office Action dated Feb. 22, 2022.

U.S. Appl. No. 17/215,978 Final Office Action dated Jan. 26, 2023.

U.S. Appl. No. 17/216,520 Final Office Action dated Nov. 15, 2021.

U.S. Appl. No. 17/216,523 Final Office Action dated Aug. 30, 2022.

U.S. Appl. No. 17/216,523 Non-Final Office Action dated May 11, 2022.

U.S. Appl. No. 15/388,954 Office Action dated May 15, 2019.

U.S. Appl. No. 16/132,076 Notice of Allowance dated Jul. 2, 2019.

U.S. Appl. No. 16/132,076 Office Action dated Feb. 12, 2019.

U.S. Appl. No. 17/216,520 Office Action dated Aug. 6, 2021.

U.S. Appl. No. 17/216,523 Office Action dated Aug. 17, 2021.

User Guide: Proteograph Product Suite. Seer, Inc. 2021. Available at: https://seer.bio/wp-content/uploads/2021/12/Proteograph_User_Guide_CF-1016-B.pdf.

Vadapalli, et al., Proteograph™ Analysis Suite: A cloud-scalable software suite for proteogenomics data analysis and visualization. Seer, Inc. Nov. 2021. 1 Page.

Valko et al.: Learning predictive models for combinations of heterogeneous proteomic data sources. AMIA Summit on Translational Bioinformatics, 5 pages. HAL0064339 Url: https://hal.inria.fr/hal-00643349 (2008).

Van Holten et al.: Circulating biomarkers for predicting cardiovascular disease risk; a systematic review and comprehensive overview of meta-analyses. PLoS One 8(4):e62080:1-8 doi:10.1371/journal.pone.0062080 (2013).

Van Hong Nguyen, et al. Protein corona: a new approach for nanomedicine design. International journal of nanomedicine 12 (Apr. 18, 2017): 3137-3151.

Van't Veer et al. Gene expression profiling predicts clinical outcome of breast cancer. Nature 415(6871):530-536 (2002).

Vejda, Susanne, et al., "Plasma from Cancer Patients Featuring a Characteristic Protein Composition Mediates Protection against Apoptosis," Molecular & Cellular Proteomics (2002):387-393.

Velstra et al.: Improved classification of breast cancer peptide and protein profiles by combining two serum workup procedures. J Cancer Res Clin Oncol. 138(12):1983-1992 doi:10.1007/s00432-012-1273-4 (2012).

Venkataraman et al.: Assessment of pQTL method performance reveals optimal proteogenomic approach to assess the impact of genetic variation on plasma protein levels. Seer, Inc., Redwood City, CA; and Massachusetts General Hospital, Boston, MA. poster 1 page (2023).

Villanueva et al.: Automated serum peptide profiling. Nat Protoc. 1(2):880-891 doi:10.1038/nprot.2006.128 (2006).

Villanueva et al.: Differential exoprotease activities confer tumor-specific serum peptidome patterns. J Clin Invest. 116(1):271-284 doi:10.1172/JCI26022 (2006).

Villanueva, Josep et al., "Serum peptide profiling by magnetic particle-assisted, automated sample processing and MALDI-TOF mass spectrometry". Anal. Chern. (Mar. 15, 2004), 76(6): 1560-1570.

Vlahou, Antonia, et al., "Development of a novel proteomic approach for the detection of transitional cell carcinoma of the bladder in urine". American Journal of Pathology (Apr. 2001), 158(4): 1491-1502.

Vohradsky, J., "Adaptive classification of two-dimensional gel electrophoretic spot patterns by neural networks and cluster analysis". Electrophoresis (1997), 18:2749-2754.

Wang et al.: Building Spectral Libraries for Large-Scale Quantitative Proteomic Studies in Human Plasma. 1. Seer, Inc., Redwood City, CA; and 2. Weill Cornell Medicine-Qatar, Doha, State of Qatar, poster 1 page (2023).

Wang, Michael Z. et al., "Analysis of human serum proteins by liquid phase isoelectric focusing and matrix-assisted laser desorption/ionization-mass spectrometry", Proteomics (2003), 3:1661-1666.

Ward, A. Milford, et al., "Acute Phase Reactant proteins in Prostatic Cancer," British Journal of Urology (1977), 49: 411-418.

Westmeier et al.: The bio-corona and its impact on nanomaterial toxicity. European Journal of Nanomedicine 7(3):153-168 https://doi.org/10.1515/ejnm-2015-0018 (2015).

Whiteaker, Jeffrey R et al. An automated and multiplexed method for high throughput peptide immunoaffinity enrichment and multiple reaction monitoring mass spectrometry-based quantification of protein biomarkers. Molecular & cellular proteomics : MCP vol. 9,1 (2010): 184-96. doi:10.1074/mcp.M900254-MCP200.

Wilcox et al.: A large scale multi-cancer, multi-omics biomarker study of 1,800 subjects incorporating deep unbiased plasma proteomics. PrognomiQ Inc. San Mateo, CA, poster 1 page (2022).

Wilcox et al.: Deep, unbiased multi-omics approach for the identification of pancreatic cancer biomarkers from blood. PrognomiQ, San Mateo, California, USA, poster 1 page (2022).

Wilcox et al.: Incorporation Of Glycoproteome Detection Into Large Scale Unbiased Proteomics Studies Utilizing Nanoparticles. PrognomiQ Inc. (Mar. 2022).

Williams, Jon D., et al., "Using accurate mass electrospray ionization-time-of-flight mass spectrometry with in-source collision-induced dissociation to sequence peptide mixtures". Journal of Chromatography A (2003) 1020: 11-26.

Wilson, et al., The utility of nanoparticle protein coronas for studying the plasma glycoproteome. Seer, Inc. Nov. 2021. 1 Page.

Wittke, Stefan et al., "Determination of peptides and proteins in human urine with capillary electrophoresis-mass spectrometry, a suitable tool for the establishment of new diagnostic markers". Journal of Chromatography A (2003), 1013: 173-181.

Wright et al. Proteinchip surface enhanced laser desorption/ionization (SELDI) mass spectrometry: a novel protein biochip technology for detection of prostate cancer biomarkers in complex protein mixtures. Prostate Cancer and Prostatic Diseases. 1999;2(5/6):264-276.

(56) References Cited

OTHER PUBLICATIONS

Wu, Baolin et al., "Comparison of statistical methods for classification of ovarian cancer using mass spectrometry data", Bioinformatics (2003) 19(13):1636-1643.
Wu, Shiaw-Lin, et al., "Targeted proteomics of low-level proteins in human plasma by LC/MSn: Using human growth hormone as a model system". Journal ofProteome Research (2002):459-465.
Xue et al.: Quantifying thiol-gold interactions towards the efficient strength control. Nat Commun 5:4348:1-8 doi:10.1038/ncomms5348 (2014).
Yanagisawa, Kiyoshi, et al., "Proteomic patterns of tumour subsets in non-small-cell lung cancer". The Lancet (Aug. 9, 2003), 362:433-439.
Yang et al.: Proteomic Profiling of Invasive Ductal Carcinoma (IDC) using Magnetic Beads-based Serum Fractionation and MALDI-TOF MS. J Clin Lab Anal. 29(4):321-327 doi:10.1002/jcla.21773 (2015).
Yang et al.: Serum peptidome profiling in patients with gastric cancer. Clin Exp Med. 12(2):79-87 doi:10.1007/s10238-011-0149-2 (2012).
Yasui, Yataka, et al., "A data-analytic strategy for protein biomarker discovery: profiling of high-dimensional proteomic data for cancer detection". Biostatistics (2003) 4(3):449-463.
Zamanighomi et al.: Deep and Untargeted Plasma Protein Profiling of Alzheimer's Subjects with a Novel Multi-nanoparticle Approach. Seer, Inc., Redwood City, CA, online video available at URL: https://seer.bio/resources/video-gallery/?tx_category=publications&wchannelid=dfl89n6go7&wmediaid=64xoqf4r2m (2022).
Zamanighomi et al.: Deep Plasma Proteomics at Scale Enabling Precision Analyses in a Lung Cancer (NSCLC) Study. Seer, Inc., Redwood City, CA, poster 1 page (2022).
Zhang et al.: Evaluation of a novel, integrated approach using functionalized magnetic beads, bench-top MALDI-TOF-MS with prestructured sample supports, and pattern recognition software for profiling potential biomarkers in human plasma. J Biomol Tech. 15(3):167-175 (2004).
Zhang et al.: Integrated Proteogenomic Characterization of Human High-Grade Serous Ovarian Cancer. Cell 166(3):755-765 doi:10.1016/j.cell.2016.05.069 (2016).
Zhang, Zhen, et al., "Three Biomarkers Identified from Serum Proteomic Analysis for the Detection of Early Stage Ovarian Cancer," Cancer Research (Aug. 15, 2004) 64:5882-5890.
Zhao, et al., Evaluation of Cell-Free DNA blood plasma for unbiased, deep, and rapid proteomics analysis enabling large-scale studies. Seer, Inc. Mar. 2021. 1 Page.
Zhi et al. Multianalyte Immunoassay with Self-Assembled Addressable Microparticle Array on a Chip. Analytical Biochemistry 318:236-243 (2003).
Zhou et al.: Multi-omics data integration reveals clinically relevant biomolecules associated with type 2 diabetes. 1. Seer, Inc., Redwood City, CA; and 2. Weill Cornell Medicine-Qatar, Doha, State of Qatar, poster 1 page (2022).
Zhu, Hongtu, et al. "Tree-based disease classification using protein data". Proteomics (2003) 3:1673-1677.
Zhu, Wei, et al. "Detection of cancer-specific markers amid massive mass spectral data". PNAS (Dec. 9, 2003) 100(25):14666-14761.
Zou et al.: Synthesis and evaluation of superparamagnetic silica particles for extraction of glycopeptides in the microtiter plate format. Anal Chem. 80(4):1228-1234 doi:10.1021/ac701950h (2008).
Batth, Tanveer S et al. Protein Aggregation Capture on Microparticles Enables Multipurpose Proteomics Sample Preparation. Molecular & cellular proteomics : MCP vol. 18,5 (2019): 1027-1035. doi:10.1074/mcp.TIR118.001270.
Boca Scientific. Magtivio. MagSi-Tools 600, 1.0, 3.0 Product Description: pp. 1-2.
Hughes, Christopher S et al. Single-pot, solid-phase-enhanced sample preparation for proteomics experiments. Nature protocols vol. 14,1 (2019): 68-85. doi:10.1038/s41596-018-0082-x.
Hughes, Christopher S et al. Ultrasensitive proteome analysis using paramagnetic bead technology. Molecular systems biology vol. 10,10 (2014): 757. doi: 10.15252/msb.20145625.
Magtivio B.V. MagSiMUS and MagSi Product Catalog. Magnetic Separation Solutions (2018).
Resyn Biosciences (Pty) Ltd. MagReSyn® SAX Strong anion exchange magnetic microparticles: pp. 1-2. Retrieved online on Jun. 4, 2023 available at https://resynbio.com/wp-content/uploads/2020/IFU_SAX.pdf.
Sielaff, Malte et al. Evaluation of FASP, SP3, and iST Protocols for Proteomic Sample Preparation in the Low Microgram Range. Journal of proteome research vol. 16,11 (2017): 4060-4072. doi:10.1021/acs.jproteome.7b00433.
Jang, J.H., Characterization and analytical application of surface modified magnetic nanoparticles. Microchemical journal. 94 (2010): 148-158.
Agasti et al. (Adv. Drug Deliv Rev. Mar. 8, 2010; 62(3):316-328) (Year: 2010).
Aggarwal, P., Hall, J.B., Mcleland, C.B., Dobrovolskaia, M.A. & McNeil, S.E. Nanoparticle interaction with plasma proteins as it relates to particle biodistribution, biocompatibility and therapeutic efficacy. Advanced drug delivery reviews 61, 428-437 (2009).
Ahn, J.-M. & Cho, J.-Y. Current serum lung cancer biomarkers. Journal of Molecular Biomarkers & Diagnosis 2013 (2013).
Alexopoulos, C., Blatsios, B. & Avgerinos, A. Serum lipids and lipoprotein disorders in cancer patients. Cancer 60, 3065-3070 (1987).
Alexopoulos, C., Pournaras, S., Vaslamatzis, M., Avgerinos, A. & Raptis, S. Changes in serum lipids and lipoproteins in cancer patients during chemotherapy. Cancer chemotherapy and pharmacology 30, 412-416 (1992).
Ali, et al. "Erlotinib-Conjugated Iron Oxide Nanoparticles as a Smart Cancer-Targeted Theranostic Probe for MRI." Scientific reports vol. 6 36650. Nov. 11, 2016, doi:10.1038/srep36650.
Amici, A. et al. In vivo protein corona patterns of lipid nanoparticles. RSC Advances 7, 1137-1145 (2017).
Andersen, J.D. et al. Identification of candidate biomarkers in ovarian cancer serum by depletion of highly abundant proteins and differential in-gel electrophoresis. Electrophoresis 31, 599-610(2010).
Anderson, L. Candidate-Based Proteomics in the Search for Biomarkers of Cardiovascular Disease. The Journal of physiology 2005, 563, 23-60.
Angel, T.E. et al. Mass spectrometry-based proteomics: existing capabilities and future directions. Chemical Society Reviews 41, 3912-3928 (2012).
Ashby et al., Size and surface functionalization of iron oxide nanoparticles influence the composition and dynamic nature of their protein corona. ACS Appl. Mater. Interfaces 2014, 6, p. 15412-15419.
Askim, J. R., Mahmoudi, M. & Suslick, K. S. Optical sensor arrays for chemical sensing: the optoelectronic nose. Chemical Society Reviews 42, 8649-8682 (2013).
Bagalkot, V. et al. Quantum dot-aptamer conjugates for synchronous cancer imaging, therapy, and sensing of drug delivery based on bi-fluorescence resonance energy transfer. Nano letters 7, 3065-3070 (2007).
Bakhtiary, Z. et al. Targeted superparamagnetic iron oxide nanoparticles for early detection of cancer: Possibilities and challenges. Nanomedicine: Nanotechnology, Biology and Medicine 12, 287-307 (2016).
Bally, M., et al. "Liposome and lipid bilayer arrays towards biosensing applications." Small 6.22 (2010): 2481-2497.
Barran-Berdon, et al., Time Evolution of Nanoparticle-Protein corona in Human Plasma: Relevance for targeted drug delivery. Langmuir, 2013, 29, 6485-6494.
Beck, H.C., Overgaard, M. & Rasmussen, L.M. Plasma proteomics to identify biomarkers-application to cardiovascular diseases. Translational Proteomics 7, 40-48 (2015).
Beri, J., Rosenblatt, M.M., Strauss, E., Urh, M. & Bereman, M.S. Reagent for Evaluating Liquid Chromatography13 Tandem Mass Spectrometry (LC-MS/MS) Performance in Bottom-Up Proteomic Experiments. Analytical chemistry 87, 11635-11640 (2015).

(56) References Cited

OTHER PUBLICATIONS

Bertrand, N., et al. Mechanistic understanding of in vivo protein corona formation on polymeric nanoparticles and impact on pharmacokinetics. Nat Commun 8, 777 (2017).
Bigdeli et al. "Exploring cellular interactions in liposomes using protein corona fingerprints and physicochemical properties", ACS Nano, 10(3): 3723-3737 (2016).
BIO-RAD, ProteoMinerTM Protein Enrichment Technology [Online] Available at: http://wolfson.huji.ac.il/purification/PDF/AlbuminRemoval/BIORAD_ProteoMiner.pdf. [Accessed Sep. 17, 2020].
Bisker, et al. Protein-targeted corona phase molecular recognition. Nat Commun 7, 10241 (2016). https://doi.org/10.1038/ncomms10241.
Bloom, D., Cafiero, E., Jane-Llopis, E., et al. The Global Economic Burden of Noncommunicable Diseases. Program on the Global Demography of Aging;2012.
Bloomston, M. et al. Fibrinogen γ overexpression in pancreatic cancer identified by large-scale proteomic analysis of serum samples. Cancer research 66, 2592-2599 (2006).
Blume, et al., Analytical validation of the multi-nanoparticle proteograph platform for rapid and deep proteomic profiling. Seer, Inc. Apr. 2020. 1 Page.
Blume, et al., Efficient and scalable profiling of a median of 1,779 plasma proteins in 288 subjects with multi-nanoparticle (NP) proteograph platform enables robust detection of early-stage non-small cell lung cancer (NSCLC) and classification vs. healthy and co-morbid subjects. Seer, Inc. Apr. 2020. 1 Page.
Blume, et al., Proteograph, a novel multi-nanoparticle platform, enables rapid and deep proteomics profiling, significantly improving coverage, throughput, and scalability versus existing methods. Seer, Inc. Jun. 2020. 1 Page.
Blume, et al., Rapid, deep and precise profiling of the plasma proteome with multi-nanoparticle protein corona. Nat Commun 11, 3662; 1-14 (2020). https://doi.org/10.1038/s41467-020-17033-7.
Bodansky, O. & Mcinnes, G. F. Thermal coagulation of serum proteins in cancer, in the postoperative phase of surgery, and in the administration of adrenocorticotropic hormone. Cancer 3, 1-14 (1950).
Brede et al., Applications of Nanoparticles in the Detection and Treatment of Kidney Diseases, Advances in Chronic kidney disease, vol. 20, Issue 6, Nov. 2013, pp. 454-465.
Breiman, L. Random forests. Machine learning 45, 5-32 (2001).
Brenner, et al., Gene Expression analysis by massively parallel signature sequencing (MPSS) on microbead arrays. Nature Biotechnology 18.6 (Jun. 2000): 630-634, doi:10.1038/76469.
Byrne, J.C. et al. 2D-DIGE as a strategy to identify serum markers for the progression of prostate cancer. Journal of proteome research 8, 942-957 (2008).
Cao, Z., Tang, H.-Y., Wang, H., Liu, Q. & Speicher, D.W. Systematic comparison of fractionation methods for in-depth analysis of plasma proteomes. J Proteome Res 11, 3090-3100 (2012).
Capriotti, A.L. et al. Label-free quantitative analysis for studying the interactions between nanoparticles and plasma proteins. Analytical and bioanalytical chemistry 405, 635-645 (2013).
Capriotti et al., Shotgun proteomic analytical approach for studying proteins adsorbed onto liposome surface, Anal Bioanal Chem, 2011, 401, 1195-1202.
Caputo, et al. A protein corona-enabled blood test for early cancer detection. Nanoscale 9.1 (Jan. 7, 2017): 349-354.
Caracciolo, et al., Evolution of the protein corona of lipid gene vectors as a function of plasma concentration. Langmuir, 2011, 27, 15048-15053.
Caracciolo, G., Caputo, D., Pozzi, D., Colapicchioni, V. & Coppola, R. Size and charge of nanoparticles following incubation with human plasma of healthy and pancreatic cancer patients. Colloids and Surfaces B: Biointerfaces 123, 673-678 (2014).
Caracciolo, G., et al. Lipid composition: a "key factor" for the rational manipulation of the liposome-protein corona by liposome design. RSC Adv 5, 5967-5975 (2015).
Caracciolo, G., Farokhzad, O.C. & Mahmoudi, M. Biological Identity of Nanoparticles In Vivo: Clinical Implications of the Protein Corona. Trends in Biotechnology 35, 257-264 (2017).
Carey, J. R et al. Rapid identification of bacteria with a disposable colorimetric sensing array. Journal of the American Chemical Society 133, 7571-7576 (2011).
Carter, A. M. Complement Activation: An Emerging Player in the Pathogenesis of Cardiovascular Disease. Scientifica 2012, 2012.
Carter, H. B. et al. Early detection of prostate cancer: AUA Guideline. The Journal of urology 190, 419-426 (2013).
Cedervall, T., et al. Understanding the nanoparticle-protein corona using methods to quantify exchange rates and affinities of proteins for nanoparticles. Proc Natl Acad Sci U S A 104, 2050-2055 (2007).
Cerasoli, E. et al. MiS-MALDI: microgel-selected detection of protein biomarkers by MALDI-TOF mass spectrometry. Molecular Biosystems 6, 2214-2217 (2010).
Choi, Y.-E., Kwak, J.-W. & Park, J. W. Nanotechnology for early cancer detection. Sensors 10, 428-455 (2010).
Clemments, A. M. et al., Protein Adsorption From Biofluids on Silica Nanoparticles: Corona Analysis as a Function of Particle Diameter and Porosity, ACS Applied Materials & Interfaces 2015, 7, 21682-21689, with 5 pages of supporting information.
Colapicchioni, V. et al. Personalized liposome-protein corona in the blood of breast, gastric and pancreatic cancer patients. International Journal of Biochemistry and Cell Biology, 2015,75(11): 180-187.
Consortium, E.P. Europe PMC: a full-text literature database for the life sciences and platform for innovation. Nucleic acids research, gku1061 (2014).
Corbo, C. et al., Biomarker discovery by proteomics-based approaches for early detection and personalized medicine in colorectal cancer, Proteomics—Clinical Applications, 2017, 11, 5-6, paper 1600072, 19 pages.
Corbo, C. et al. Unveiling the in Vivo Protein Corona of Circulating Leukocyte-like Carriers. ACS Nano (2017).
Corbo, C., Molinaro, R., Parodi, A., Furman, N. E. T., Salvatore, F., Tasciotti, E. The Impact of Nanoparticle Protein Corona on Cytotoxicity, Immunotoxicity and Target Drug Delivery. Nanomedicine 2016, 11, 81-100.
Corbo, C., Molinaro, R., Tabatabaei, M., Farokhzad, O.C. & Mahmoudi, M. Personalized protein corona on nanoparticles and its clinical implications. Biomater Sci 5, 378-387 (2017).
Corbo, et al. Effects of the protein corona on liposome-liposome and liposome-cell interactions. Int J Nanomedicine. 2016; 11: 3049-3063. Published online Jul. 4, 2016. doi: 10.2147/IJN.S109059.
Croft, D. et al. The Reactome pathway knowledgebase. Nucleic acids research 42, D472-D477 (2013).
Cruz, J.A. & Wishart, D.S. Applications of machine learning in cancer prediction and prognosis. Cancer informatics 2, 59 (2006).
Cuenca, A.G. et al. Emerging implications of nanotechnology on cancer diagnostics and therapeutics. Cancer 107, 459-466 (2006).
Cuzick, J. et al. Prevention and early detection of prostate cancer. The Lancet Oncology 15, e484-e492, doi: 10.1016/ S1470-2045(2014)70211-6.
Del Pino, et al. Protein corona formation around nanoparticles—from the past to the future. Maler Horiz, 2014, 1, 301.
Deng, Y., Qi, D., Deng, C., Zhang, X. & Zhao, D. Superparamagnetic high-magnetization microspheres with an Fe3O4@SiO2 core and perpendicularly aligned mesoporous SiO2 shell for removal of microcystins. J Am Chem Soc 130, 28-29 (2008).
Deng, Z.J., Liang, M., Monteiro, M., Toth, I. & Minchin, R.F. Nanoparticle-induced unfolding of fibrinogen promotes Mac-1 receptor activation and inflammation. Nature nanotechnology 6, 39-44 (2011).
Deng, Z.J., Liang, M., Toth, I., Monteiro, M.J. & Minchin, R.F. Molecular interaction of poly (acrylic acid) gold nanoparticles with human fibrinogen. ACS nano 6, 8962-8969 (2012).
Di Domenico, M. et al., Nanoparticle-biomolecular corona: A new approach for the early detection of non-small-cell lung cancer. Journal of Cellular Physiology 2019, 234, 9378-9386.
Di Silvio, D. et al., Technical tip: high-resolution isolation of nanoparticle-protein corona complexes from physiological fluids, Nanoscale, 2015, 7, 11980-11990, with 7 pages of supplementary information.

(56) References Cited

OTHER PUBLICATIONS

Digiacomo, L. et al., A protein corona sensor array detects breast and prostate cancers, Nanoscale 2020, 12, 16697-16704.
Dobrovolskaia et al., Protein corona composition does not accurately predict hematocompatibility of colloidal gold nanoparticles, Nanomedicine: Nanotechnology, Biology, and Medicine, 2014, 10:1453-1463.
Docter, D., et al. Quantitative profiling of the protein coronas that form around nanoparticles. Nat Protoc 9, 2030-2044 (2014).
Docter, et al. The nanoparticle biomolecule corona: lessons learned-challenge accepted?. Chemical Society Reviews 44.17 (2015): 6094-6121.
Dyna beads Products & Technology. ThennoFisher Scientific, Website accessed Dec. 15, 2021 at https://www.thermofisher.com/us/en/home/brands/product-brand/dynal/dynabeads-technology.html.
Einav, S. et al. Early postoperative serum S10013 levels predict ongoing brain damage after meningioma surgery: a prospective observational study. Critical Care 10, 1 (2006).
Elechalawar, C. K. et al., Analysing the nanoparticle-protein corona for potential molecular target identification, Journal of Controlled Release Jun. 10, 2020, 322, 122-136.
Enroth, S., Hallmans, G., Grankvist, K. & Gyllensten, U. Effects of long-term storage time and original sampling month on biobank plasma protein concentrations. EBioMedicine 12, 309-314 (2016).
Enten, A. et al., A Liquid-Handling Robot for Automated Attachment of Biomolecules to Microbeads, Journal of Laboratory Automation 2016, 21, 526-532.
EP17881767.2 Extended European Search Report dated Jul. 22, 2020.
Etzioni, R. et al. The case for early detection. Nature Reviews Cancer 3, 243-252 (2003).
Everley, et al., Proteograph: Efficient and automated multi-nanoparticle platform for Deep, Unbiased Plasma protein profiling and protein-protein interaction biological insight. Seer, Inc. Mar. 2020.
Faca, V. M. et al. A mouse to human search for plasma proteome changes associated with pancreatic tumor development. PLoS Med 5, e123 (2008).
Farokhzad, 0. C. et al. Targeted nanoparticle-aptamer bioconjugates for cancer chemotherapy in vivo. Proceedings of the National Academy of Sciences 103, 6315-6320 (2006).
Farrah, T., et al. A high-confidence human plasma proteome reference set with estimated concentrations in PeptideAtlas. Mol Cell Proteomics 10, M110 006353 (2011).
Feldman, E. B. & Carter, A. C. Circulating lipids and lipoproteins in women with metastatic breast carcinoma. The Journal of Clinical Endocrinology & Metabolism 33, 8-13 (1971 ).
Ferguson, M. K. et al. Sex-associated differences in survival of patients undergoing resection for lung cancer. The Annals of thoracic surgery 69, 245-249 (2000).
Ferrari, M. Cancer nanotechnology: opportunities and challenges. Nature Reviews Cancer 5, 161-171 (2005).
Fodor, S.P. et al., Light-directed, spatially addressable parallel chemical synthesis. Science, 251 (4995), 767-773 (1991).
Fontana, R. S. et al. Early Lung Cancer Detection: Results of the Initial (Prevalence) Radiologic and Cytologic Screening in the Mayo Clinic Study 1, 2. American Review of Respiratory Disease 130, 561-565 (1984).
Forbes, et al. COSMIC: exploring the world's knowledge of somatic mutations in human cancer. Nucleic Acids Res. Jan. 2015;43 (Database issue): D805-D811. Epub Oct. 29, 2014.
Fortunato, J. E., Bassiouny, H. S., Song, R.H., et al. Apolipoprotein (a) Fragments in Relation to Human Carotid Plaque Instability. Journal of vascular surgery 2000, 32, 555-563.
Gabizon, A. et al. Cancer nanomedicines: closing the translational gap. The Lancet 384, 2175-2176 (2014).
Gao, W.-M. et al. Distinctive serum protein profiles involving abundant proteins in lung cancer patients based upon antibody microarray analysis. BMC cancer 5, 1 (2005).

Gautam, P. et al. Proteins with altered levels in plasma from glioblastoma patients as revealed by iTRAQ-based quantitative proteomic analysis. PloS one 7, e46153 (2012).
Ghasemi, F., Hormozi-Nezhad, M. R. & Mahmoudi, M. Identification of catecholamine neurotransmitters using fluorescence sensor array. Analytica Chimica Acta 917, 85-92 (2016).
Ghavami, M. et al. Plasma concentration gradient influences the protein corona decoration on nanoparticles. Rsc Advances 3, 1119-1126 (2013).
Gopal, K., Grossi, E., Paoletti, P. & Usardi, M. Lipid composition of human intracranial tumors: A biochemical study. Acta neurochirurgica 11, 333-34 7 (1963).
Gossmann, R. et al., Comparative examination of adsorption of serum proteins on HSA- and PLGA-based nanoparticles using SDS-PAGE and LC-MS, European Journal of Pharmaceutics and Biopharmaceutics 2015, 93, 80-87.
Guo, D. et al. An LXR agonist promotes glioblastoma cell death through inhibition of an EGFR/AKT/SREBP-1/LDLR—dependent pathway. Cancer discovery (2011 ).
Guo, D. et al. EGFR signaling through an Akt-SREBP-1-dependent, rapamycin-resistant pathway sensitizes glioblastomas to antilipogenic therapy. Science signaling 2, ra82 (2009).
Guo, D. et al. The AMPK agonist AICAR inhibits the growth of EGFRvIII-expressing glioblastomas by inhibiting lipogenesis. Proceedings of the National Academy of Sciences 106, 12932-12937 (2009).
Guo, Q. et al. Elevated levels of plasma fibrinogen in patients with pancreatic cancer: possible role of a distant metastasis predictor. Pancreas 38, e75-e79 (2009).
Gupta, A. et al. Synergistic antimicrobial therapy using nanoparticles and antibiotics for the treatment of multidrug-resistant bacterial infection. Nano Futures 1, 015004 (2017).
Hadjidemetriou, et al., A novel scavenging tool for cancer biomarker discovery based on the blood-circulating nanoparticle protein corona. Biomaterials. Jan. 2019; vol. 188: pp. 118-129.
Hadjidemetriou, et al., In Vivo Biomolecule Corona around Blood-Circulating, Clinically Used and Antibody-Targeted Lipid Bilayer Nanoscale Vesicles. ACS Nano, 2015; 9(8): pp. 8142-8156.
Hadjidemetriou, et al., The Human In Vivo Biomolecule Corona onto PEGylated Liposomes: A Proof-of-Concept Clinical Study. Advanced Materials. Nov. 28, 2018:e1803335. doi: 10.1002/adma.201803335. [Epub ahead of print].
Hadjidemetriou, M., Al-Ahmady, Z. & Kostarelos, K. Time-evolution of in vivo protein corona onto blood-circulating PEGylated liposomal doxorubicin (DOXIL) nanoparticles. Nanoscale 8, 6948-6957 (2016).
Hajipour et al., Personalized disease-specific protein corona influences the therapeutic impact of graphene oxide, Nanoscale. 7(19):8978-8994 (2015) (pre-print).
Hajipour, et al., Personalized protein coronas: a "key" factor at the nanobiointerface. Biomate Sci. 2014; 2: 1210-1221.
Hajipour, M. J. et al. Personalized disease-specific protein corona influences the therapeutic impact of graphene oxide. Nanoscale, 2015, 7(19): 8978-8994.
Hajipour, M. J. et al., Sensing of Alzheimer's Disease and Multiple Sclerosis Using Nano-Bio Interfaces, Journal of Alzheimer's Disease 2017, 59, 1187-1202.
Hanash, S. M., Pitteri, S. J. & Faca, V. M. Mining the plasma proteome for cancer biomarkers. Nature 452, 571-579 (2008).
Hansson, G. K., Hermansson, A. The Immune System in Atherosclerosis. Nature immunology 2011, 12, 204-212.
Hasija, K. & Bagga, H. K. Alterations of serum cholesterol and serum lipoprotein in breast cancer of women. Indian Journal of Clinical Biochemistry 20, 61-66 (2005).
Hassanein, M. et al. The state of molecular biomarkers for the early detection of lung cancer. Cancer prevention research 5, 992-1006 (2012).
Heath, J. R. & Davis, M. E. Nanotechnology and cancer. Annual review of medicine 59, 251 (2008).
Henschke, C. I. et al. Early Lung Cancer Action Project: overall design and findings from baseline screening. The Lancet 354, 99-105 (1999).

(56) References Cited

OTHER PUBLICATIONS

Hirsch, F. R., Franklin, W. A., Gazdar, A. F. & Bunn, P. A. Early detection of lung cancer: clinical perspectives of recent advances in biology and radiology. Clinical Cancer Research 7, 5-22 (2001).

Honda, K. et al. Plasma biomarker for detection of early stage pancreatic cancer and risk factors for pancreatic malignancy using antibodies for apolipoprotein-AI I isoforms. Scientific reports 5 (2015).

Howlader N. et al. SEER Cancer Statistics Review, 1975-2014, National Cancer Institute. Bethesda, MD, https://seer. cancer.gov/csr/1975_2014/, based on Nov. 2016 SEER data submission, posted to the SEER web site, Apr. 2017. (2017).

Huang, et al. "Superparamagnetic iron oxide nanoparticles conjugated with folic acid for dual target-specific drug delivery and MRI in cancer theranostics" Mater Sci Eng C Mater Biol Appl. Jan. 1, 2017;70(Pt1) 763-771. doi: 10.1016/j.msec.2016.09.052.

Huggins, C., Miller, G. M. & Jensen, E. V. Thermal Coagulation of Serum Proteins II. Deficient Coagulation in Cancer and the Iodoacetate Index. Cancer Research 9, 177-182 (1949).

Huo, Q. et al., A facile nanoparticle immunoassay for cancer biomarker discovery. Journal of Nanobiotechnology 2011, 9, paper 20, 12 pages.

Hwang, T. L., Liang, Y., Chien, K. Y. & Yu, J. S. Overexpression and elevated serum levels of phosphoglycerate kinase 1 in pancreatic ductal adenocarcinoma. Proteomics 6, 2259-2272 (2006).

Jaffe, A. S., Babuin, L., Apple, F. S. Biomarkers in Acute Cardiac Disease. Journal of the American College of Cardiology 2006, 48, 1-11.

Jager et al., Investigation of Arsenic-Stressed Yeast (*Saccharomyces cerevisiae*) as a Bioassay in Homeopathic Basic Research, Scientific World Journal; 2011; vol. 11, pp. 568-583, Published online Mar. 7, 2011.

Jankovska, et al. Affinity depletion versus relative protein enrichment: a side-by-side comparison of two major strategies for increasing human cerebrospinal fluid proteome coverage. Clin Proteom, 2019; 16(9):1-10. https://doi.org/10.1186/s12014-019-9229-1.

Jayaram, S., Gupta, M. K., Polisetty, R. V., Cho, W. C. & Sirdeshmukh, R. Towards developing biomarkers for glioblastoma multiforme: a proteomics view. Expert review of proteomics 11, 621-639 (2014).

Jerant, A. F., Johnson, J. T., Sheridan, C. & Caffrey, T. J. Early detection and treatment of skin cancer. American family physician 62, 357-386 (2000).

Jung, et al., Specific colorimetric detection of proteins using bidentate aptamer-conjugated polydiacetylene (PDA) liposomes, Adv Funct. Mater, 2010, vol. 20, No. 8 pp. 3092-3097.

Karna, E. et al. Serum and tissue level of insulin-like growth factor-I (IGF-1) and IGF-1 binding proteins as an index of pancreatitis and pancreatic cancer. International journal of experimental pathology 83, 239-246 (2002).

Kawasaki, E. S. & Player, A. Nanotechnology, nanomedicine, and the development of new, effective therapies for cancer. Nanomedicine: Nanotechnology, Biology and Medicine 1, 101-109 (2005).

Keshishian, et al., Quantitative, multiplexed workflow for deep analysis of human blood plasma and biomarker discovery by mass spectrometry, Nat Protoc, 2017 12, 8, 1683-1701.

Keshishian, H., Addona, T., Burgess, M., Kuhn, E. & Carr, S.A. Quantitative, multiplexed assays for low abundance proteins in plasma by targeted mass spectrometry and stable isotope dilution. Molecular & Cellular Proteomics 6, 2212-2229 (2007).

Keshishian, H. et al. Quantification of cardiovascular biomarkers in patient plasma by targeted mass spectrometry and stable isotope dilution. Molecular & cellular proteomics 8, 2339-2349 (2009).

Kharya, S., Dubey, D. & Soni, S. Predictive Machine Learning Techniques for Breast Cancer Detection. (IJCSIT) International Journal of Computer Science and Information Technologies 4, 1023-1028 (2013).

Konduru et al., Protein Corona: Implications for Nanoparticle Interactions with Pulmonary Cells, Particle and Fibre Toxicology, 2017, 14:42, pp. 1-12.

Korbelik, M. & Cooper, P. Potentiation of photodynamic therapy of cancer by complement: the effect of γ-inulin. British journal of cancer 96, 67-72 (2007).

Koscielny, G. et al. Open Targets: a platform for therapeutic target identification and validation. Nucleic acids research 45, D985-D994 (2016).

Kourou, K., Exarchos, T.P., Exarchos, K.P., Karamouzis, M.V. & Fotiadis, D.I. Machine learning applications in cancer prognosis and prediction. Computational and structural biotechnology journal 13, 8-17 (2015).

Kugler, K.G. et al. The impact of sample storage time on estimates of association in biomarker discovery studies. Journal of clinical bioinformatics 1, 1 (2011).

Lacerda, S.H.D.P., et al. Interaction of gold nanoparticles with common human blood proteins. ACS Nano 4, 365-379 (2009).

Laurent, S. et al. Corona protein composition and cytotoxicity evaluation of ultra-small zeolites synthesized from template free precursor suspensions. Toxicology Research 2, 270-279 (2013).

Laurent, S. et al., Superparamagnetic iron oxide nanoparticles: promises for diagnosis and treatment of cancer. Int J Mol Epidemiol Genet. 2011; 2(4): 367-390. Published online Nov. 25, 2011.

Le, N. D., Yazdani, M., Rotello, V. M. Array-Based Sensing Using Nanoparticles: An Alternative Approach for Cancer Diagnostics. Nanomedicine 2014, 9, 1487-1498.

Lee et al., Recognition of Volatile Organic Compounds Using $SnO_2$ Sensor Array and Pattern Recognition Analysis. Sensors and Actuators B: Chemical, Jun. 2001, 77, 228-236.

Lee, G. Cancerous immunoglobulins in cancer immunology. Journal of Clinical & Cellular Immunology 2014.

Levin, B. et al. Screening and surveillance for the early detection of colorectal cancer and adenomatous polyps, 2008: a joint guideline from the American Cancer Society, the US Multi-Society Task Force on Colorectal Cancer, and the American College of Radiology*t. CA: a cancer journal for clinicians 58, 130-160 (2008).

Li et al. A review on phospholipids and their main applications in drug delivery systems. Asian Journal of Pharmaceutical Sciences 10:81-98 (2015).

Lim, S. H., Feng, L., Kemling, J. W., Musto, C. J. & Suslick, K. S. An optoelectronic nose for the detection of toxic gases. Nature chemistry 1, 562-567 (2009).

Lin, et al. A chemically functionalized magnetic nanoplatform for rapid and specific biomolecular recognition and separation Biomacromolecules 2013, 14, 1, 160-168.

Lin Jiang et al: "Patterning of Plasmonic Nanoparticles into Multiplexed One-Dimensional Arrays Based on Spatially Modulated Electrostatic Potential", ACS Nano, vol. 5, No. 10, Oct. 25, 2011 (Oct. 25, 2011), pp. 8288-8294.

Little, D.P. et al., MALDI on a Chip: Analysis of Arrays of Low-Femtomole to Subfemtomole Quantities of Synthetic Oligonucleotides and DNA Diagnostic Products Dispensed by a Piezoelectric Pipet. Analytical Chemistry, 69 (22), 4540-4546 (1997).

Liu, J.Z. et al. Association analyses identify 38 susceptibility loci for inflammatory bowel disease and highlight shared genetic risk across populations. Nature genetics 47, 979-986 (2015).

Liu, Y. et al., Theranostic near-infrared fluorescent nanoplatform for imaging and systemic siRNA delivery to metastatic anaplastic thyroid cancer, Proceedings of the National Academy of Sciences of the United States of America Jul. 12, 2016, 113, 7750-7755.

Longo, C. et al. Core-shell hydrogel particles harvest, concentrate and preserve labile low abundance biomarkers. PLoS one 4, e4763 (2009).

Luchini, A. et al. Smart hydrogel particles: biomarker harvesting: one-step affinity purification, size exclusion, and protection against degradation. Nano letters 8, 350-361 (2008).

Ludwig, J. A. & Weinstein, J. N. Biomarkers in cancer staging, prognosis and treatment selection. Nature Reviews Cancer 5, 845-856 (2005).

Lundqvist, et al. The nanoparticle protein corona formed in human blood or human blood fractions. PLoS one 12.4 (Apr. 17, 2017): e0175871. 15 Pages.

Lundqvist, M., et al. Nanoparticle size and surface properties determine the protein corona with possible implications for biological impacts. Proc Natl Acad Sci U S A 105, 14265-14270 (2008).

(56) References Cited

OTHER PUBLICATIONS

Machado, R. F., Laskowski, D., Deffenderfer, O., et al. Detection of Lung Cancer by Sensor Array Analyses of Exhaled Breath. American journal of respiratory and critical care medicine 2005, 171, 1286-1291.
Maciel, C. M. et al. Differential proteomic serum pattern of low molecular weight proteins expressed by adenocarcinoma lung cancer patients. Journal of experimental therapeutics & oncology 5 (2005).
Mahmoudi, M., Bertrand, N., Zope, H. & Farokhzad, O.C. Emerging understanding of the protein corona at the nano-bio interfaces. Nano Today 11, 817-832 (2016).
Mahmoudi, M. et al. Protein- nanoparticle interactions: opportunities and challenges. Chemical reviews 111, 5610-5637 (2011).
Mahmoudi, M. et al. Variation of protein corona composition of gold nanoparticles following plasmonic heating. Nano letters 14, 6-12 (2013).
Mahmoudi, M., Lohse, S., Murphy, C. J. & Suslick, K. S. Identification of Nanoparticles with a Colorimetric Sensor Array. ACS Sensors 1, 17-21 (2016).
Mahmoudi, M., Saeedi-Eslami, S. N., Shokrgozar, M.A., et al. Cell "Vision": Complementary Factor of Protein Corona in Nanotoxicology. Nanoscale 2012, 4, 5461-5468.
Majek, P., Reicheltova, Z., Suttnar, J., et al. Plasma Proteome Changes in Cardiovascular Disease Patients: Novel Isoforms of Apolipoprotein A 1. Journal of translational medicine 2011, 9, 84.
Malik, G. et al. Serum levels of an isoform of apolipoprotein A-II as a potential marker for prostate cancer. Clinical Cancer Research 11, 1073-1085 (2005).
Mani, et al., Magnetic particles in ultrasensitive biomarker protein measurements for cancer detection and monitoring. Expert Opin Med Diagn. Sep. 1, 2011; 5(5): 381-391.
Matuszak, et al. "Drug delivery to atherosclerotic plaques using superparamagnetic iron oxide nanoparticles." International journal of nanomedicine vol. 13 8443-8460. Dec. 11, 2018, doi:10.2147/IJN.S179273.
Micallef, J. et al. Applying mass spectrometry based proteomic technology to advance the understanding of multiple myeloma. Journal of hematology & oncology 3, 1 (2010).
Miller, A., Hoogstraten, B., Staquet, M. & Winkler, A. Reporting results of cancer treatment. cancer 4 7, 207-214 (1981).
Millioni et al., High Abundance Proteins Depletion vs Low Abundance Proteins Enrichment: Comparison of Methods to Reduce the Plasma Proteome Complexity, PloS One, 2011, 6, 5, e19603.
Miotto G, et al. Protein corona as a proteome fingerprint: The example of hidden biomarkers for cow mastitis. Colloids Surf B Biointerfaces. 2016; 140:40-49. doi:10.1016/j.colsurfb.2015.11.043.
Mirshafiee, et al., Protein corona significantly reduces active targeting yield. Chemical communications vol. 49,25(2013): 2557-9. doi:10.1039/c3cc37307j.
Mirshafiee, V. et al., The importance of selecting a proper biological milieu for protein corona analysis in vitro: Human plasma versus human serum. Int J Biochem Cell Biol. Jun. 2016;75:188-95. doi:10.1016/j.biocel.2015.11.019. Epub Nov. 2, 20158.
Mirshafiee, V., Kim, R., Park, S., Mahmoudi, M. & Kraft, M.L. Impact of protein pre-coating on the protein corona composition and nanoparticle cellular uptake. Biomaterials 75, 295-304 (2016).
Misek, D. E., Patwa, T. H., Lubman, D. M. & Simeone, D. M. Early detection and biomarkers in pancreatic cancer. Journal of the National Comprehensive Cancer Network 5, 1034-1041 (2007).
Mody, et al. Introduction to metallic nanoparticles. Journal of Pharmacy and Bioallied Sciences 2.4 (2010): 282-289.
Monopoli, et al. Nanoparticle coronas take shape. Nature Nanotechnology, Jan. 2011. vol. 6; 11-12.
Monopoli, M.P., Aberg, C., Salvati, A. & Dawson, K.A. Biomolecular coronas provide the biological identity of nanosized materials. Nat Nanotechnol 7, 779-786 (2012).
Monopoli, M.P., et al. Physical-chemical aspects of protein corona: relevance to in vitro and in vivo biological impacts of nanoparticles. J Am Chem Soc 133, 2525-2534 (2011).
Mortensen, N. P.; Hurst, G. B.; Wang, W.; Foster, C. M.; Nallathamby, P. D.; Retterer, S. T., Dynamic development of the protein corona on silica nanoparticles: composition and role in toxicity. Nanoscale 2013, 5 (14), 6372-6380.
Muntoni, S. et al. Serum lipoproteins and cancer. Nutrition, Metabolism and Cardiovascular Diseases 19, 218-225 (2009).
Nel, A.E. et al. Understanding biophysicochemical interactions at the nano-bio interface. Nature materials 8, 543 2009.
Nie, S. et al. Glycoprotein biomarker panel for pancreatic cancer discovered by quantitative proteomics analysis. Journal of proteome research 13, 1873-1884 (2014).
Ono, M. et al. Prolyl 4-Hydroxylation of α-Fibrinogen: A Novel Protein Modification Revealed By Plasma Proteomics. Journal of Biological Chemistry 284, 29041-29049 (2009).
O'Rourke, N. & Edwards, R. Lung cancer treatment waiting times and tumour growth. Clinical Oncology 12, 141-144 (2000).
Orr, W. S., Sandoval, J. A., Malkas, L. H. & Hickey, R. J. Acute Phase Proteins as Cancer Biomarkers. (INTECH Open Access Publisher, 2011).
Ostrand-Rosenberg, S., Cancer and complement. Nature biotechnology vol. 26, No. 12, Dec. 2008;1348-1349.
Paez, J. G. et al. EGFR mutations in lung cancer: correlation with clinical response to gefitinib therapy. Science 304, 1497-1500 (2004).
Palchetti, et al. Exploitation of nanoparticle-protein corona for emerging therapeutic and diagnostic applications. Journal of Materials Chemistry B 4.25 (May 23, 2016): 4376-4381.
Palchetti, S.; Colapicchioni, V.; Digiacomo, L.; Caracciolo, G.; Pozzi, D.; Capriotti, A. L.; La Barbera, G.; Lagana, A., The protein corona of circulating PEGylated liposomes. Biochimica et Biophysica Acta (BBA)—Biomembranes 2016, 1858 (2), 189-196.
Palchetti, S. et al. Nanoparticles-cell association predicted by protein corona fingerprints. Nanoscale 8(25):12755-12763 doi:10.1039/C6NR03898K (2016).
Palmieri, V. et al. Dynamic light scattering for the characterization and counting of extracellular vesicles: a powerful noninvasive tool. Journal of Nanoparticle Research 16, 1-8 (2014).
Pan, S., Brentnall, T. A. & Chen, R. Proteomics analysis of bodily fluids in pancreatic cancer. Proteomics 15, 2705-2715 (2015).
Pan, S. et al. Multiplex targeted proteomic assay for biomarker detection in plasma: a pancreatic cancer biomarker case study. Journal of proteome research 11, 1937-1948 (2012).
Pan, S. et al. Protein alterations associated with pancreatic cancer and chronic pancreatitis found in human plasma using global quantitative proteomics profiling. Journal of proteome research 10, 2359-2376 (2011 ).
Panda, et al., Affinity Pulldown of Biotinylated RNA for Detection of Protein-RNA Complexes. Bio Protoc. Dec. 20, 2016; 6(24): e2062, pp. 1-10.
Pang, W.W., Abdul-Rahman, P. S., Izlina Wan-Ibrahim, W. & Haji Hashim, 0. Can the acute-phase reactant proteins be used as cancer biomarkers? International Journal of Biological Markers 25, 1 (2010).
Papi, M. et al., Exploitation of nanoparticle-protein interactions for early disease detection. Applied Physics Letters 2019, 114, paper 163702, 5 pages.
Pardo, et al., Resolving Affinity Purified Protein Complexes by Blue Native PAGE and Protein Correlation Profiling. J Vis Exp. 2017; 122:55498, pp. 1-11.
Patra, et al., Component-Specific Analysis of Plasma Protein Corona Formation on Gold Nanoparticles Using Multiplexed Surface Plasmon Resonance. Small, 2016; 12(9): 1174-1182.
Patwa, T. H. et al. The identification of phosphoglycerate kinase-1 and histone H4 autoantibodies in pancreatic cancer patient serum using a natural protein microarray. Electrophoresis 30, 2215-2226 (2009).
PCT/US2017/067013 International Search Report dated May 1, 2018.
PCT/US2017/067013 Written Opinion of the International Searching Authority dated May 1, 2018.

(56) References Cited

OTHER PUBLICATIONS

PCT/US2020/044908 International Search Report and Written Opinion dated Jan. 12, 2021.
Peer, D. et al. Nanocarriers as an emerging platform for cancer therapy. Nature nanotechnology 2, 751-760 (2007).
Pepe, M. S. et al. Phases of biomarker development for early detection of cancer. Journal of the National Cancer Institute 93, 1054-1061 (2001).
Petricoin, E. F. & Liotta, L.A. SELDI-TOF-based serum proteomic pattern diagnostics for early detection of cancer. Current Opinion in Biotechnology 15, 24-30 (2004).
Pichler, M. et al. High plasma fibrinogen level represents an independent negative prognostic factor regarding cancer-specific, metastasis-free, as well as overall survival in a European cohort of non-metastatic renal cell carcinoma patients. British journal of cancer 109, 1123 (2013).
Pio, R., Ajona, D. & Lambris, J. D. Complement inhibition in cancer therapy. Seminars in Immunology 25, 54-64, doi: http://dx.doi.org/10.1016/j.smim.2013.04.001 (2013).
Pio, R., Corrales, L. & Lambris, J. D. The Role of Complement in Tumor Growth, Adv Exp Med Biol., 229-262 (Springer, 2014).
Popescu, I. D. et al. Potential serum biomarkers for glioblastoma diagnostic assessed by proteomic approaches. Proteome science 12, 1 (2014).
Pourshams, A. et al. Cohort profile: the Golestan Cohort Study—a prospective study of oesophageal cancer in northern Iran. International journal of epidemiology 39, 52-59 (2010).
Pozzi, et al., Surface chemistry and serum type both determine the nanoparticle-protein corona. Journal of Proteomics, 2015, 119, 209-217.
Puri et al.: Lipid-based nanoparticles as pharmaceutical drug carriers: from concepts to clinic. Critical Reviews™ in Therapeutic Drug Carrier Systems. 26(6):523-580 (2009).
Qian, W.-J. et al. Enhanced detection of low abundance human plasma proteins using a tandem IgY12—SuperMix immunoaffinity separation strategy. Molecular & Cellular Proteomics 7, 1963-1973 (2008).
Rahimi, M. et al. Zeolite Nanoparticles for Selective Sorption of Plasma Proteins. Scientific reports 5, 17259-17259 (2015).
Rahman et al., Nanoparticle and Protein Corona, Chapter 2 in Protein-Nanoparticle Interactions, Springer Series in Biophysics 15, pp. 21-44 (Springer Science & Business Media, 2013).
Rahman M et al.: Disease specific protein corona, Progress in Biomedical Optics and Imaging, SPIE-International Society for Optical Engineering, Bellingham, WA, US, vol. 9338, Mar. 11, 2015 (Mar. 11, 2015), pp. 93380V-93380V,XP060049391, ISSN: 1605-7422, DOI: 10.1117/12.2079771ISBN: 978-1-5106-0027-0.
Rakow, N. A., Suslick, K. S. A Colorimetric Sensor Array for Odour Visualization. Nature 2000, 406, 710-713.
Ridker, P. M., Hennekens, C. H., Suring, J. E., Rifai, N. C-Reactive Protein and Other Markers of Inflammation in the Prediction of Cardiovascular Disease in Women. New England Journal of Medicine 2000, 342, 836-843.
Ritz, S. et al., Protein Corona of Nanoparticles: Distinct Proteins Regulate the Cellular Uptake, Biomacromolecules 2015, 16, 1311-1321, with 11 pages of supporting information.
Rubio-Perez, C. et al. In silico prescription of anticancer drugs to cohorts of 28 tumor types reveals targeting opportunities. Cancer cell 27, 382-396 (2015).
Safarik, et al., Magnetic techniques for the isolation and purification of proteins and peptides. Biomagn Res Technol. 2004; 2(7): 1-17.
Saha, K. et al. Regulation of Macrophage Recognition through the Interplay of Nanoparticle Surface Functionality and Protein Corona. ACS nano 10, 4421-4430 (2016).
Sakulkhu et al., Ex situ evaluation of the composition of protein corona of intravenously injected superparamagnetic nanoparticles in rats. Nanoscale, Aug. 2014; 6:11439-11450.
Sakulkhu, et al. Significance of surface charge and shell material of superparamagnetic iron oxide nanoparticle SPION) based core/shell nanoparticles on the composition of the protein corona. Biomater. Sci., Jan. 20, 2015; vol. 3, 265-278.
Salehi-Reyhani, A., "Evaluating single molecule detection methods for microarrays with high dynamic range for quantitative single cell analysis." Scientific Reports, Dec. 20, 2017, vol. 7, No. 17957, pp. 1-12.
Salvador-Morales, C., Zhang, L., Langer, R. & Farokhzad, O.C. Immunocompatibility properties of lipid-polymer hybrid nanoparticles with heterogeneous surface functional groups. Biomaterials 30, 2231-2240 (2009).
Salvati, A. et al. Transferrin-functionalized nanoparticles lose their targeting capabilities when a biomolecule corona adsorbs on the surface. Nature nanotechnology 8, 137-143 (2013).
Schindelin, J. et al. Fiji: an open-source platform for biological-image analysis. Nature methods 9, 676-682 (2012).
Schrittwieser, S. et al. Direct protein quantification in complex sample solutions by surface-engineered nanorod probes. Scientific Reports, 2017, 7(4752): https://doi.org/10.1038/s41598-017-04970-5.
Semb, K. A., Aamdal, S. & Oian, P. Capillary protein leak syndrome appears to explain fluid retention in cancer patients who receive docetaxel treatment. Journal of Clinical Oncology 16, 3426-3432 (1998).
Senyo, S.E. et al. Mammalian heart renewal by pre-existing cardiomyocytes. Nature 493, 433-436 (2013).
Shakeri, R. et al. Multiplex H. pylori serology and risk of gastric cardia and noncardia adenocarcinomas. Cancer research 75, 4876-4883 (2015).
Sharma, S., Ray, S., Moiyadi, A., Sridhar, E. & Srivastava, S. Quantitative proteomic analysis of meningiomas for the identification of surrogate protein markers. Scientific reports 4, 7140 (2014).
Shi, J., Kantoff, P.W., Wooster, R. & Farokhzad, O.C. Cancer nanomedicine: progress, challenges and opportunities. Nat Rev Cancer 17, 20-37 (2017).
Shi, T. et al. IgY14 and SuperMix immunoaffinity separations coupled with liquid chromatography-mass spectrometry for human plasma proteomics biomarker discovery. Methods 56, 246-253 (2012).
Shoji, M. et al. Activation of coagulation and angiogenesis in cancer: immunohistochemical localization in situ of clotting proteins and vascular endothelial growth factor in human cancer. The American journal of pathology 152, 399 (1998).
Siddiqui, et al., Plasma protein-protein interactome (PPI) maps derived from the protein corona captured at the nano-bio interface of nanoparticles reveal differential networks for non-small cell lung cancer (NSCLC) and control subjects. Seer, Inc. Apr. 2020. 1 Page.
Siegel, R. L., Miller, K. D. & Jemal, A. Cancer statistics, 2015. CA: a cancer journal for clinicians 65, 5-29 (2015).
Siegel, R. L., Miller, K. D. & Jemal, A. Cancer statistics, 2016. CA: a cancer journal for clinicians 66, 7-30 (2016).
Simberg, et al. Differential proteomics analysis of the surface heterogeneity of dextran iron oxide nanoparticles and the implications for their in vivo clearance. Biomaterials. Aug. 2009; 30(23-24): 3926-3933.
Singh, et al. Drug delivery: advancements and challenges. Nanostructures for Drug Delivery. Elsevier, 2017. 865-886.
Smith, R. A. et al. American Cancer Society guidelines for the early detection of cancer. CA: a cancer journal for clinicians 52, 8-22 (2002).
Snider, et al., Fundamentals of protein interaction network mapping. Mol Syst Biol. Dec. 2015; 11(848):1-20.
Star, A., Joshi, V., Skarupo, S., Thomas, D., Gabriel, J.-C. P. Gas Sensor Array Based on Metal- Decorated Carbon Nanotubes. The Journal of Physical Chemistry B 2006, 110, 21014-21020.
Staton, C.A., Brown, N.J. & Lewis, C.E. The role of fibrinogen and related fragments in tumour angiogenesis and metastasis. Expert opinion on biological therapy 3, 1105-1120 (2003).
Strehlitz, et al., Protein detection with aptamer biosensors, sensors, Jul. 23, 2008. vol. 8, No. 7 p. 4296-4307.
Strojan, K. et al. Dispersion of nanoparticles in different media importantly determines the composition of their protein corona. PloS one 12, e0169552 (2017).

(56) References Cited

OTHER PUBLICATIONS

Sun, C., Rosendahl, A.H., Ansari, D. & Andersson, R. Proteome-based biomarkers in pancreatic cancer. World J Gastroenterol 17, 4845-4852 (2011).

Sun, Z.-L. et al. Serum proteomic-based analysis of pancreatic carcinoma for the identification of potential cancer biomarkers. Biochimica et Biophysica Acta (BBA)-Proteins and Proteomics 1774, 764-771 (2007).

Sung, H.J., et al. Identification and validation of SAA as a potential lung cancer biomarker and its involvement in metastatic pathogenesis of lung cancer. J Proteome Res 10, 1383-1395 (2011).

Suslick, B.A., Feng, L. & Suslick, K.S. Discrimination of complex mixtures by a colorimetric sensor array: coffee aromas. Analytical chemistry 82, 2067-2073 (2010).

Szala, A. et al. Ficolin-2 and ficolin-3 in women with malignant and benign ovarian tumours. Cancer Immunology, Immunotherapy 62, 1411-1419 (2013).

Tan, H. T., Low, J., Lim, S. G. & Chung, M. Serum autoantibodies as biomarkers for early cancer detection. FEBS journal 276, 6880-6904 (2009).

Tenzer, S., et al. Nanoparticle size is a critical physicochemical determinant of the human blood plasma corona: a comprehensive quantitative proteomic analysis. ACS Nano 5, 7155-7167 (2011).

Tenzer, S., et al. Rapid formation of plasma protein corona critically affects nanoparticle pathophysiology. Nat Nanotechnol 8, 772-781 (2013).

Thermo Fisher Scientific "Orbitrap Velos Pro Hardware Manual, Revision A—1288290", Jun. 2011, 202 pages.

Tirtaatmadja, N. et al. Nanoparticles-induced inflammatory cytokines in human plasma concentration manner: an ignored factor at the nanobio-interface. Journal of the Iranian Chemical Society 12, 317-323 (2015).

Tousoulis, D., Charakida, M., Stefanadis, C. Endothelial Function and Inflammation in Coronary Artery Disease. Heart 2006, 92, 441-444.

Trinkle-Mulcahy, et al., Identifying specific protein interaction partners using quantitative mass spectrometry and bead proteomes. J Cell Biol. Oct. 2, 20080; 183(2): 223-239.

Troiano et al., A Quality by Design Approach to Developing and Manufacturing Polymeric Nanoparticle Drug Products, The AAPS Journal, 2016, 18, 6, 1354-1365.

Turner, A. P., Chen, B., Piletsky, S. A. In Vitro Diagnostics in Diabetes: Meeting the Challenge. Clinical chemistry 1999, 45, 1596-1601.

U.S. Appl. No. 15/880,627 Notice of Allowance dated Sep. 18, 2020.

U.S. Appl. No. 15/880,627 Office Action dated Dec. 18, 2018.
U.S. Appl. No. 15/880,627 Office Action dated Jan. 30, 2020.
U.S. Appl. No. 15/880,627 Office Action dated Jun. 18, 2019.
U.S. Appl. No. 15/880,627 Office Action dated Jun. 20, 2018.
U.S. Appl. No. 17/099,331 Office Action dated Apr. 20, 2021.
U.S. Appl. No. 17/099,331Office Action dated Aug. 17, 2021.
U.S. Appl. No. 17/215,923 Office Action dated Sep. 22, 2021.
U.S. Appl. No. 17/215,952 Office Action dated Jun. 10, 2021.
U.S. Appl. No. 17/215,952 Office Action dated Sep. 17, 2021.
U.S. Appl. No. 17/215,966 Office Action dated Jun. 3, 2021.
U.S. Appl. No. 17/215,966 Office Action Sep. 23, 2021.
U.S. Appl. No. 17/215,978 Office Action dated Jun. 10, 2021.
U.S. Appl. No. 17/215,978 Office Action dated Oct. 8, 2021.

Vollmers, H. P. & Brandlein, S. Natural human immunoglobulins in cancer immunotherapy. (2009).

Walkey, C.D. & Chan, W.C. Understanding and controlling the interaction of nanomaterials with proteins in a physiological environment. Chem Soc Rev 41, 2780-2799 (2012).

Walkey, et al., Protein corona fingerprinting predicts the cellular interaction of gold and silver nanoparticles. ACS Nano, 2014, 8(3): 2439-2455.

Wang, J. et al. Cancer-derived immunoglobulin G promotes tumor cell growth and proliferation through inducing production of reactive oxygen species. Cell death & disease 4, e945 (2013).

Wang, Y. et al. Proteomic differential display identifies upregulated vinculin as a possible biomarker of pancreatic cancer. Oncology reports 28, 1845-1850 (2012).

Ward, D. et al. Identification of serum biomarkers for colon cancer by proteomic analysis. British journal of cancer 94, 1898 (2006).

Welter, D. et al. The NHGRI GWAS Catalog, a curated resource of SNP-trait associations. Nucleic acids research 42, D1001-D1006 (2013).

Whelan, S.A. et al. Mass spectrometry (LC-MS/MS) identified proteomic biosignatures of breast cancer in proximal fluid. Journal of proteome research 11, 5034-5045 (2012).

Wildes, D. & Wells, J.A. Sampling the N-terminal proteome of human blood. Proceedings of the National Academy of Sciences 107, 4561-4566 (2010).

Wright, C.F. et al. Genetic diagnosis of developmental disorders in the DOD study: a scalable analysis of genome-wide research data. The Lancet 385, 1305-1314 (2015).

Wulfkuhle, J. D., Liotta, L. A. & Petricoin, E. F. Proteomic applications for the early detection of cancer. Nature reviews cancer 3, 267-275 (2003).

Xia, X.-R., Monteiro-Riviere, N.A. & Riviere, J.E. An index for characterization of nanomaterials in biological systems. Nature nanotechnology 5, 671-675 (2010).

Xu, et al., Streptavidin Bead Pulldown Assay to Determine Protein Homooligomerization. Bio Protoc. Nov. 20, 2017; 7(22): e2901, pp. 1-11.

Yan, L. et al. Confounding effect of obstructive jaundice in the interpretation of proteomic plasma profiling data for pancreatic cancer. Journal of proteome research 8, 142-148 (2008).

Yates, J.R., Ruse, C.I. & Nakorchevsky, A. Proteomics by mass spectrometry: approaches, advances, and applications. Annual review of biomedical engineering 11, 49-79 (2009).

Yigitbasi, T., "Multiplex immunoassay and bead based multiplex." Trends in Immunolabelled and Related Techniques. (2012): 351.

Yigitbasi, Turkan: "Multiplex Immunoassay and Bead Based Multiplex", Apr. 27, 2012, Trends in Immunolabelled and Related Techniques. 22:351-360, XP0556537 41,Retrieved from the Internet: URL: https://www.researchgate.net/profile/Ravichandran_Panchanathan/post/What_are_differences_of_different_types_of_multiplex_cytokine_ELISA/attachment/59d61ddf79197b807797b6fb/AS:273775503839238@144228457 4432/download/36219.pdf[retrieved on Dec. 17, 2019] (2012).

Yoneyama, T. et al. Identification of IGFBP2 and IGFBP3 As Compensatory Biomarkers for CA 19-9 in Early-Stage Pancreatic Cancer Using a Combination of Antibody-Based and LC-MS/MS-Based Proteomics. PloS one 11, e0161009 (2016).

Yusuf et al., Global Burden of Cardiovascular Diseases. Circulation, Dec. 4, 2001; 104(23):2855-64.

Zaccaria, et al. Accessing to the minor proteome of red blood cells through the influence of the nanoparticle surface properties on the corona composition. International journal of nanomedicine 10 (Mar. 9, 2015): 1869-1883.

Zakynthinos, E., Pappa, N. Inflammatory Biomarkers in Coronary Artery Disease. Journal of cardiology 2009, 53, 317-333.

Zanganeh, et al. Protein corona: opportunities and challenges. The international journal of biochemistry & cell biology 75 (Jun. 2016): 143-147.

Zhang, C. & Suslick, K. S. Colorimetric sensor array for soft drink analysis. Journal of agricultural and food chemistry 55, 237-242 (2007).

Zhang, et al. Quantitative proteomics analysis of adsorbed plasma proteins classifies nanoparticles with different surface properties and size. Proteomics. Dec. 2011; 11 (23): pp. 4569-4577.

Zhang, Y., Askim, J.R., Zhong, W., Orlean, P. & Suslick, K.S. Identification of pathogenic fungi with an optoelectronic nose. Analyst 139, 1922-1928 (2014).

Zheng, et al., Gold Nanoparticle-enabled blood test for early stage cancer detection and risk assessment. ACS Appl. Mater. Interfaces 2015; 7: 6819-6827.

Zheng, et al. Multiplexed electrical detection of cancer markers with nanowire sensor arrays. Nat Biotechnol. Oct. 2005;23(10):1294-301. Epub Sep. 18, 2005.

(56) References Cited

OTHER PUBLICATIONS

Zheng, T. et al. A Rapid Blood Test To Determine the Active Status and Duration of Acute Viral Infection. ACS Infectious Diseases (2017).

Zupancic, K. et al. Identification of plasma biomarker candidates in glioblastoma using an antibody-array-based proteomic approach. Radiology and oncology 48, 257-266 (2014).

Zwicker, J. I., Furie, B. C. & Furie, B. Cancer-associated thrombosis. Critical reviews in oncology/hematology 62, 126-136 (2007).

Chen, Shao-Yung (Eric), et al., Comprehensive and automated profiling of host cell proteins using the Proteograph™ XT workflow. 8 pages. (2023). Accessed online Jan. 8, 2024. URL: https://media.seer.bio/uploads/2023/10/comprehensiveAutomatedProfilingHCP-proteographXT.pdf.

Chen, Shao-Yung (Eric), et al., Unbiased and deep proteomic analysis of secretome samples using the Proteograph™ XT workflow. 7 pages. (2023). Accessed online Jan. 8, 2024. URL: https://media.seer.bio/uploads/2023/12/Secretome-ProteographXT_AppNote_Seer.pdf.

Co-pending U.S. Appl. No. 18/318,563, inventors Li; Biao et al., filed May 16, 2023.

Co-pending U.S. Appl. No. 18/395,124, inventors Langer; Robert S. et al., filed Dec. 22, 2023.

Co-pending U.S. Appl. No. 18/407,278, inventors Manning; William et al., filed Jan. 8, 2024.

Co-pending U.S. Appl. No. 18/547,831, inventors Hornburg; Daniel et al., filed Aug. 24, 2023.

Co-pending U.S. Appl. No. 18/557,753, inventors Siddiqui; Asim et al., filed Oct. 27, 2023.

Co-pending U.S. Appl. No. 18/578,513, inventors Platt; Theodore et al., filed Jan. 11, 2024.

Huang, Ting, et al., Deep, unbiased and quantitative mass spectrometry-based plasma proteome analyses of adaptive response to COVID-19 vaccine. 1 page. (2023) Accessed online Jan. 8, 2024. URL: https://media.seer.bio/uploads/2023/06/2023_Poster_ASMS_THuang.pdf.

Huang, Ting, et al., Protein Coronas on Functionalized Nanoparticles Enable Quantitative and Precise Large-Scale Deep Plasma Proteomics. 1 page. (2023). Accessed online Jan. 8, 2024. URL: https://media.seer.bio/uploads/2023/09/2023_Poster_Cantrell.pdf.

Jiang, Wei, et al., Human biofluids analysis using a scalable, deep, unbiased, automated, nanoparticle- based proteomics platform. 1 page. (2023). Accessed online Jan. 8, 2024. URL: https://media.seer.bio/uploads/2023/03/2023_Poster_USHUPO_Gajadhar.pdf.

Li, J. et al. Block copolymer conjugated Au-coated Fe3O4 nanoparticles as vectors for enhancing colloidal stability and cellularuptake, Journal of Nanobiotechnology, 15(56) 1-11 (Year: 2017).

Motamedchaboki, Khatereh, et al., Plasma Proteomic Landscape of Alzheimer's Disease: An 1800-Sample Cohort Study. 1 page. (2023). Accessed online Jan. 8, 2024. URL: https://media.seer.bio/uploads/2023/09/2023_Poster_Siddiqui.pdf.

Siegel et al. Cancer statistics, 2015. CA Cancer J Clin 65:5-29 (2015).

Siegel et al. Cancer statistics, 2016. CA Cancer J Clin 66:7-30 (2016).

U.S. Appl. No. 17/216,523 Notice of Allowance dated Dec. 5, 2022.
U.S. Appl. No. 17/216,523 Office Action dated Jan. 5, 2022.
U.S. Appl. No. 18/088,946 Notice of Allowance dated Jan. 25, 2024.
U.S. Appl. No. 18/178,288 Office Action dated Dec. 21, 2023.
U.S. Appl. No. 18/365,627 Office Action dated Dec. 19, 2023.
U.S. Appl. No. 18/365,674 Notice of Allowance dated Dec. 1, 2023.
U.S. Appl. No. 18/460,221 Office Action dated Dec. 21, 2023.
U.S. Appl. No. 18/460,254 Office Action dated Dec. 22, 2023.

Bertoli, Filippo, et al., Magnetic Nanoparticles to Recover Cellular Organelles and Study the Time Resolved Nanoparticle-cell Interactome Throughout Uptake. Small 10(16):3307-3315 (2014).

Giri, K. Engineered gold nanoparticles for identification of novel ovarian biomarkers. Mayo Clinic College of Medicine Thesis. Jan. 2016. 142 pages.

Hamad-Schifferli, K. Exploiting the novel properties of protein coronas: emerging applications in nanomedicine. Nanomedicine (Lond). May 2015;10(10):1663-74. doi: 10.2217/nnm. 15.6.

Kaufmann, Anton, et al., Comparison of Linear Intrascan and Interscan Dynamic Ranges of Orbitrap and Ion-mobility Time-of-flight Mass Spectrometers. Rapid Communications in Mass Spectrometry 31(22):1915-1926 (2017).

Maiolo, et al. Nanomedicine delivery: does protein corona route to the target or off road? Nanomedicine (Lond). 2015;10(21):3231-47. doi: 10.2217/nnm.15.163. Epub Oct. 1, 20156.

* cited by examiner

1. Transferring sample into substrate partition with sensor array
2. Sensor array binding
3. Removal of unbound sample
4. Prep for MS (generate a MS ready sample)

FIG. 7

SYSTEMS AND METHODS FOR SAMPLE PREPARATION, DATA GENERATION, AND PROTEIN CORONA ANALYSIS

CROSS-REFERENCE

The present application is a continuation of U.S. Non-Provisional application Ser. No. 18/178,288, filed Mar. 3, 2023, which is a continuation of U.S. Non-Provisional application Ser. No. 17/216,523, filed Mar. 29, 2021, issued as U.S. Pat. No. 11,630,112, on Apr. 18, 2023, which is a continuation of International Application No. PCT/US2020/044908, filed Aug. 4, 2020, which claims the benefit of U.S. Provisional Patent Application No. 62/883,107, filed Aug. 5, 2019, each of which is herein incorporated by reference in its entirely.

BACKGROUND

Broad scale implementation of proteomic information in science and medicine has lagged behind genomics in large part because of complexities inherent in protein molecules themselves, necessitating complex workflows that limit the scalability of such analyses. Disclosed herein are systems, methods and kits for rapid and automated sample preparation, processing of proteomic data and the identification of key biomarkers associated with diseased states.

SUMMARY

The present disclosure provides automated systems, methods and kits for protein corona preparation and analysis. In some aspects, the present disclosure provides an automated apparatus for generating a subset of biomolecules from a complex biological sample, the automated apparatus comprising: (i) a substrate comprising a plurality of partitions, wherein the plurality of partitions comprises a plurality of particles; (ii) a sample storage unit comprising the complex biological sample; and (iii) a loading unit that is movable at least across the substrate, wherein the loading unit transfers one or more volumes of the complex biological sample in the sample storage unit to the plurality of partitions on the substrate, thereby contacting the plurality of particles in the plurality of partitions with biomolecules of the complex biological sample to form biomolecule coronas, thereby generating the subset of biomolecules of the complex biological sample, and wherein a dynamic range of the subset of biomolecules is compressed relative to a dynamic range of biomolecules present in the complex biological sample. In some embodiments, the substrate is a multi-well plate. In some embodiments, the subset of biomolecules comprises at least 20% to at least 60% of the types of biomolecules from the complex biological sample within a 6 order of magnitude concentration range. In some embodiments, the subset of biomolecules comprises at least 20% to at least 60% of the types of proteins from the complex biological sample within a 6 order of magnitude concentration range. In some embodiments, the automated apparatus generates the subset of biomolecules from a complex biological sample in less than 7 hours.

In some embodiments, the automated apparatus comprises an incubation element that agitates or heats volumes of the plurality of particles within volumes of the complex biological sample in the plurality of partitions. In some embodiments, the incubation element is configured to shake, mix, stir, spin, vibrate, be static, or any combination thereof. In some embodiments, the wherein the incubation element is configured to heat and/or incubate the substrate to a temperature between about 20° C. and about 100° C.

In some embodiments, the plurality of partitions is at least partially covered or sealed. In some embodiments, a partition from among the plurality of partitions is covered or sealed. In some embodiments, the automated apparatus comprises the ability to add or remove a lid on the substrate, wherein the lid covers at least one of the partitions from among the plurality of partitions.

In some embodiments, the automated apparatus comprises a unit comprising a resuspension solution. In some embodiments, the resuspension solution comprises Tris EDTA 150 mM KCl 0.05% CHAPS buffer. In some embodiments, the resuspension solution comprises 10 mM Tris HCl pH 7.4, 1 mM EDTA.

In some embodiments, the apparatus comprises a unit comprising a denaturing solution. In some embodiments, the denaturing solution comprises a protease. In some embodiments, the denaturing solution comprises a reductant, a methylating agent, guanidine, urea, sodium deoxycholate, acetonitrile, or any combination thereof. In some embodiments, the denaturing solution generates an average peptide fragment with a mass of less than 4600 Daltons.

In some embodiments, the loading unit comprises a plurality of pipettes. In some embodiments, the loading unit is configured to dispense 10 uL to 400 uL of a solution into one or more partitions of the plurality of partitions. In some embodiments, the loading unit is configured to dispense 5 uL to 150 uL of a solution into one or more partitions of the plurality of partitions. In some embodiments, the loading unit is configured to dispense 35 uL to 80 uL of a solution into one or more partitions of the plurality of partitions. In some embodiments, the solution is selected from the group consisting of a wash solution, the resuspension solution, the denaturing solution, a buffer and a reagent. In some embodiments, the loading unit is configured to dispense 10 uL to 400 uL of the complex biological sample into one or more partitions of the plurality of partitions. In some embodiments, the loading unit is configured to dispense 5 uL to 150 uL of the complex biological sample into one or more partitions of the plurality of partitions. In some embodiments, the loading unit is configured to dispense 35 uL to 80 uL of the complex biological sample into one or more partitions of the plurality of partitions.

In some embodiments, the complex biological sample comprises a biofluid from a subject. In some embodiments, the complex biological sample comprises plasma, serum, urine, cerebrospinal fluid, synovial fluid, tears, saliva, whole blood, milk, nipple aspirate, ductal lavage, vaginal fluid, nasal fluid, ear fluid, gastric fluid, pancreatic fluid, trabecular fluid, lung lavage, sweat, crevicular fluid, semen, prostatic fluid, sputum, fecal matter, bronchial lavage, fluid from swabbings, bronchial aspirants, fluidized solids, fine needle aspiration samples, tissue homogenates, lymphatic fluid. cell culture samples, or any combination thereof.

In some embodiments, the automated apparatus further comprises a magnet. In some embodiments, one or more particles of the plurality of particles is a magnetic particle, and the substrate and the magnet are in proximity such that the one or more magnetic particles are immobilized on the substrate In some embodiments, the automated apparatus further comprises a housing, the substrate and the loading unit are located in the housing, and the housing is at least partially enclosed.

In some embodiments, the compressed dynamic range comprises an increase in the number of types of biomolecules whose concentrations are within 6 orders of magnitude of the most abundant biomolecule in the sample. In some embodiments, the compressed dynamic range comprises an increase in the number of types of biomolecules whose concentrations are within 5 orders of magnitude of the most abundant biomolecule in the sample. In some embodiments, the compressed dynamic range comprises an increase in the number of types of biomolecules whose concentrations are within 4 orders of magnitude of the most abundant biomolecule in the sample. In some embodiments, the compressed dynamic range comprises an increase in the number of types of proteins whose concentrations are within 6 orders of magnitude of the most abundant protein in the sample. In some embodiments, the increase in the number of types of biomolecules whose concentrations are within 6 orders of magnitude of the most concentrated biomolecule in the sample is at least 25%, 50%, 100%, 200%, 300%, 500%, or 1000%. In some embodiments, the compressed dynamic range comprises an increase in the number of types of proteins whose concentrations are within 6 orders of magnitude of the most abundant protein in the sample. In some embodiments, the increase in the number of types of proteins whose concentrations are within 6 orders of magnitude of the most abundant protein in the sample is at least 25%, 50%, 100%, 200%, 300%, 500%, or 1000%.

In some embodiments, the dynamic range of the biomolecules of the biomolecule coronas is a first ratio of a top decile of biomolecules to a bottom decile of biomolecules in the plurality of biomolecule coronas. In some embodiments, the dynamic range of the biomolecules of the biomolecule coronas is a first ratio comprising a span of the interquartile range of biomolecules in the plurality biomolecule coronas.

In some embodiments, the generating enriches low abundance biomolecules from the complex biological sample. In some embodiments, the low abundance biomolecules are biomolecules at concentrations of 10 ng/mL or less in the complex biological sample. In some embodiments, the subset of biomolecules from the complex biological sample comprises proteins.

In some embodiments, changes of at most 10 mg/mL in the lipid concentration of the complex biological sample result in changes of less than 10%, 5%, 2%, or 1% in the composition of the proteins in the subset of biomolecules generated from the complex biological sample.

In some embodiments, at least two particles from among the plurality of particles differ in at least one physicochemical property. In some embodiments, the at least one physicochemical property is selected from the group consisting of: composition, size, surface charge, hydrophobicity, hydrophilicity, surface functionality, surface topography, surface curvature, porosity, core material, shell material, shape, and any combination thereof. In some embodiments, the surface functionality comprises aminopropyl functionalization, amine functionalization, boronic acid functionalization, carboxylic acid functionalization, methyl functionalization, N-succinimidyl ester functionalization, PEG functionalization, streptavidin functionalization, methyl ether functionalization, triethoxylpropylaminosilane functionalization, thiol functionalization, PCP functionalization, citrate functionalization, lipoic acid functionalization, BPEI functionalization. In some embodiments, a particle from among the plurality of particles is selected from the group consisting of: micelles, liposomes, iron oxide particles, silver particles, gold particles, palladium particles, quantum dots, platinum particles, titanium particles, silica particles, metal or inorganic oxide particles, synthetic polymer particles, copolymer particles, terpolymer particles, polymeric particles with metal cores, polymeric particles with metal oxide cores, polystyrene sulfonate particles, polyethylene oxide particles, polyoxyethylene glycol particles, polyethylene imine particles, polylactic acid particles, polycaprolactone particles, polyglycolic acid particles, poly(lactide-co-glycolide polymer particles, cellulose ether polymer particles, polyvinylpyrrolidone particles, polyvinyl acetate particles, polyvinylpyrrolidone-vinyl acetate copolymer particles, polyvinyl alcohol particles, acrylate particles, polyacrylic acid particles, crotonic acid copolymer particles, polyethlene phosphonate particles, polyalkylene particles, carboxy vinyl polymer particles, sodium alginate particles, carrageenan particles, xanthan gum particles, gum acacia particles, Arabic gum particles, guar gum particles, pullulan particles, agar particles, chitin particles, chitosan particles, pectin particles, karaya tum particles, locust bean gum particles, maltodextrin particles, amylose particles, corn starch particles, potato starch particles, rice starch particles, tapioca starch particles, pea starch particles, sweet potato starch particles, barley starch particles, wheat starch particles, hydroxypropylated high amylose starch particles, dextrin particles, levan particles, elsinan particles, gluten particles, collagen particles, whey protein isolate particles, casein particles, milk protein particles, soy protein particles, keratin particles, polyethylene particles, polycarbonate particles, polyanhydride particles, polyhydroxyacid particles, polypropylfumerate particles, polycaprolactone particles, polyamine particles, polyacetal particles, polyether particles, polyester particles, poly(orthoester) particles, polycyanoacrylate particles, polyurethane particles, polyphosphazene particles, polyacrylate particles, polymethacrylate particles, polycyanoacrylate particles, polyurea particles, polyamine particles, polystyrene particles, poly(lysine) particles, chitosan particles, dextran particles, poly(acrylamide) particles, derivatized poly(acrylamide) particles, gelatin particles, starch particles, chitosan particles, dextran particles, gelatin particles, starch particles, poly-3-amino-ester particles, poly(amido amine) particles, poly lactic-co-glycolic acid particles, polyanhydride particles, bioreducible polymer particles, and 2-(3-aminopropylamino)ethanol particles, and any combination thereof. In some embodiments, one or more particles of the plurality of particles adsorbs at least 100 types of proteins upon contacting the complex biological sample. In some embodiments, the plurality of particles comprises at least 2 distinct particle types, at least 3 distinct particle types, at least 4 distinct particle types, at least 5 distinct particle types, at least 6 distinct particle types, at least 7 distinct particle types, at least 8 distinct particle types, at least 9 distinct particle types, at least 10 distinct particle types, at least 11 distinct particle types, at least 12 distinct particle types, at least 13 distinct particle types, at least 14 distinct particle types, at least 15 distinct particle types, at least 20 distinct particle types, at least 25 particle types, or at least 30 distinct particle types.

In some embodiments, biomolecules of the biomolecule coronas comprise a number of protein groups. In some embodiments, the number of protein groups comprises from 1 to 20,000 protein groups. In some embodiments, the number of protein groups comprises from 100 to 10,000 protein groups. In some embodiments, the number of protein groups comprises from 100 to 5000 protein groups. In some embodiments, the number of proteins groups comprises from 300 to 2,200 protein groups. In some embodiments, the number of proteins groups comprises from 1,200 to 2,200 protein groups.

In some embodiments, at least two partitions of the plurality of partitions comprise different buffers. In some embodiments, the different buffers differ in pH, salinity, osmolarity, viscosity, dielectric constant, or any combination thereof. In some embodiments, at least two partitions of the plurality of partitions comprise different ratios of buffer and the complex biological sample. In some embodiments, one or more partitions of the plurality of partitions comprises 1 pM to 100 nM nanoparticles. In some embodiments, at least two partitions of the plurality of partitions comprise different concentrations of nanoparticles.

In some embodiments, the automated apparatus further comprises a purification unit. In some embodiments, the purification unit comprises a solid phase extraction (SPE) plate.

Various aspects of the present disclosure provide an automated system comprising: (i) an automated apparatus configured to isolate the subset of biomolecules from the biological sample; (ii) a mass spectrometer configured to receive the subset of biomolecules and to generate data comprising mass spectrometric or tandem mass spectrometric signals; and (iii) a computer comprising one or more computer processors and a computer readable medium comprising machine-executable code that, upon execution by the one or more computer processors, implements a method comprising: generating a biomolecule fingerprint and assigning a biological state based on the biomolecule fingerprint.

In some embodiments, the biomolecule fingerprint comprises a plurality of distinct biomolecule corona signatures. In some embodiments, the biomolecule fingerprint comprises at least 5, 10, 20, 40, or 80, 150 or 200 distinct biomolecule corona signatures. In some embodiments, the computer is configured to process the data comprising the intensity, APEX, spectral count or number of peptides, or Ion mobility behavior of the mass spectrometric or tandem mass spectrometric signal between a plurality of the distinct biomolecule corona signatures. In some embodiments, the computer is configured to process data from between 100 and 2000 mass spectrometric or tandem mass spectrometric signals between a plurality of the distinct biomolecule corona signatures. In some embodiments, the computer is configured to process the data comprising the intensities of between 10,000 and 5,000,000 mass spectrometric or tandem mass spectrometric signals between a plurality of the distinct biomolecule corona signatures. In some embodiments, the biomolecule fingerprint is generated from data from a single mass spectrometric or tandem mass spectrometric run. In some embodiments, the single mass spectrometric or tandem mass spectrometric run is performed in less than one hour. In some embodiments, the computer is configured to identify a biomolecule or characterize an unidentified molecular feature based on a mass spectrometric or tandem mass spectrometric signal and or ion mobility and chromatographic behavior, and wherein the computer provides a certainty threshold of at least 95% to identify a feature or characterize and unidentified feature. In some embodiments, the automated system is configured to generate the biomolecule fingerprint from the complex biological sample in less than about 10 hours. In some embodiments, the determining comprises comparing the abundance of two biomolecules whose concentrations span at least 7 to at least 12 orders of magnitude in the complex biological sample.

In some embodiments, the computer is capable of distinguishing between two or more biological states associated with biomolecule fingerprints that differ by less than 10%, 5%, 2%, or 1%. In some embodiments, the biological state is a disease, disorder, or tissue abnormality. In some embodiments, the disease is an early phase or intermediate phase disease state. In some embodiments, the disease is cancer. In some embodiments, the cancer is a stage 0 cancer or a stage 1 cancer. In some embodiments, the cancer is selected from the group consisting of: lung cancer, pancreas cancer, myeloma, myeloid leukemia, meningioma, glioblastoma, breast cancer, esophageal squamous cell carcinoma, gastric adenocarcinoma, prostate cancer, bladder cancer, ovarian cancer, thyroid cancer, neuroendocrine cancer, colon carcinoma, ovarian cancer, head and neck cancer, Hodgkin's Disease, non-Hodgkin's lymphomas, rectum cancer, urinary cancers, uterine cancers, oral cancers, skin cancers, stomach cancer, brain tumors, liver cancer, laryngeal cancer, esophageal cancer, mammary tumors, fibrosarcoma, myxosarcoma, liposarcoma, chondrosarcoma, osteogenic sarcoma, chordoma, angiosarcoma, endotheliosarcoma, Ewing's sarcoma, squamous cell carcinoma, basal cell carcinoma, adenocarcinoma, sweat gland carcinoma, sebaceous gland carcinoma, papillary carcinoma, papillary adenocarcinomas, cystandeocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, endometrial cancer, lung carcinoma, small cell lung carcinoma, bladder carcinoma, epithelial carcinoma, glioblastomas, neuronomas, craniopharingiomas, schwannomas, glioma, astrocytoma, meningioma, melanoma, neuroblastoma, retinoblastoma, leukemias and lymphomas, acute lymphocytic leukemia and acute myelocytic polycythemia vera, multiple myeloma, Waldenstrom's macroglobulinemia, and heavy chain disease, acute nonlymphocytic leukemias, chronic lymphocytic leukemia, chronic myelogenous leukemia, childhood-null acute lymphoid leukemia (ALL), thymic ALL, B-cell ALL, acute megakaryocytic leukemia, Burkitt's lymphoma, and T cell leukemia, small and large non-small cell lung carcinoma, acute granulocytic leukemia, germ cell tumors, endometrial cancer, gastric cancer, hairy cell leukemia, thyroid cancer and other cancers known in the art. In some embodiments, the biological state is a pre-disease state.

Various aspects of the present disclosure provide a method for distinguishing a biological state of a complex biological sample, the method comprising: providing the complex biological sample to an automated apparatus to generate a subset of biomolecules; assaying the subset of biomolecules to generate a biomolecule fingerprint; and distinguishing a biological state of the complex biological sample with the biomolecule fingerprint.

In some embodiments, the biomolecule fingerprint comprises proteins. In some embodiments, the subset of biomolecules from the complex biological sample comprises a lower ratio of albumin to non-albumin peptides than the complex biological sample. In some embodiments, the subset of biomolecules comprises biomolecules that span at least 6 to at least 12 orders of magnitude in concentration range in the complex biological sample. In some embodiments, the subset of biomolecules comprises proteins that span at least 6 to at least 12 orders of magnitude in concentration range in the complex biological sample. In some embodiments, the biomolecule fingerprint comprises from 1 to 74,000 protein groups.

In some embodiments, the assaying comprises desorbing a plurality of biomolecules from a biomolecule corona from among the plurality of biomolecule coronas. In some embodiments, the assaying comprises chemically modifying a biomolecule from among the plurality of desorbed biomolecules. In some embodiments, the assaying comprises fragmenting a biomolecule from among the plurality of desorbed biomolecules. In some embodiments, the fragmenting comprises protease digestion. In some embodiments, the fragmenting comprises chemical peptide cleavage.

In some embodiments, the assaying comprises collecting the plurality of desorbed biomolecules. In some embodiments, the assaying comprises purifying the collected plurality of desorbed biomolecules. In some embodiments, the purifying comprises solid-phase extraction. In some embodiments, the purifying depletes non-protein biomolecules from the collected plurality of desorbed biomolecules. In some embodiments, the assaying comprises discarding the plurality of desorbed biomolecules. In some embodiments, the assaying comprises desorbing a first subset of biomolecules and a second set of biomolecules from a biomolecule corona from among the plurality of biomolecule coronas, analyzing a biomolecule from among the first subset of biomolecules, and analyzing a biomolecule from among the second subset of biomolecules.

In some embodiments, the assaying comprises analyzing a biomolecule corona from among the plurality of biomolecule coronas with mass spectrometry, tandem mass spectrometry, mass cytometry, mass cytometry, potentiometry, fluorimetry, absorbance spectroscopy, Raman spectroscopy, chromatography, electrophoresis, immunohistochemistry, PCR, next generation sequencing (NGS), or any combination thereof. In some embodiments, the assaying comprises mass spectrometry or tandem mass spectrometry. In some embodiments, the assaying comprises identifying the conformational state of a protein from among the subset of biomolecules. In some embodiments, the assaying comprises identifying a post-translational modification on a protein from among the subset of biomolecules. In some embodiments, the distinguishing comprises comparing the relative abundances of at least 200 to at least 1000 biomolecules from the subset of biomolecules. In some embodiments, the assaying identifies biomolecules at concentrations of less than 10 ng/mL in the complex biological sample.

Various aspects of the present disclosure provide an automated apparatus for generating a subset of biomolecules from a complex biological sample, the automated apparatus comprising: a plurality of particles and the complex biological sample, wherein the automated apparatus is configured to generate the subset of biomolecules by contacting the plurality of particles with the complex biological sample to form a plurality of biomolecule coronas comprising the subset of biomolecules, and wherein a dynamic range of the subset of biomolecules is compressed relative to a dynamic range of biomolecules present in the complex biological sample. In some embodiments, the automated apparatus comprises a substrate. In some embodiments, the substrate comprises a multi-well plate. In some embodiments, the substrate is a multi-well plate. In some embodiments, the automated apparatus generates the subset of biomolecules from a complex biological sample in less than 7 hours.

In some embodiments, the automated apparatus comprises an incubation element. In some embodiments, the incubation element is configured to heat and/or incubate the plurality of particles and the complex biological sample to a temperature between 4° C. and 40° C.

In some embodiments, the automated apparatus comprises at least one solution selected from the group consisting of a wash solution, a resuspension solution, a denaturing solution, a buffer and a reagent. In some embodiments, the resuspension solution comprises a Tris EDTA buffer, a phosphate buffer, and/or water. In some embodiments, the denaturing solution comprises a protease. In some embodiments, the denaturing solution comprises a small molecule capable of performing peptide cleavage.

In some embodiments, the automated apparatus comprises a loading unit comprising a plurality of pipettes. In some embodiments, each pipette of the plurality of pipettes is configured to dispense about 5 uL-150 uL of the solution, the complex biological sample, and/or the plurality of particles. In some embodiments, the complex biological sample comprises plasma, serum, urine, cerebrospinal fluid, synovial fluid, tears, saliva, whole blood, milk, nipple aspirate, ductal lavage, vaginal fluid, nasal fluid, ear fluid, gastric fluid, pancreatic fluid, trabecular fluid, lung lavage, sweat, crevicular fluid, semen, prostatic fluid, sputum, fecal matter, bronchial lavage, fluid from swabbings, bronchial aspirants, fluidized solids, fine needle aspiration samples, tissue homogenates, lymphatic fluid, cell culture samples, or any combination thereof. In some embodiments, the automated apparatus comprises a magnet. In some embodiments, the automated apparatus comprises a filter.

In some embodiments, the compressed dynamic range comprises an increase in the number of types of biomolecules whose concentrations are within 4 to 6 orders of magnitude of the most abundant biomolecule in the sample. In some embodiments, the types of biomolecules comprises protein. In some embodiments, the dynamic range of the biomolecules of the biomolecule coronas is a first ratio of a top decile of biomolecules to a bottom decile of biomolecules in the plurality of biomolecule coronas. In some embodiments, the generating enriches low abundance biomolecules from the complex biological sample. In some embodiments, the low abundance biomolecules are biomolecules at concentrations of 10 ng/mL or less in the complex biological sample.

In some embodiments, at least two particles from among the plurality of particles differ in at least one physicochemical property. In some embodiments, the at least one physicochemical property is selected from the group consisting of: composition, size, surface charge, hydrophobicity, hydrophilicity, surface functionality, surface topography, surface curvature, porosity, core material, shell material, shape, and any combination thereof. In some embodiments, a particle from among the plurality of particles is selected from the group consisting of: micelles, liposomes, iron oxide particles, silver particles, gold particles, palladium particles, quantum dots, platinum particles, titanium particles, silica particles, metal or inorganic oxide particles, synthetic polymer particles, copolymer particles, terpolymer particles, polymeric particles with metal cores, polymeric particles with metal oxide cores, polystyrene sulfonate particles, polyethylene oxide particles, polyoxyethylene glycol particles, polyethylene imine particles, polylactic acid particles, polycaprolactone particles, polyglycolic acid particles, poly (lactide-co-glycolide polymer particles, cellulose ether polymer particles, polyvinylpyrrolidone particles, polyvinyl acetate particles, polyvinylpyrrolidone-vinyl acetate copolymer particles, polyvinyl alcohol particles, acrylate particles, polyacrylic acid particles, crotonic acid copolymer particles, polyethylene phosphonate particles, polyalkylene particles, carboxy vinyl polymer particles, sodium alginate particles, carrageenan particles, xanthan gum particles, gum acacia particles, Arabic gum particles, guar gum particles, pullulan particles, agar particles, chitin particles, chitosan particles, pectin particles, karaya tum particles, locust bean gum particles, maltodextrin particles, amylose particles, corn starch particles, potato starch particles, rice starch particles, tapioca starch particles, pea starch particles, sweet potato starch particles, barley starch particles, wheat starch particles, hydroxypropylated high amylose starch particles, dextrin particles, levan particles, elsinan particles, gluten particles, collagen particles, whey protein isolate particles, casein particles, milk protein particles, soy protein particles, keratin particles, polyethylene particles, polycarbonate particles, polyanhydride particles, polyhydroxyacid particles, polypropylfumerate particles, polycaprolactone particles, polyamine particles, polyacetal particles, polyether particles, polyester particles, poly(orthoester) particles, polycyanoacrylate particles, polyurethane particles, polyphosphazene particles, polyacrylate particles, polymethacrylate particles, polycyanoacrylate particles, polyurea particles, polyamine particles, polystyrene particles, poly(lysine) particles, chitosan particles, dextran particles, poly(acrylamide) particles, derivatized poly(acrylamide) particles, gelatin particles, starch particles, chitosan particles, dextran particles, gelatin particles, starch particles, poly-3-amino-ester particles, poly(amido amine) particles, poly lactic-co-glycolic acid particles, polyanhydride particles, bioreducible polymer particles, and 2-(3-aminopropylamino)ethanol particles, and any combination thereof.

In some embodiments, biomolecules of the biomolecule coronas comprise a number of protein groups. In some embodiments, the number of protein groups comprises from 1 to 20,000 protein groups. In some embodiments, the number of protein groups comprises from 100 to 10,000 protein groups. In some embodiments, the number of protein groups comprises from 100 to 5000 protein groups. In some embodiments, the number of proteins groups comprises from 300 to 2,200 protein groups. In some embodiments, the number of proteins groups comprises from 1,200 to 2,200 protein groups.

In some embodiments, the automated apparatus comprises a purification unit. In some embodiments, the purification unit comprises a solid phase extraction (SPE) plate.

Various aspects of the present disclosure provide a method for generating a subset of biomolecules from a complex biological sample, the method comprising: providing the complex biological sample to an automated apparatus, wherein the automated apparatus contacts the complex biological sample with a plurality of particles to generate biomolecule coronas, wherein the automated apparatus processes the biomolecule coronas to generate the subset of biomolecules, and wherein a dynamic range of the subset of biomolecules is compressed relative to a dynamic range of biomolecules present in the complex biological sample.

In some embodiments, the method comprises assaying the subset of biomolecules to generate a biomolecule fingerprint. In some embodiments, the assaying identifies biomolecules at concentrations of less than 10 ng/mL in the complex biological sample. In some embodiments, the assaying comprises analyzing biomolecule coronas with mass spectrometry, tandem mass spectrometry, mass cytometry, mass cytometry, potentiometry, fluorimetry, absorbance spectroscopy, Raman spectroscopy, chromatography, electrophoresis, immunohistochemistry, or any combination thereof. In some embodiments, the assaying comprises mass spectrometry or tandem mass spectrometry.

In some embodiments, the method comprises distinguishing a biological state of the complex biological sample with the biomolecule fingerprint. In some embodiments, the biomolecule fingerprint comprises a plurality of distinct biomolecule corona signatures. In some embodiments, the biomolecule fingerprint comprises at least 5, 10, 20, 40, or 80, 150 or 200 distinct biomolecule corona signatures. In some embodiments, the biological state is a disease, disorder, or tissue abnormality. In some embodiments, the disease is an early phase or intermediate phase disease state. In some embodiments, the disease is cancer. In some embodiments, the cancer is a stage 0 cancer or a stage 1 cancer. In some embodiments, the cancer is selected from the group consisting of: lung cancer, pancreas cancer, myeloma, myeloid leukemia, meningioma, glioblastoma, breast cancer, esophageal squamous cell carcinoma, gastric adenocarcinoma, prostate cancer, bladder cancer, ovarian cancer, thyroid cancer, neuroendocrine cancer, colon carcinoma, ovarian cancer, head and neck cancer, Hodgkin's Disease, non-Hodgkin's lymphomas, rectum cancer, urinary cancers, uterine cancers, oral cancers, skin cancers, stomach cancer, brain tumors, liver cancer, laryngeal cancer, esophageal cancer, mammary tumors, fibrosarcoma, myxosarcoma, liposarcoma, chondrosarcoma, osteogenic sarcoma, chordoma, angiosarcoma, endotheliosarcoma, Ewing's sarcoma, squamous cell carcinoma, basal cell carcinoma, adenocarcinoma, sweat gland carcinoma, sebaceous gland carcinoma, papillary carcinoma, papillary adenocarcinomas, cystandeocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, endometrial cancer, lung carcinoma, small cell lung carcinoma, bladder carcinoma, epithelial carcinoma, glioblastomas, neuronomas, craniopharingiomas, schwannomas, glioma, astrocytoma, meningioma, melanoma, neuroblastoma, retinoblastoma, leukemias and lymphomas, acute lymphocytic leukemia and acute myelocytic polycythemia vera, multiple myeloma, Waldenstrom's macroglobulinemia, and heavy chain disease, acute nonlymphocytic leukemias, chronic lymphocytic leukemia, chronic myelogenous leukemia, childhood-null acute lymphoid leukemia (ALL), thymic ALL, B-cell ALL, acute megakaryocytic leukemia, Burkitt's lymphoma, and T cell leukemia, small and large non-small cell lung carcinoma, acute granulocytic leukemia, germ cell tumors, endometrial cancer, gastric cancer, hairy cell leukemia, or thyroid cancer. In some embodiments, the biological state is a pre-disease state.

Various aspects of the present disclosure provide an automated apparatus to identify proteins in a biological sample, the automated apparatus comprising: a sample preparation unit; a substrate comprising a plurality of channels; a plurality of pipettes; a plurality of solutions, a plurality of nanoparticles, and wherein the automated apparatus is configured to form a protein corona and digest the protein corona.

Various aspects of the present disclosure provide an automated apparatus to identify proteins in a biological sample, the automated apparatus comprising: a sample preparation unit; a substrate comprising a plurality of channels; a plurality of pipettes; a plurality of solutions, a plurality of nanoparticles, wherein the automated apparatus is configured to form a protein corona and digest the protein corona, and wherein at least one of the solutions is TE 150 mM KCl 0.05% CHAPS buffer.

In some aspects, the sample preparation unit is configured to add the plurality of nanoparticles to the substrate with the plurality of pipettes. In some aspects, the sample preparation unit is configured to add the biological sample to the substrate with the plurality of pipettes. In some aspects, the sample preparation unit is configured to incubate the plurality of nanoparticles and the biological sample to form the protein corona. In some aspects, the sample preparation unit is configured to separate the protein corona from the supernatant to form a protein corona pellet. In some aspects, the sample preparation unit is configured to reconstitute the protein corona pellet with TE 150 mM KCl 0.05% CHAPS buffer.

In some aspects, the automated apparatus comprises a magnetic source. In some aspects, the automated apparatus is configured for BCA, gel, or trypsin digestion of the protein corona. In some aspects, the automated apparatus is enclosed. In some aspects, the automated apparatus is sterilized before use. In some aspects, the automated apparatus is configured to a mass spectrometry. In some aspects, the automated apparatus is temperature controlled.

Various aspects of the present disclosure provide a method of identifying proteins in a biological sample, the method comprising: adding the biological sample to an automated apparatus; generating proteomic data from the automated apparatus; and quantifying the proteomic data. In some embodiments, the method further comprises incubating a plurality of nanoparticles with the biological sample in the automated apparatus to form a protein corona. In some embodiments, the method further comprises separating the protein corona from the supernatant in the automated apparatus. In some embodiments, the method further comprises digesting the protein corona to form the digested sample in the automated apparatus. In some embodiments, the method further comprises washing the digested sample in the automated apparatus. In some embodiments, quantifying the proteomic data comprises providing the proteomic data to a mass spectrometry. In some embodiments, the biological sample is a biofluid. In some embodiments, the biofluid is serum or plasma.

In some aspects, the present disclosure provides an automated system comprising a network of units with differentiated functions in distinguishing states of a complex biological sample using a plurality of particles having surfaces with different physicochemical properties wherein: a first unit comprises a multichannel fluid transfer instrument for transferring fluids between units within the system; a second unit comprises a support for storing a plurality of biological samples; a third unit comprises a support for a sensor array plate possessing partitions that comprise the plurality of particles having surfaces with different physicochemical properties for binding a population of analytes within the complex biological sample; a fourth unit comprises supports for storing a plurality of reagents; a fifth unit comprises supports for storing a reagent to be disposed of; a sixth unit comprises supports for storing consumables used by the multichannel fluid transfer instrument; and wherein the system is programmed to perform a series of steps comprising: contacting the complex biological sample with a specified partition of the sensor array; incubating the complex biological sample with the plurality of particles contained within the partition of the sensor array plate; removing all components from a partition except the plurality of particles and a population of analytes interacting with a particle; and preparing a sample for mass spectrometry.

In some embodiments, the first unit comprises a degree of mobility that enables access to all other units within the system. In some embodiments, the first unit comprises a capacity to perform pipetting functions.

In some embodiments, the support of the second and/or third unit comprises support for a single plate, a 6 well plate, a 12 well plate, a 96 well plate, or a rack of microtubes. In some embodiments, the second and/or unit comprises a thermal unit capable of modulating the temperature of said support and a sample. In some embodiments, the second and/or third unit comprises a rotational unit capable of physically agitating and/or mixing a sample.

In some embodiments, the plurality of particles having surfaces with different physicochemical properties for binding a population of analytes within the complex biological sample are immobilized to a surface within a partition of the sensory array. In some embodiments, the plurality of particles comprises a plurality of magnetic nanoparticles with different physicochemical properties for binding a population of analytes within the complex biological sample. In some embodiments, the system comprises a step wherein the sensor array plate is transferred to an additional seventh unit that comprises a magnetized support and a thermal unit capable of modulating the temperature of said support and a sample and incubated for an additional amount of time.

In some embodiments, the fourth unit comprises a set of reagents for: generating the sensor array plate; washing an unbound sample; and/or preparing a sample for mass spectrometry. In some embodiments, contacting the biological sample with a specified partition of the sensor array comprises pipetting a specified volume of the biological sample into the specific partition of the sensor array. In some embodiments, contacting the biological sample with a specified partition of the sensor array comprises pipetting a volume corresponding to a 1:1, 1:2: 1:3, 1:4, 1:5, 1:6, 1:7, 1:8, 1:9, 1:10, 1:15, or 1:20 ratio of a plurality of particles in a solution to the biological sample.

In some embodiments, contacting the biological sample with a specified partition of the sensor array comprises pipetting a volume of at least 10 microliters, at least 50 microliters, at least 100 microliters, at least 250 microliters, at least 500 microliters, or at least 1000 microliters the biological sample into the specific partition of the sensor array.

In some embodiments, incubating the biological sample with the plurality of particles contained within the partition of the sensor array plate comprises an incubation time of at least about 10 seconds, at least about 15 seconds, at least about 20 seconds, at least about 25 seconds, at least about 30 seconds, at least about 40 seconds, at least about 50 seconds, at least about 60 seconds, at least about 90 seconds, at least about 2 minutes, at least about 3 minutes, at least about 4 minutes, at least about 5 minutes, at least about 6 minutes, at least about 7 minutes, at least about 8 minutes, at least about 9 minutes, at least about 10 minutes, at least about 15 minutes, at least about 20 minutes, at least about 25 minutes, at least about 30 minutes, at least about 45 minutes, at least about 50 minutes, at least about 60 minutes, at least about 90 minutes, at least about 2 hours, at least about 3 hours, at least about 4 hours, at least about 5 hours, at least about 6 hours, at least about 7 hours, at least about 8 hours, at least about 9 hours, at least about 10 hours, at least about 12 hours, at least about 14 hours, at least about 15 hours, at least about 16 hours, at least about 17 hours, at least about 18 hours, at least about 19 hours, at least about 20 hours, or at least about 24 hours.

In some embodiments, incubating the biological sample with the plurality of particles contained within the partition of the substrate comprises an incubation temperature between about 4° C. to about 40° C. Incubating the biological sample with the plurality of particles contained within the partition of the substrate may comprise an incubation temperature between about 4° C. to about 37° C. Incubating the biological sample with the plurality of particles contained within the partition of the substrate may comprise an incubation temperature between about 4° C. to about 100° C.

In some embodiments, removing all components from a partition except the plurality of particles and a population of analytes interacting with a particle comprises a series of wash steps.

In some embodiments, the second unit can facilitate a transfer of the sample for mass spectrometry to a mass spectrometry unit.

In some aspects, the present disclosure provides an automated apparatus to identify proteins in a biological sample, the automated apparatus comprising: a sample preparation unit; a substrate comprising a plurality of channels; a plurality of pipettes; a plurality of solutions, a plurality of nanoparticles, and wherein the automated apparatus is configured to form a protein corona and digest the protein corona.

In some aspects, the present disclosure provides an automated apparatus to identify proteins in a biological sample, the automated apparatus comprising: a sample preparation unit; a substrate comprising a plurality of channels; a plurality of pipettes; a plurality of solutions, a plurality of nanoparticles, wherein the automated apparatus is configured to form a protein corona and digest the protein corona, and wherein at least one of the solutions is TE 150 mM KCl 0.05% CHAPS buffer.

In some embodiments, the sample preparation unit is configured to add the plurality of nanoparticles to the substrate with the plurality of pipettes. In some embodiments, wherein the sample preparation unit is configured to add the biological sample to the substrate with the plurality of pipettes. In some embodiments, the sample preparation unit is configured to incubate the plurality of nanoparticles and the biological sample to form the protein corona.

In some embodiments, the sample preparation unit is configured to separate the protein corona from the supernatant to form a protein corona pellet. In some embodiments, the sample preparation unit is configured to reconstitute the protein corona pellet with TE 150 mM KCl 0.05% CHAPS buffer.

In some embodiments, the automated apparatus further comprises a magnetic source. In some embodiments, the automated apparatus is configured for BCA, gel, or trypsin digestion of the protein corona.

In some embodiments, the automated apparatus is enclosed. In some embodiments, the automated apparatus is sterilized before use. In some embodiments, the automated apparatus is configured to a mass spectrometry. In some embodiments, the automated apparatus is temperature controlled.

In some aspects, the present disclosure provides a method of identify proteins in a biological sample, the method comprising: adding the biological sample to the automated apparatus disclosed herein; generating proteomic data from the automated apparatus; and quantifying the proteomic data.

In some embodiments, the method further comprises incubating a plurality of nanoparticles with the biological sample in the automated apparatus to form a protein corona. In some embodiments, the method further comprises separating the protein corona from the supernatant in the automated apparatus. In some embodiments, the method further comprises digesting the protein corona to form the digested sample in the automated apparatus.

In some embodiments, the method further comprises washing the digested sample in the automated apparatus. In some embodiments, quantifying the proteomic data comprises providing the proteomic data to a mass spectrometry.

In some embodiments, the biological sample is a biofluid. In some embodiments, the biofluid is serum or plasma.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 7 shows surface chemistries for magnetic nanoparticle sensor arrays.

DETAILED DESCRIPTION

Figure 1:
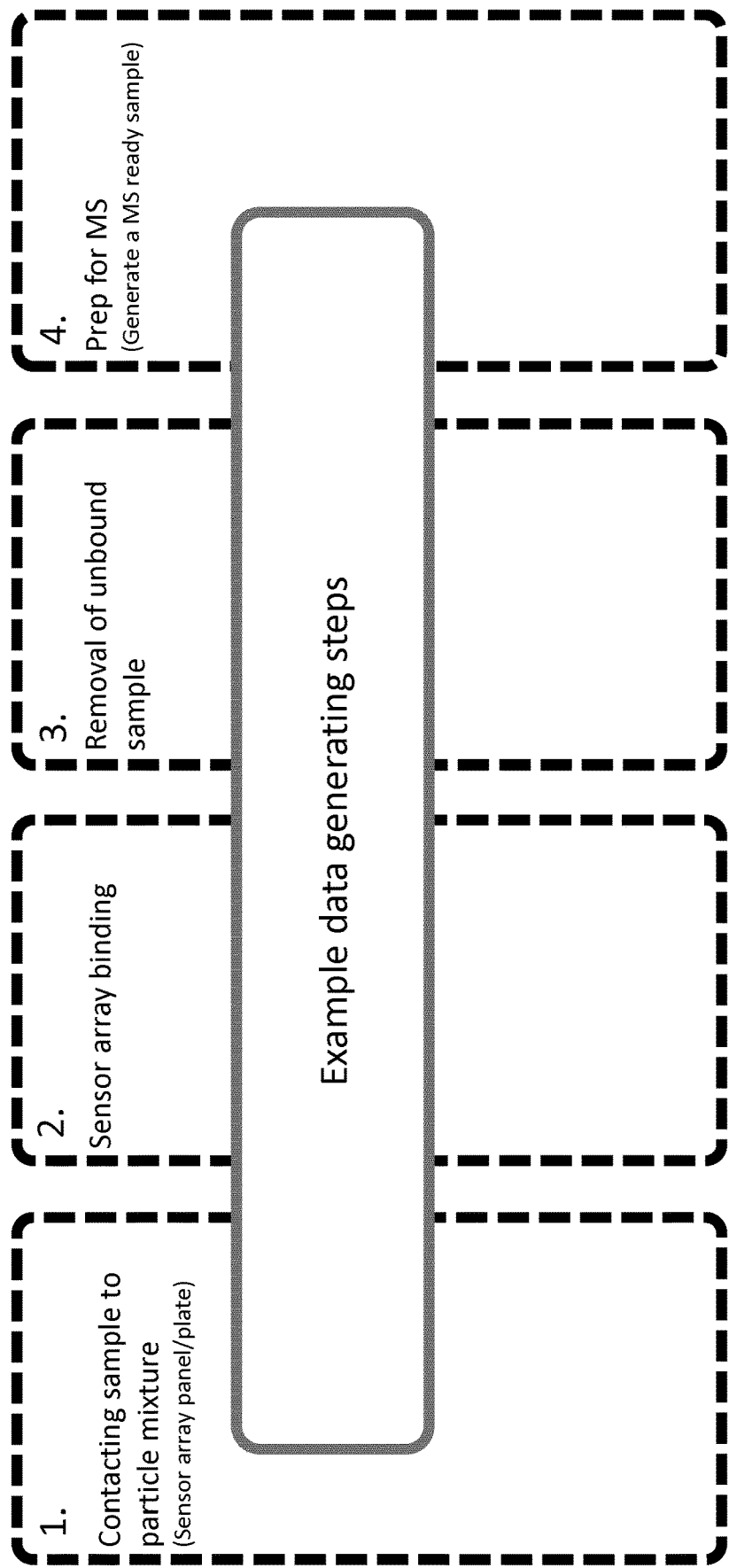
FIG. 1 shows a schematic illustration of the steps for generating data using nanoparticle or protein corona methods.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

As used herein, a "feature" identified by mass spectrometry includes a signal at a specific combination of retention time and m/z (mass-to-charge ratio), where each feature has an associated intensity. Some features are further fragmented in a second mass spectrometry analysis (MS2) for identification.

As used herein, the term "sensor element" refers to elements that are able to bind to a plurality of biomolecules when in contact with a sample and encompasses the term "nanoscale sensor element". A sensor element may be a particle, such as a nanoparticle, or microparticle. A sensor element may be a surface or a portion of a surface. A sensor element may comprise a particle or plurality of particles. A sensor element may comprise a plurality of surfaces capable of adsorbing or binding biomolecules. A sensor element may comprise a porous material, such as a material into which biomolecules can intercalate.

As used herein, a "sensor array" may comprise a plurality of sensor elements wherein the plurality of sensor elements (e.g., particles) comprises multiple types of sensor elements. The sensor elements may be different types that differ from each other in at least one physicochemical property. A sensor array may be a substrate with a plurality of partitions containing a plurality of sensor elements (e.g., particles). For example, a sensor array may comprise a multi-well plate with a plurality of particles distributed between the plurality of wells. A sensor array may be a substrate comprising a plurality of partitions, wherein the plurality of partitions comprises a plurality of particles. In some embodiments, each sensor element or particle is able to bind a plurality of biomolecules in a sample to produce a biomolecule corona signature. In some embodiments, each sensor element (e.g., particle type) has a distinct biomolecule corona signature.

As used herein, the term "biomolecule corona" refers to the plurality of different biomolecules that bind to a sensor element. The term "biomolecule corona" may refer to the proteins, lipids and other plasma components that bind to particles (e.g., nanoparticles) when they come into contact with biological samples or biological system. For use herein, the term "biomolecule corona" also encompasses both the soft and hard protein corona as referred to in Milani et al. "Reversible versus Irreversible Binding of Transferring to Polystyrene Nanoparticles: Soft and Hard Corona" ACS NANO, 2012, 6(3), pp. 2532-2541; Mirshafiee et al. "Impact of protein pre-coating on the protein corona composition and nanoparticle cellular uptake" Biomaterials vol. 75, January 2016 pp. 295-304, Mahmoudi et al. "Emerging understanding of the protein corona at the nano-bio interfaces" Nanotoday 11(6) December 2016, pp. 817-832, and Mahmoudi et al. "Protein-Nanoparticle Interactions: Opportunities and Challenges" Chem. Rev., 2011, 111(9), pp. 5610-5637, the contents of which are incorporated by reference in their entireties. As described therein, an adsorption curve may show the build-up of a strongly bound monolayer up to the point of monolayer saturation (at a geometrically defined protein-to-NP ratio), beyond which a secondary, weakly bound layer is formed. While the first layer is irreversibly bound (hard corona), the secondary layer (soft corona) may exhibit dynamic exchange. Proteins that adsorb with high affinity may form the "hard" corona, comprising tightly bound proteins that do not readily desorb, and proteins that adsorb with low affinity may form the "soft" corona, comprising loosely bound proteins. Soft and hard corona can also be characterized based on their exchange times. Hard corona may show much larger exchange times in the order of several hours. See, e.g., M. Rahman et al. Protein-Nanoparticle Interactions, Spring Series in Biophysics 15, 2013, incorporated by reference in its entirety.

The term "biomolecule" refers to biological components that may be involved in corona formation, including, but not limited to, for example, proteins, polypeptides, polysaccharides, a sugar, a lipid, a lipoprotein, a metabolite, an oligonucleotide, metabolome or combination thereof. It is contemplated that the biomolecule coronas of distinct particles may contain some of the same biomolecules, may contain distinct biomolecules with regard to the other sensor elements, and/or may differ in level or quantity, type or conformation of the biomolecule that binds to each sensor element. In one embodiment, the biomolecule is selected from the group of proteins, nucleic acids, lipids, and metabolomes.

The term "biomolecule corona signature" refers to the composition, signature or pattern of different biomolecules that are bound to each type of particle or separate sensor element. The signature may not only refers to the different biomolecules but also the differences in the amount, level or quantity of the biomolecule bound to the sensor element, or differences in the conformational state of the biomolecule that is bound to the particle or sensor element. It is contemplated that the biomolecule corona signatures of each distinct type of sensor elements may contain some of the same biomolecules, may contain distinct biomolecules with regard to the other sensor elements, and/or may differ in level or quantity, type or conformation of various biomolecules. The biomolecule corona signature may depend on not only the physicochemical properties of the sensor element (e.g., particle), but also the nature of the sample and the duration of exposure to the biological sample.

Disclosed herein are compositions and methods for multiomic analysis. "Multi-omic(s)" or "multiomic(s)" can refer to an analytical approach for analyzing biomolecules at a large scale, wherein the data sets are multiple omes, such as proteome, genome, transcriptome, lipidome, and metabolome. Non-limiting examples of multi-omic data include proteomic data, genomic data, lipidomic data, glycomic data, transcriptomic data, or metabolomics data.

"Biomolecule" in "biomolecule corona" can refer to any molecule or biological component that can be produced by, or is present in, a biological organism. Non-limiting examples of biomolecules include proteins (protein corona), polypeptides, oligopeptides, polyketides, polysaccharides, a sugar, a lipid, a lipoprotein, a metabolite, an oligonucleotide, a nucleic acid (DNA, RNA, micro RNA, plasmid, single stranded nucleic acid, double stranded nucleic acid), metabolome, as well as small molecules such as primary metabolites, secondary metabolites, and other natural products, or any combination thereof. In some embodiments, the biomolecule is selected from the group of proteins, nucleic acids, lipids, and metabolomes.

Currently, there are a small number of protein-based biomarkers in use today for clinical diagnosis, and in spite of extensive efforts to analyze the plasma proteome for the expansion of markers, relatively few new candidates have been accepted as clinically useful indicators. The plasma proteome contains >10,000 proteins and potentially an order of magnitude more protein isoforms with a concentration range spanning over 10 orders of magnitude (from mg/mL to pg/mL). These attributes, combined with a lack of convenient molecular tools for proteome analysis, make comprehensive studies of the plasma proteome exceptionally challenging. Approaches to overcome the broad dynamic range of proteins in biological samples must be capable of identifying and quantifying against a background of thousands of unique proteins and even more protein variants. However, there are no existing technologies that are capable of simultaneous measurement of proteins across the entire plasma concentration range in a format with a sufficient throughput and with a practical cost profile to allow for appropriately-sized studies with robust prospects for validation and replication. These challenges not only limit the discovery of novel disease biomarkers, but have been a bottleneck against the adoption of proteogenomics and protein annotation of genomic variants. Advances in mass spectrometry (MS) along with development of improved data analytics have offered tools for deep and broad proteomic analysis. Several attempts have been made to substantially improve the detection of low abundance proteins, such as depletion of highly abundant proteins, plasma fractionation, and peptide fractionation. It is now possible to identify over 4,500 proteins in plasma. However, current approaches are fairly complex and time-consuming (days to weeks), and thus require a tradeoff between depth of protein coverage and sample throughput. Consequently, a simple and robust strategy for comprehensive and rapid analysis of the available body of information in the proteome remains an unmet need.

Additionally, the earlier a disease is diagnosed, the more likely that the disease can be cured or successfully managed leading to a better prognosis for the patient. When a disease is treated early, it may be possible to prevent or delay problems from the disease and may improve the outcomes for the patient, including extending the patient's life and/or quality of life.

Early diagnosis of cancer is crucial, as many types of cancers can be successfully treated in their early stages. For example, five-year survival after early diagnosis and treatment of breast, ovarian, and lung cancers is 90%, 90%, and 70%, respectively, compared to 15%, 5%, and 10% for patients diagnosed at the most advanced stage of disease. Once cancer cells leave their tissue of origin, successful treatment using available established therapeutics becomes very unlikely. Although recognizing the warning signs of cancers and taking prompt action may lead to early diagnosis, the majority of cancers (e.g., lung) show symptoms only after cancer cells have already invaded the surrounding tissues and metastasized throughout the body. For example, more than 60% of patients with breast, lung, colon, and ovarian cancer have concealed or even metastatic colonies by the time their cancers are detected. Therefore, there is an urgent need for development of an effective approach for early detection of cancer. Such an approach should have the sensitivity to identify a cancer at various stages and the specificity to give a negative result when the person being tested is free of the cancer. There have been extensive efforts to develop methods for early detection of cancers; although huge numbers of risk factors and biomarkers have been introduced, a broadly relevant platform for early detection of a wide range of cancers remains elusive.

As various types of cancers can change the composition of blood plasma—even in their early stages—one promising approach for early detection is molecular blood analysis for biomarkers. Although this strategy has already worked for a few cancers (like PSA for prostate cancer), there are not yet specific biomarkers for early detection of the majority of cancers. For such cancers (e.g., lung), none of the defined candidate circulating biomarkers has been clinically validated, and very few have reached late-stage clinical development. Therefore, there is an urgent need for novel approaches to improve our ability to detect cancer, as well as other diseases, at very early stages.

Automated Sample Preparation

The present disclosure provides systems and methods for automated sample preparation, data generation, protein corona analysis. As is depicted in FIG. 1, the systems and methods can comprise (1) contacting a sample to particles (e.g., in a particle mixture) on a sensor array, substrate, plate, or within partitions on any of the foregoing, (2) allowing biomolecules in the sample to bind to the particles, (3) removing unbound sample from the particles, and (4) preparing a sample for analysis (e.g., using mass spectrometry ("MS")). For example, in (1), a method of the present disclosure can comprise contacting a biological sample to a plurality of particles. In (2), the sample may be incubated with the plurality of particles so as to promote biomolecule adsorption to the particles. In (3), unbound sample may be removed while retaining the particles and the biomolecules adsorbed to the particles. In (4) the adsorbed biomolecules may be desorbed from the particles and preparing them for mass spectrometric analysis by which example data may be generated.

Figure 2:
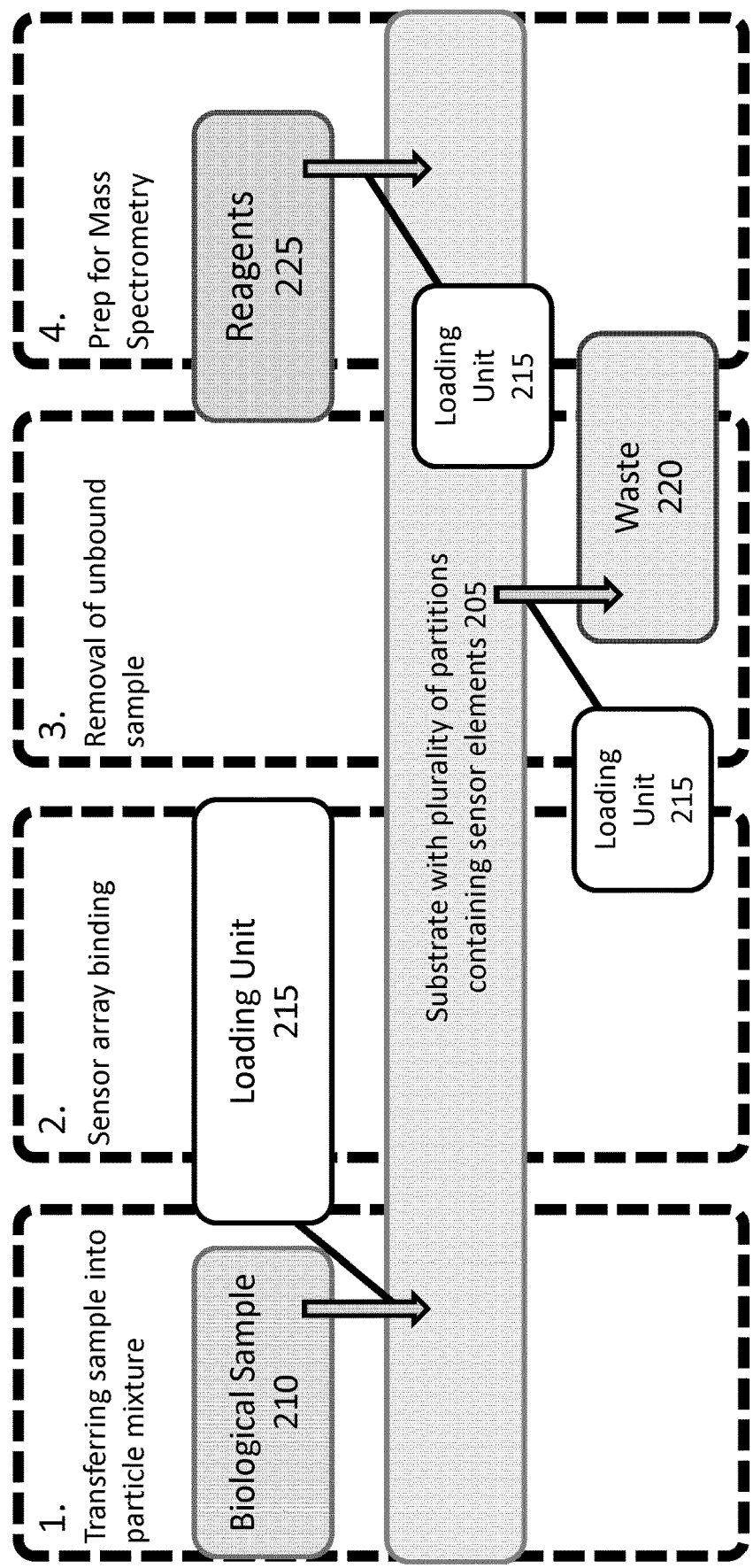
FIG. 2 shows an example illustration of the steps for generating data using nanoparticle or protein corona methods and units of the automated system in which they can take place.

The present disclosure provides automated systems, methods and kits for biomolecule corona preparation and analysis. The automated apparatus may perform at least the aforementioned data generating steps outlined in FIG. 1 using various units illustrated in FIG. 2. The automated apparatus may contain a substrate with a plurality of partitions containing sensor elements 205 and a biological sample 210. The loading unit 215 on the apparatus may transfer a portion of the biological sample 210 into a partition on the substrate 205, leading to adsorption of biomolecules from the biological sample onto a sensor element in the partition on the substrate. The automated apparatus may then remove unbound biomolecules from the partition, optionally transferring the unbound sample into a waste receptacle 220. The remaining biomolecules (e.g., biomolecules adsorbed to the sensor element) may be desorbed, collected, and prepared for mass spectrometric analysis. The reagents 225 may comprise a buffer, such as a resuspension buffer capable of desorbing biomolecules from a biomolecule corona or a denaturation buffer capable of denaturing or fragmenting a biomolecule. Reagents (e.g., a buffer or protease) 225 may also be loaded using the loading unit 215 to facilitate any of the foregoing.

In some aspects, the present disclosure provides an automated system comprising a network of units with differentiated functions in distinguishing states of a complex biological sample using a plurality of particles having surfaces with different physicochemical properties wherein: a first unit comprises a multichannel fluid transfer instrument for transferring fluids between units within the system; a second unit comprises a support for storing a plurality of biological samples; a third unit comprises a support for a sensor array plate (e.g., a substrate comprising a plurality of partitions comprising sensor elements, such as a 96 well plate containing nanoparticles) possessing partitions that comprise the plurality of particles having surfaces with different physicochemical properties for detecting a binding interaction between a population of analytes within the complex biological sample and the plurality of particles; a fourth unit comprises supports for storing a plurality of reagents; a fifth unit comprises supports for storing a reagent to be disposed of; a sixth unit comprises supports for storing consumables used by the multichannel fluid transfer instrument; and wherein the system is programed to perform a series of steps comprising: contacting the biological sample with a specified partition of the sensor array; incubating the biological sample with the plurality of particles contained within the partition of the sensor array plate; removing all components from a partition except the plurality of particles and a population of analytes interacting with a particle; and preparing a sample for mass spectrometry.

Figure 3:
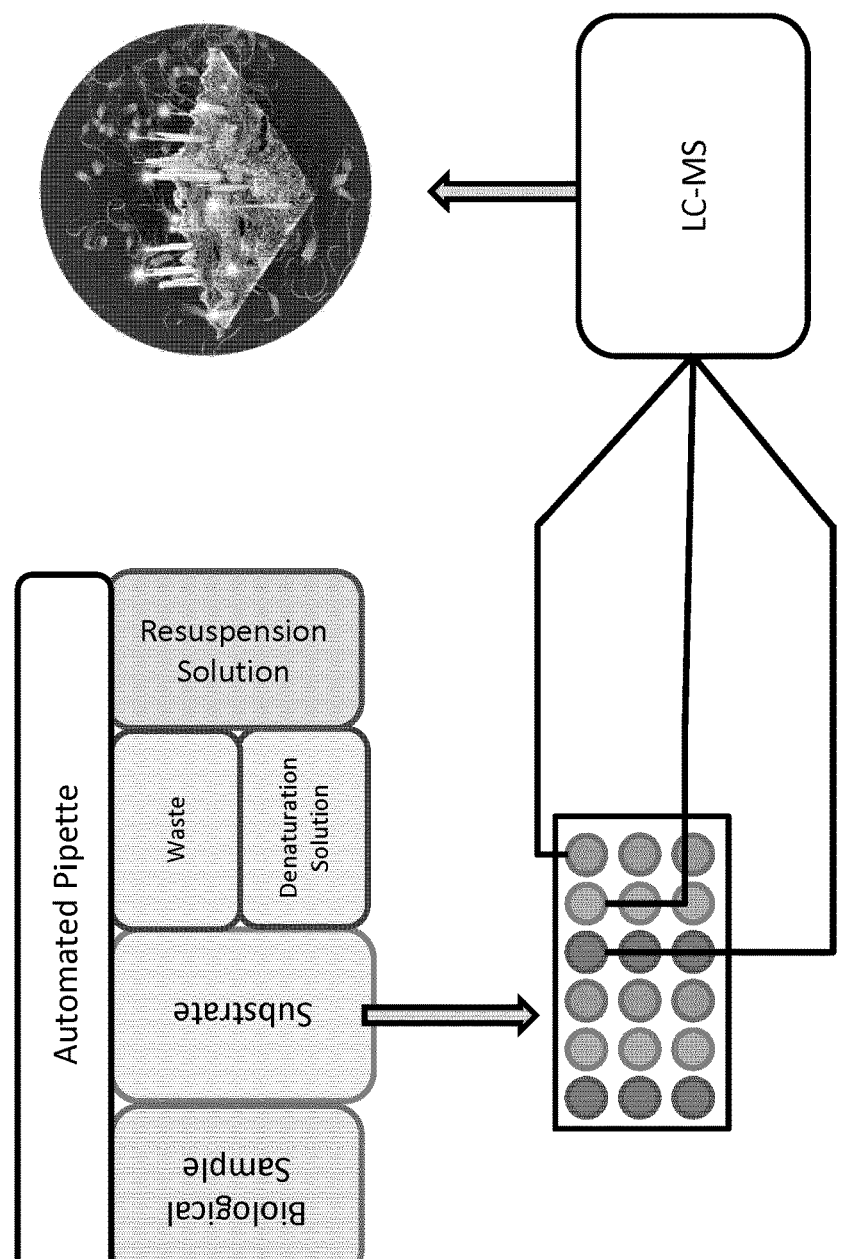
FIG. 3 shows an example layout of the system and coupling to a continuous MS for high throughput applications.

An example of such an apparatus is provided in FIG. 3. The apparatus comprises an automated pipette that is able to transfer volumes between a biological sample storage unit, a substrate comprising a plurality of partitions comprising a plurality of sensor elements, a waste collection unit, a unit comprising a denaturation solution, and a unit comprising a resuspension solution. The automated apparatus can perform a biomolecule corona assay which comprises transferring a portion of the biological sample into a partition within the substrate comprising a sensor element, incubating the portion of the sample with the sensor element to allow biomolecules from the biological sample to bind to the sensor element, removing contents from the partition comprising biomolecules that are not bound to the sensor elements, and then preparing the biomolecules that remained within the partition for mass spectrometric (MS) analysis (e.g., LC-MS).

The loading may comprise a degree of mobility that enables access to all other unit within the system. The loading may comprise a capacity to perform pipetting functions.

The system or apparatus of the present disclosure may comprise support for a single plate, a 6 well plate, a 12 well plate, a 96 well plate, a 192 well plate, a 384 well plate, or a rack of microtubes. In some embodiments, the system or apparatus of the present disclosure may comprise a thermal unit capable of modulating the temperature of said support and a sample. In some embodiments, the system or apparatus of the present disclosure may comprise a rotational unit capable of physically agitating and/or mixing a sample.

In some embodiments, the plurality of particles comprises surfaces with different physicochemical properties for detecting a binding interaction between a population of analytes within the complex biological sample and the plurality of particles are immobilized to a surface with a partition of the sensory array. In some embodiments, the plurality of particles comprises a plurality magnetic nanoparticles in a solution with different physicochemical properties for detecting a binding interaction between a population of analytes within the complex biological sample and the plurality of particles. In some embodiments, the system comprises a step wherein the sensor array plate is transferred to an additional seventh unit that comprises a magnetized support and a thermal unit capable of modulating the temperature of said support and a sample and incubated for an additional amount of time.

In some embodiments, the fourth unit comprises a set of reagents for: generating the sensor array plate; washing an unbound sample; and/or preparing a sample for mass spectrometry. In some embodiments, contacting the biological sample with a specified partition of the sensor array comprises pipetting a specified volume of the biological sample into the specific partition of the sensor array. In some embodiments, contacting the biological sample with a specified partition of the sensor array comprises pipetting a volume corresponding to a 1:1, 1:2: 1:3, 1:4, 1:5, 1:6, 1:7, 1:8, 1:9, 1:10, 1:15, or 1:20 ratio of a plurality of particles in a solution to the biological sample.

In some embodiments, contacting the biological sample with a specified partition of the sensor array comprises pipetting a volume of at least 10 microliters, at least 50 microliters, at least 100 microliters, at least 250 microliters, at least 500 microliters, or at least 1000 microliters the biological sample into the specific partition of the sensor array.

Automated Apparatus

In some aspects, the present disclosure provides an automated apparatus for generating a subset of biomolecules from a biological sample, comprising: a substrate comprising a plurality of partitions, a first unit comprising the biological sample, and a loading unit that is movable across the substrate and is capable of transferring a volume (e.g., a volume of buffer) between different units of the apparatus. In some cases, the substrate is a multi-well plate.

The plurality of partitions may comprise a plurality of sensor elements. The plurality of sensor elements may comprise particles. The plurality of sensor elements may be particles (e.g., nanoparticles or microparticles).

A partition from among the plurality of partitions may comprise 1 to 100 types of sensor elements (e.g., distinct particle types). A partition from among the plurality of partitions may comprise 2 to 50 types of sensor elements. A partition from among the plurality of partitions may comprise 2 to 5 types of sensor elements. A partition from among the plurality of partitions may comprise 3 to 8 types of sensor elements. A partition from among the plurality of partitions may comprise 4 to 10 types of sensor elements. A partition from among the plurality of partitions may comprise 5 to 12 types of sensor elements. A partition from among the plurality of partitions may comprise 6 to 15 types of sensor elements. A partition from among the plurality of partitions may comprise 8 to 20 types of sensor elements.

Two or more partitions from among the plurality of partitions may comprise different quantities of sensor elements. two or more partitions from among the plurality of partitions may comprise different types of sensor elements. A partition amongst a plurality of partitions may comprise a combination of types and/or quantities of sensor element(s) that differs from other partitions in the plurality. A subset of partitions in a plurality of partitions may each contain a combination of distinct sensor elements that is distinct from other partitions in the plurality.

Sensor elements may be stored in dry form inside of or within the partitions. Dry sensor elements may be reconstituted or rehydrated prior to use. Sensor elements may also be stored within solutions. For example, a substrate partition may comprise a solution comprising a high concentration of particles.

Partitions from among the plurality of partitions comprise different concentrations or amounts (e.g., by mass/molar amount per unit volume of sample) of sensor elements. A partition from among the plurality of partitions may comprise from 1 pM to 100 nM of sensor elements. A partition from among the plurality of partitions comprise may from 1 pM to 500 pM of sensor elements. A partition from among the plurality of partitions may comprise from 10 pM to 1 nM of sensor elements. A partition from among the plurality of partitions may comprise from 100 pM to 10 nM of sensor elements. A partition from among the plurality of partitions may comprise from 500 pM to 100 nM of sensor elements. A partition from among the plurality of partitions may comprise from 50 pg/ml to 300 µg/ml of sensor elements. A partition from among the plurality of partitions may comprise from 100 µg/ml to 500 µg/ml of sensor elements. A partition from among the plurality of partitions may comprise from 250 µg/ml to 750 µg/ml of sensor elements. A partition from among the plurality of partitions may comprise from 400 µg/ml to 1 mg/ml of sensor elements. A partition from among the plurality of partitions may comprise from 600 µg/ml to 1.5 mg/ml of sensor elements. A partition from among the plurality of partitions may comprise from 800 µg/ml to 2 mg/ml of sensor elements. A partition from among the plurality of partitions may comprise from 1 mg/ml to 3 mg/ml of sensor elements. A partition from among the plurality of partitions may comprise from 2 mg/ml to 5 mg/ml of sensor elements. A partition from among the plurality of partitions may comprise more than 5 mg/ml of sensor elements.

The loading unit may be configured to move between and transfer volumes (e.g., a volume of a solution or a powder) between any units, compartments, or partitions within the apparatus. The loading unit may be configured to move precise volumes (e.g., within 0.1%, 0.01%, 0.001% of the specified volume). The loading unit may be configured to collect a volume from the substrate or a compartment or partition within the substrate, and dispense the volume back into the substrate or compartment or partition within the substrate, or to dispense the volume or a portion of the volume into a different unit, compartment, or partition. The loading unit may be configured to move multiple volumes simultaneously, such as 2 to 400 separate volumes. The loading unit may comprise a plurality of pipette tips.

The loading unit may be configured to move a volume of a liquid. The volume may be about 0.1 µl, 0.2 µl, 0.3 µl, 0.4 µl, 0.5 µl, 0.6 µl, 0.7 µl, 0.8 µl, 0.9 µl, 1 µl, 2 µl, 3 µl, 4 µl, 5 µl, 6 µl, 7 µl, 8 µl, 9 µl, 10 µl, 12 µl, 15 µl, 20 µl, 25 µl, 30 µl, 40 µl, 50 µl, 60 µl, 70 µl, 80 µl, 90 µl, 100 µl, 120 µl, 150 µl, 180 µl, 200 µl, 250 µl, 300 µl, 400 µl, 500 µl, 600 µl, 800 µl, 1 ml, or more than 1 ml. The liquid may be a biological sample or a solution.

In some cases, the solution comprises a wash solution, a resuspension solution, a denaturing solution, a buffer, a reagent (e.g., a reducing reagent), or any combination thereof. In some cases, the solution comprises a biological sample.

In part owing to these functionalities, the loading unit can be capable of partitioning a sample. In some embodiments, this comprises dividing a sample into a number of partitions. A sample can be divided into at least 2, 3, 4, 5, 6, 7, 8, 9, 10, 12, 15, 20, 25, 30, 40, 50, 60, 70, 80, 90, 100, 120, 150, 180, 200, 250, 300, 350, 400, 500, or more partitions. A sample can be divided into 96, 192, or 384 partitions. The automated apparatus can comprise multiple substrates comprising partitions. The automated apparatus may comprise 1, 2, 3, 4, 5, or more substrates comprising partitions. In some cases, the loading unit loads different volumes of the biological sample into different partitions. In some cases, the loading unit loads identical volumes into two or more partitions. The volume of biological sample loaded into a partition may be about 0.1 µl, 0.2 µl, 0.3 µl, 0.4 µl, 0.5 µl, 0.6 µl, 0.7 µl, 0.8 µl, 0.9 µl, 1 µl, 2 µl, 3 µl, 4 µl, 5 µl, 6 µl, 7 µl, 8 µl, 9 µl, 10 µl, 12 µl, 15 µl, 20 µl, 25 µl, 30 µl, 40 µl, 50 µl, 60 µl, 70 µl, 80 µl, 90 µl, 100 µl, 120 µl, 150 µl, 180 µl, 200 µl, 250 µl, 300 µl, 400 µl, 500 µl, 600 µl, 800 µl, 1 ml, or more than 1 ml. The volume of biological sample loaded into a partition may be about 10 µl to 400 µl. The volume of biological sample loaded into a partition may be about 5 µl to 150 µl. The volume of biological sample loaded into a partition may be about 35 µl to 80 µl. In some cases, the loading unit may partition two or more biological samples. For example, a sample storage unit may comprise two biological samples that the system partitions into one well plate. In some embodiments, the loading unit can facilitate a transfer of the sample for mass spectrometry to a mass spectrometry unit.

The system may be configured to perform a dilution on a sample or a sample partition. A sample or sample partition may be diluted with buffer, water (e.g., purified water), a non-aqueous solvent, or any combination thereof. The diluent may be stored in the automated apparatus prior to dispensation into a substrate partition. The automated apparatus may store a plurality of diluents differing in pH, salinity, osmolarity, viscosity, dielectric constant, or any combination thereof. The diluents may be used to adjust the chemical properties of a sample or sample partition. The automated apparatus may dilute a sample or sample partition by 2-fold, 3-fold, 4-fold, 5-fold, 6-fold, 8-fold, 10-fold, 15-fold, 20-fold, 30-fold, 40-fold, 50-fold, 75-fold, 100-fold, 150-fold, 200-fold, 300-fold, 400-fold, 500-fold or greater. The automated apparatus may perform different dilutions on two samples or sample partitions. The system may perform different dilutions on each partition from among a plurality of partitions. For example, the system may perform different dilutions on each of the 96 sample partitions in a 96 well plate. In some cases, the different dilutions comprise different degrees of dilution (e.g., 2-fold vs. 4-fold). In some cases, the different dilutions comprise dilution with different solutions (e.g., different buffers). In some cases, two sample partitions may be made to differ in one or more chemical properties, such as pH, salinity, or viscosity.

In some cases, the system may modify the chemical composition of a sample or sample partition. The system may modify or adjust the pH, salinity, osmolarity, dielectric constant, viscosity, buffer types, salt types, sugar types, detergent types, or any combination thereof for a sample or sample partition. Such modification or adjustments may comprise mixing a reagent from the fourth unit with a sample or sample partition. The system may differently modify the chemical composition of two samples or sample partitions.

A system or automated apparatus of the present disclosure may also comprise an incubation element. The incubation element may contact, support, or hold another component of the automated apparatus (e.g., the substrate or a unit). The incubation unit may contact, support, or hold multiple components of the automated apparatus. The incubation element may contact the substrate to facilitate heat transfer between the incubation element and the substrate. The incubation unit may be configured to control the temperature of the one or more components of the automated apparatus, such as by heating or cooling. The incubation element may be capable of cooling a component of the apparatus to from 20° C. to 1° C. The incubation element may be capable of heating a component of the apparatus to from 25° C. to 100° C. The incubation element may be capable of setting the temperature a component of the apparatus to from 4° C. to 37° C. The incubation element may be configured to heat or cool different portions of a component of the automated apparatus to different temperatures. For example, the incubation element may hold a first partition in the substrate at 30° C. and a second partition in the substrate at 35° C. The incubation element may control the temperature of a sample or partition. The incubation element may comprise a temperature sensor (e.g., a thermocouple) for detecting the temperature within a partition or container. The incubation element may calibrate its heating or cooling to the readout from the temperature sensor.

The incubation element may be configured to physically agitate a component of the automated apparatus. The agitation may be in the form of shaking or spinning, vibrating, rocking, sonicating, or any combination thereof. The incubation element may be capable of providing multiple agitation intensities and/or frequencies. For example, the incubation element may comprise multiple settings for shaking at different frequencies and amplitudes. The incubation element may also be capable of stirring and or mixing a volume (e.g., a portion of the biological sample).

The automated apparatus may comprise a unit comprising a resuspension solution. The loading unit may be capable of transferring a volume of the resuspension solution to a partition from among the plurality of partitions of the substrate. In some cases, this results in the dilution of a sample present within the partition and can further result in the desorption of a plurality of biomolecules from a biomolecule corona disposed on a sensor element within the partition. The quantity of biomolecules desorbed from a biomolecule corona can depend on the volume of the resuspension solution added to the partition, the temperature of the partition, the composition of the resuspension solution (e.g., the salinity, osmolarity, viscosity, dielectric constant, or pH), the volume of the biological sample within the partition, and the sensor element type and the composition of biomolecules in the biomolecule corona. The transfer of a volume of the resuspension solution into a partition may result in the desorption of less than 5% of the biomolecules from a biomolecule corona. The transfer of a volume of the resuspension solution into a partition may result in the desorption of 10% to 20% of the biomolecules from a biomolecule corona. The transfer of a volume of the resuspension solution into a partition may result in the desorption of 20% to 30% of the biomolecules from a biomolecule corona. The transfer of a volume of the resuspension solution into a partition may result in the desorption of 30% to 40% of the biomolecules from a biomolecule corona. The transfer of a volume of the resuspension solution into a partition may result in the desorption of 40% to 50% of the biomolecules from a biomolecule corona. The transfer of a volume of the resuspension solution into a partition may result in the desorption of 50% to 60% of the biomolecules from a biomolecule corona. The transfer of a volume of the resuspension solution into a partition may result in the desorption of 60% to 70% of the biomolecules from a biomolecule corona. The transfer of a volume of the resuspension solution into a partition may result in the desorption of 70% to 80% of the biomolecules from a biomolecule corona. The transfer of a volume of the resuspension solution into a partition may result in the desorption of 80% to 90% of the biomolecules from a biomolecule corona. The transfer of a volume of the resuspension solution into a partition may result in the desorption of more than 90% of the biomolecules from a biomolecule corona.

In some cases, multiple rounds of desorption are performed. In each round, the supernatant comprising the desorbed biomolecules may be collected, analyzed, or discarded. The types and abundances of biomolecules in the supernatant may differ between desorption rounds. The automated apparatus may perform one or more desorption and discard cycles (i.e., washes), followed by one or more desorption cycles comprising sample collection and/or analysis.

The resuspension solution may be tailored to optimize enrichment of particular biomarkers. The resuspension solution may comprise a buffer, such as Tris-EDTA (TE), CHAPS, PBS, citrate, HEPES, MES, CHES, or another bio buffer. The resuspension solution may comprise Tris EDTA (TE) 150 mM KCl 0.05% CHAPS buffer. The resuspension solution may comprise 10 mM TrisHCl pH 7.4, 1 mM EDTA. The resuspension solution may also contain or be highly purified water (e.g., distilled or deionized water). Biomolecule desorption may be augmented by heating or agitation by an incubation element. The supernatant may be transferred to a new partition following desorption. A resuspension solution may be used to dilute a sample.

The automated apparatus may comprise a unit comprising a denaturing solution. The denaturing solution may comprise a protease. The denaturing solution may comprise a chemical capable of performing peptide cleavage (e.g., cyanogen bromide, formic acid, or hydroxylamine, 2-nitro-5-thiocyanatobenzoic acid). The denaturing solution may comprise a chemical denaturant such as guanidine, urea, sodium deoxycholate, acetonitrile, trichloroacetic acid, acetic acid, sulfosalicylic acid, sodium bicarbonate, ethanol, perchlorate, dodecyl sulfate, or any combination thereof. The denaturing solution may comprise a reductant, such as 2-mercaptoethanol, dithiothreitol, or tris(2-carboxyethyl) phosphine. The protease may be trypsin. The denaturing solution may be added to a partition following desorption. The denaturing solution may be added to a partition comprising biomolecule coronas.

The automated apparatus may comprise a magnet or array of magnets. The automated apparatus may capable of moving the substrate onto and off of the magnet or array of magnets. The array of magnets may be structured so that a plurality of magnets from the array of magnets can rest directly underneath underneath a plurality of partitions from the substrate. The magnet may be capable of immobilizing magnetic sensor elements (e.g., magnetic particles such as coated or uncoated super paramagnetic iron oxide nanoparticles) within a partition on the substrate. For example, the magnet may prevent magnetic nanoparticles from being removed from a partition during a wash step. The magnet may also create a pellet from a collection of magnetic particles. The magnet may create a particle pellet in less than 10 minutes. The magnet may create a particle pellet in less than 5 minutes. The particle pellet may comprise a particle with a biomolecule corona.

The automated apparatus may comprise a purification unit. The purification unit may comprise a plurality of partitions comprising an adsorbent or resin. The purification unit may comprise a solid-phase extraction array or plate. The solid-phase extraction array or plate may comprise a polar stationary phase material. The solid-phase extraction array or plate may comprise a non-polar stationary phase material. The solid-phase extraction array or plate may comprise a C18 stationary phase material (e.g., octadecyl group silica gel). The automated apparatus may comprises a unit with a conditioning solution for the purification unit (e.g., a conditioning solution for a solid-phase extraction material). The automated apparatus may comprise a unit with an elution solution for removing biomolecules from the purification unit.

In some embodiments, components are removed from a partition, except for the plurality of sensor elements and a population of analytes interacting with the plurality of sensor elements (i.e., a wash step). In some instances, the automated apparatus may perform a series of wash steps. A wash step may remove biomolecules that are not bound to the sensor elements within the partition. A wash step may desorb a subset of biomolecules bound to sensor elements within a partition. For example, a wash step may result in the desorption and removal of a subset of soft corona analytes, while leaving the majority of hard corona analytes bound to the sensor element.

In some aspects, the present disclosure provides an automated apparatus to identify proteins in a biological sample, the automated apparatus comprising: a sample preparation unit; a substrate comprising a plurality of channels; a plurality of pipettes; a plurality of solutions, a plurality of particles, and wherein the automated apparatus is configured to form a protein corona and digest the protein corona.

In some aspects, the present disclosure provides an automated apparatus to identify proteins in a biological sample, the automated apparatus comprising: a sample preparation unit; a substrate comprising a plurality of channels; a plurality of pipettes; a plurality of solutions, a plurality of nanoparticles, wherein the automated apparatus is configured to form a protein corona and digest the protein corona, and wherein at least one of the solutions is TE 150 mM KCl 0.05% CHAPS buffer.

In some embodiments, the sample preparation unit is configured to add the plurality of nanoparticles to the substrate with the plurality of pipettes. In some embodiments, wherein the sample preparation unit is configured to add the biological sample to the substrate with the plurality of pipettes. In some embodiments, the sample preparation unit is configured to incubate the plurality of nanoparticles and the biological sample to form the protein corona.

In some embodiments, the sample preparation unit is configured to separate the protein corona from the supernatant to form a protein corona pellet. In some embodiments, the sample preparation unit is configured to reconstitute the protein corona pellet with TE 150 mM KCl 0.05% CHAPS buffer.

In some embodiments, the automated apparatus further comprises a magnetic source. In some embodiments, the automated apparatus is configured for BCA, gel, or trypsin digestion of the protein corona.

In some embodiments, the automated apparatus is enclosed. In some embodiments, the automated apparatus is sterilized before use. In some embodiments, the automated apparatus is configured to a mass spectrometry. In some embodiments, the automated apparatus is temperature controlled.

Assaying Methods

In some aspects, the present disclosure provides a method of identify proteins in a biological sample. In some cases the method comprises: adding the biological sample to the automated apparatus disclosed herein; generating proteomic data from the automated apparatus; and quantifying the proteomic data.

In some embodiments, the method comprises incubating a plurality of biomolecules with the biological sample in the automated apparatus to form a biomolecule corona. In some embodiments, incubating the biological sample with the plurality of sensor elements (e.g., particles) contained within the partition of the substrate comprises an incubation time of at least about 10 seconds, at least about 15 seconds, at least about 20 seconds, at least about 25 seconds, at least about 30 seconds, at least about 40 seconds, at least about 50 seconds, at least about 60 seconds, at least about 90 seconds, at least about 2 minutes, at least about 3 minutes, at least about 4 minutes, at least about 5 minutes, at least about 6 minutes, at least about 7 minutes, at least about 8 minutes, at least about 9 minutes, at least about 10 minutes, at least about 15 minutes, at least about 20 minutes, at least about 25 minutes, at least about 30 minutes, at least about 45 minutes, at least about 50 minutes, at least about 60 minutes, at least about 90 minutes, at least about 2 hours, at least about 3 hours, at least about 4 hours, at least about 5 hours, at least about 6 hours, at least about 7 hours, at least about 8 hours, at least about 9 hours, at least about 10 hours, at least about 12 hours, at least about 14 hours, at least about 15 hours, at least about 16 hours, at least about 17 hours, at least about 18 hours, at least about 19 hours, at least about 20 hours, or at least about 24 hours. In some cases, two wells will have two different incubation times. In some embodiments, incubating the biological sample with the plurality of particles contained within the partition of the substrate comprises an incubation temperature between about 4° C. to about 37° C. In some embodiments, incubating the biological sample with the plurality of particles contained within the partition of the substrate comprises an incubation temperature between about 4° C. to about 100° C.

The method, systems, and apparatus of the present disclosure may comprise covering or sealing a partition on the substrate. This may comprise covering a surface of the apparatus with a lid or a seal. The lid or seal may prevent solutions or species from leaving a partition (e.g., evaporating from a partition). The automated apparatus may be configured to place and/or remove the lid or seal. The lid or seal may be pierceable (e.g., may comprise a septum), thereby allowing a syringe or needle to enter a substrate partition without removal of the lid or seal.

In some cases, the system, apparatus and method of the present disclosure further comprise preparing analytes from the biomolecule corona for analysis (e.g., mass spectrometric analysis). This can comprise separating the biomolecule corona from the supernatant in the automated apparatus. The biomolecule corona may be separated from the supernatant by removing the supernatant and then desorbing a plurality of proteins from the biomolecule corona into a desorbate solution (e.g., a resuspension solution). In some cases, a first portion of biomolecules from a biomolecule corona are desorbed from the biomolecule corona and discarded, and a second portion of biomolecules from a biomolecule corona are desorbed from the biomolecule corona and collected (e.g., for analysis). Multiple portions of biomolecules from a biomolecule corona may be separately, desorbed, collected, and analyzed.

In some cases, biomolecules within a biomolecule corona are denatured, fragmented, chemically modified, or any combination thereof. These treatments may be performed on desorbed biomolecules or on biomolecule coronas. The plurality of biomolecules desorbed from a biomolecule corona may comprise 1%, 2%, 3%, 4%, 5%, 6%, 8%, 10%, 12%, 15%, 20%, 25%, 30%, 40%, 50%, 60%, 70%, 80%, 90%, 95%, 98%, 99%, or greater than 99% of the biomolecules from the biomolecule corona. The desorption may performed for different lengths of time, including 5 seconds, 15 seconds, 30 seconds, 1 minute, 2 minutes, 3 minutes, 4 minutes, 5 minutes, 6 minutes, 8 minutes, 10 minutes, 12 minutes, 15 minutes, 20 minutes, 30 minutes, 40 minutes, 50 minutes, 1 hour, 1.5 hours, 2 hours, 3 hours, 4 hours, 5 hours, 6 hours, 8 hours, 12 hours, or longer. In some cases, the desorption comprises physical agitation, such as shaking or sonication. The percent of proteins desorbed from a particle corona may depend on the desorption time, the chemical composition of the desorbate solution into which proteins are desorbed (e.g., pH or buffer-type), the desorption temperature, the form and intensity of physical agitation applied, or any combination thereof. Additionally, the types of proteins desorbed from a protein corona can be responsive to desorption conditions and methods. The types of proteins desorbed from a protein corona may differ by 1%, 2%, 3%, 4%, 5%, 6%, 8%, 10%, 12%, 15%, 20%, 25%, 30%, 40%, 50%, 60%, or more between two desorption conditions or methods.

In some cases, preparing analytes from a biomolecule corona for analysis comprises digesting the biomolecule corona, a subset of biomolecules within the protein corona, or biomolecules desorbed from the biomolecule corona to form a digested sample in the automated apparatus. Preparing analytes from the biomolecule corona for analysis may also comprise chemically modifying a biomolecule from the biomolecule corona, such as methylating or reducing the biomolecule.

Desorbed biomolecules may be collected for further analysis (e.g., mass spectrometric analysis). The automated apparatus may perform the collecting, for example by collecting a volume of sample from a substrate partition comprising biomolecules desorbed from biomolecule coronas. A method may involve placing partition or plurality of partitions (e.g., a well plate) may be placed directly within an instrument for performing said analysis.

A method may comprise multiple rounds of preparing analytes from a biomolecule corona for analysis. A method may comprise 1, 2, 3, 4, 5, 6, 7, 8, 9, 10, or more rounds of preparation. In some cases, each round produces a separate sample for analysis (e.g., desorbed biomolecules may be collected after each round and subjected to mass spectrometric analysis). Two rounds may comprise desorbing different pluralities of proteins from a biomolecule corona. Two rounds may also comprise different desorption methods or conditions, such as different desorbate solution volumes, different desorbate solution types (e.g., desorbate solutions comprising different buffers or osmolarities), different temperatures, or different types and degrees of physical agitation. Two or more successive rounds of preparation from a single biomolecule corona (e.g., desorption and collection of a first subset of biomolecules from a biomolecule corona followed by desorption and collection of a second subset of biomolecules from a biomolecule corona) may generate two sets of biomolecules. This may inform detection or analysis of biomolecule interactions within a protein corona. As such, multiple rounds of preparation from a single biomolecule corona may be used to generate a number biomolecule subsets which exceed the number of partitions or types of sensor. For example, a method utilizing a substrate with 96 partitions (e.g., a 96 well plate) may generate as many as 960 unique biomolecule subsets if each partition comprises a unique combination of particles and solution conditions, and 10 rounds of analyte preparation are performed on each partition.

A different number of rounds of analyte preparation may be performed in separate partitions. Partitions may also be subjected to different analyte preparation conditions. Performing more rounds of analyte preparation can increase the number of proteins or types of proteins collected for analysis (e.g., generate more proteins that fall within concentration ranges accessible for simultaneous mass spectrometric detection). The number proteins or types of proteins detected when multiple rounds of analyte preparation are performed may be 10%, 20%, 30%, 40%, 50%, 60%, 70%, 80%, 90%, 100%, 150%, 200%, or more than 200% higher than if a single round of analyte preparation was performed.

In some cases, the method comprises immobilizing a sensor element within a partition. The immobilization may prevent the sensor element from being removed from the partition when a volume is removed from the partition (e.g., the loading unit removes 95% of the solution from the partition). Immobilization may be performed, for example, chemically (e.g., covalent or non-covalent binding to a substrate). Chemical immobilization may comprise reacting a sensor element with a surface of the partition. Chemical immobilization may also comprise non-covalently associating a sensor element with a surface of the partition. For example, a sensor element may comprise biotin moieties that bind to streptavidin bound to a surface of a partition. Immobilization may be achieved by applying a magnetic field to hold a magnetic sensor element within a partition. For example, a plurality of sensor elements may comprise a plurality of magnetic particles, and the substrate and the magnet may be in proximity such that the one or more magnetic particles are immobilized within a partition in the substrate. Immobilization may be achieved by providing a substrate with a sensor element formed or embedded within a partition on the substrate. For example, a sensor element may be a half-particle formed on the surface of a partition within the substrate.

In some cases, sensor element immobilization allows a biomolecule corona to be separated from the sensor element. This may comprise desorbing a plurality of biomolecules from a biomolecule corona associated with a sensor element, immobilizing the sensor element within the partition, and then collecting the solution with the plurality of biomolecules from the biomolecule corona, thereby separating at least a portion of a biomolecule corona from a sensor element.

Figure 4:
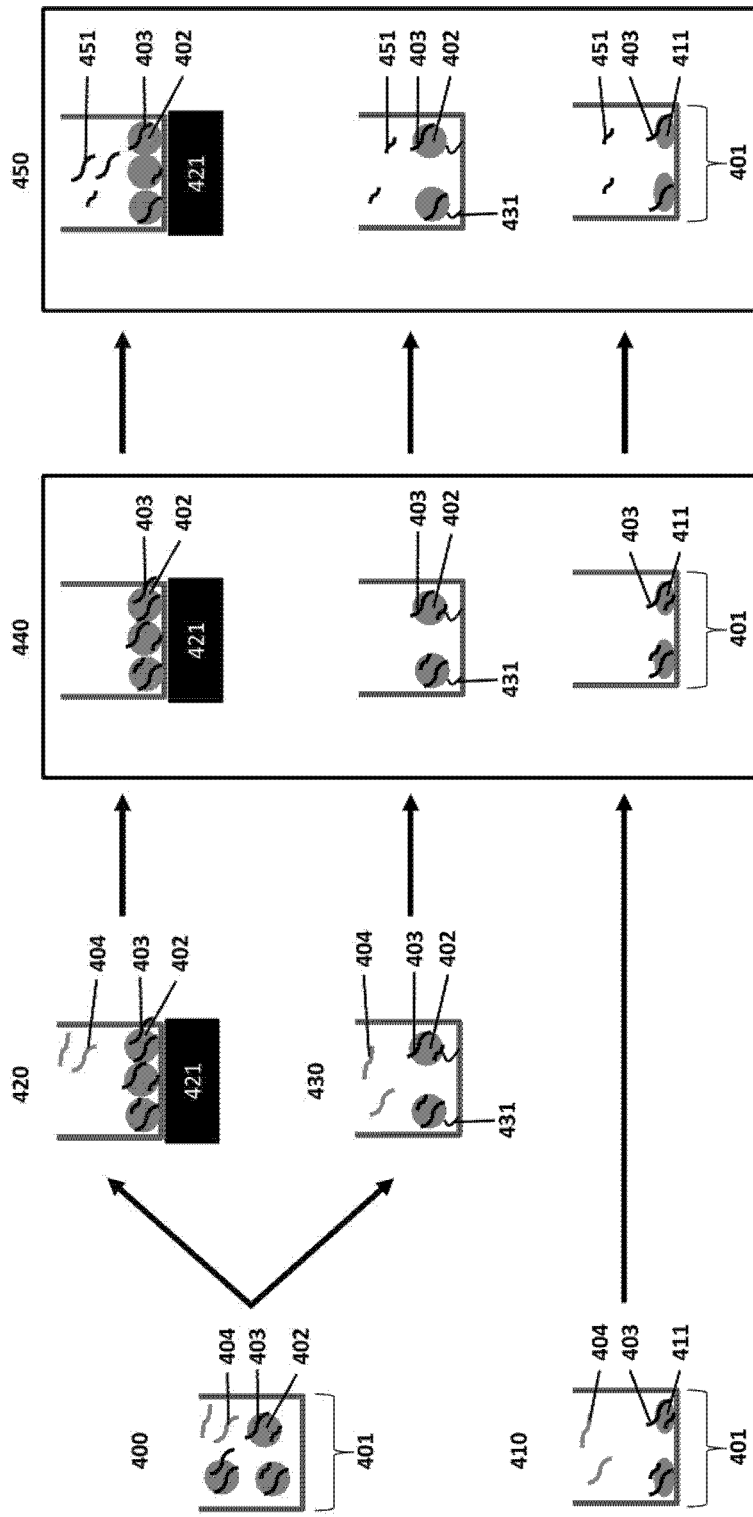
FIG. 4 shows an example illustration of sensor array analyte capture methods.

FIG. 4 illustrates examples of methods comprising immobilization sensor elements, which can be performed by the automated apparatus of the present disclosure. These methods utilize particles 402 and 411 to capture a subset of biomolecules 403 and 404 in a sample.

Panel 400 shows a partition 401 containing particles 402 and biomolecules. The particles are suspended within the partition, and have adsorbed biomolecules 403 from the sample, thereby forming biomolecule coronas. A number of biomolecules 404 may not adsorb to the particles, and will instead be suspended within the partition. Panel 410 shows an alternative method, comprising particles 411 that are formed on the surface of the partition.

Panels 420 and 430 show two methods for immobilizing the particles. In panel 420, the particles are collected onto the bottom of the partition by a magnet 421. In panel 430, the particles are crosslinked to the partition via linkers 431. Both methods result in the particles becoming immobilized to the partition. Throughout the immobilization process, particle-adsorbed biomolecules 403 remain adsorbed to the particles, while the unbound biomolecules 404 remain unbound from the particles.

Panel 440 shows the results of wash steps on the partitions from panels 410, 420, and 430. In all three cases, the wash removes unbound biomolecules from the partition, while leaving the immobilized particles and the biomolecules adsorbed to them. Panel 450 then shows desorption of the biomolecule coronas, wherein a first plurality of biomolecules 451 elute from the particles, and a second plurality of biomolecules 403 remain adsorbed to the particles. The ratio of eluted to adsorbed biomolecules and the types of biomolecules eluted from the particles depends on the elution conditions (e.g., temperature, degree and type of physical agitation, solution conditions such as pH). The eluted biomolecules can be collected (e.g., by the loading unit) for further processing (e.g., fragmentation) or direct analysis.

Figure 5:
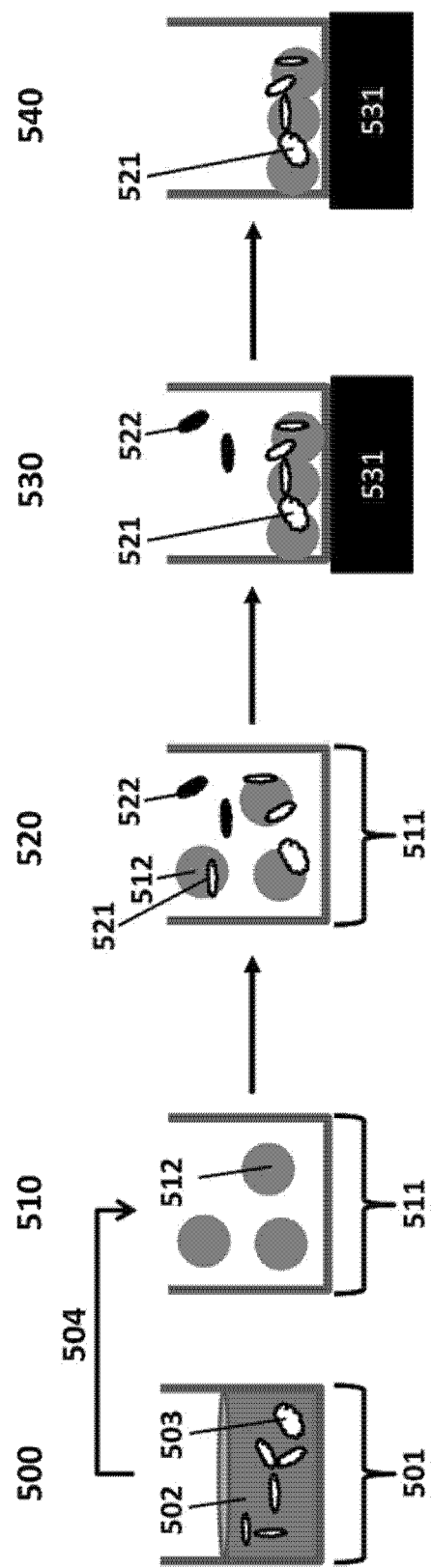
FIG. 5 shows a step-wise illustration of automated sample processing for magnetic sensor array particles.

FIG. 5 shows an example of a sample preparation method that can be performed by the automated apparatus of the present disclosure. This method utilizes sensor elements 512 to generate a subset of biomolecules from a biological sample 502. The biological sample (shown in panel 500), which is stored in a sample container 501, comprises a number of biomolecules. A volume of the sample can optionally be processed 504 (e.g., cells within the sample can be lysed, nucleic acids and proteins can be fragmented, the sample can be filtered to remove large biomolecules, etc.), and then added to a partition 511 comprising sensor elements 512. As is depicted in panel 520 a portion of the biomolecules 521 can bind to the sensor elements, separating them from a portion of biomolecules 522 that does not bind to the sensor elements. As is shown in panel 530, the sensor elements can then be immobilized within the partition by bringing the partition in contact with a magnet 531. The partition can then undergo a wash cycle (e.g., addition of buffer to the partition followed by removal of sample from the partition), resulting in the removal of the portion of biomolecules 522 that did not bind to the sensor elements (shown in panel 540). The bound biomolecules 521 can be eluted from the sensor elements and collected for further processing or analysis.

Figure 6:
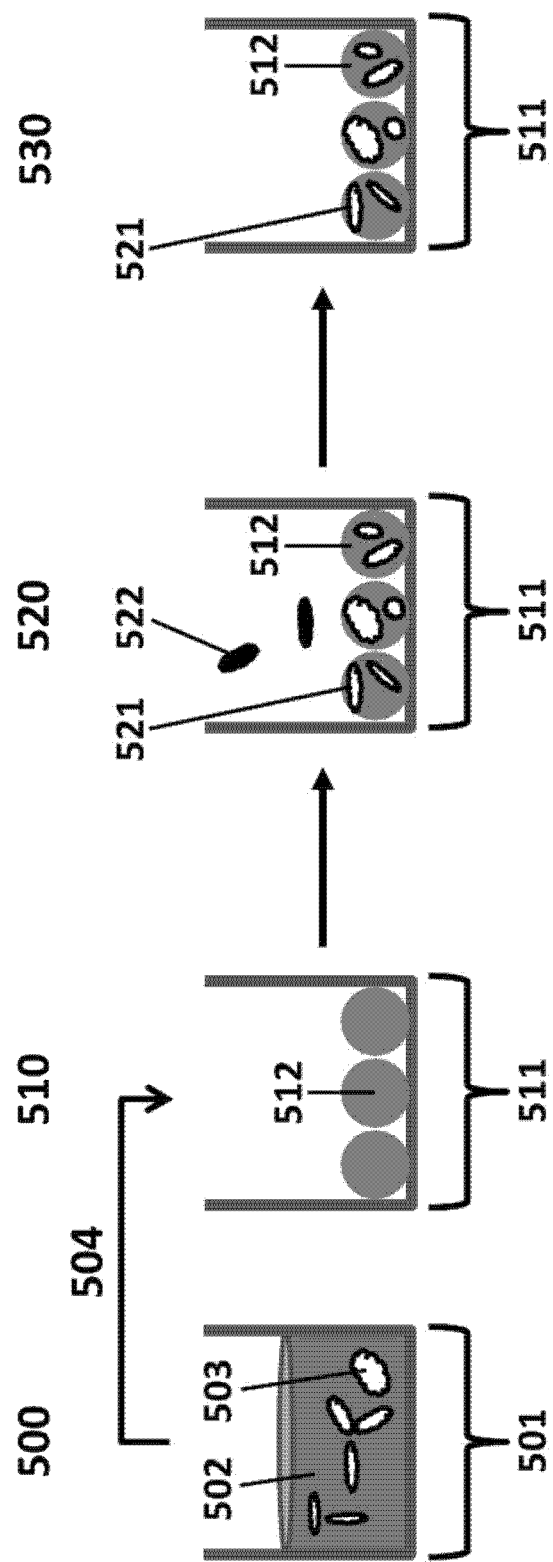
FIG. 6 shows a step-wise illustration of automated sample processing for immobilized sensor array particles.

FIG. 6 illustrates a sample preparation method that can be performed by the automated apparatus of the present disclosure. This method utilizes sensor elements 512 that are formed on the surface of a substrate partition 511 to collect biomolecules 503 from a sample 502. The biological sample is transferred 504 from a sample holding unit 501 to the substrate partition 511. As is shown in panel 520, the sensor elements will adsorb a first portion of the biomolecules from the sample 521, while a second portion 522 will remain unbound. Panel 530 depicts the removal of the unbound biomolecules, which leaves the sensor elements 512 and sensor element-bound biomolecules 521 within the partition. These biomolecules can subsequently be desorbed from the sensor elements and collected (e.g., by the loading unit) for further processing or analysis.

The methods disclosed herein may comprise filtering a sensor element from a solution. For example, the method may comprise desorbing a plurality of biomolecules from a biomolecule corona associated with a sensor element, and filtering the solution such that the sensor element is collected on the filter and the plurality of biomolecules remain in solution. The filtering may be performed after denaturation (e.g., digestion). The filtering may also remove a plurality of biomolecules or biological species such as intact proteins (e.g., undigested proteins from the biological sample or proteases).

In some cases, the method comprises a purification step. The purification step can precede or follow preparation of analytes from a biomolecule corona. A purification step may comprise transferring a biological sample (e.g., biomolecules eluted and collected from a biomolecule corona) to a purification unit (e.g., a chromatography column) or partition within a purification unit. Purification may involve transferring a plurality of sample partitions from the substrate into separate partitions in the purification unit. The purification unit may comprise a solid-phase extraction plate. The purification step may remove reagents (e.g., chemicals and enzymes) from the denaturation solution. Following purification, the biological sample may be recollected for further enrichment or chemical treatment within the substrate or purification unit, or may be collected for direct analysis (e.g., mass spectrometric analysis).

Collectively, the methods of the present disclosure enable a high degree of profiling depth for biological samples. The subset of biomolecules collected in the methods of the present disclosure may enable, without further manipulation or modification of said subset of biomolecules, mass spectrometric detection of at least 2%, at least 3%, at least 4%, at least 5%, at least 6%, at least 7%, at least 8%, at least 9%, at least 10%, at least 12%, at least 15%, at least 20%, at least 25%, at least 30%, at least 40%, at least 50%, at least 60%, or more than 60% of the types of biomolecules in the biological sample from which the subset of biomolecules were collected. The subset of biomolecules may enable, without further manipulation or modification of said subset of biomolecules, mass spectrometric detection of at least 2%, at least 3%, at least 4%, at least 5%, at least 6%, at least 7%, at least 8%, at least 9%, at least 10%, at least 12%, at least 15%, at least 20%, at least 25%, at least 30%, at least 40%, at least 50%, or more than 50% of the types of proteins in a sample. The subset of biomolecules collected on a sensor element or prepared for analysis may enable, without further manipulation or modification of said subset of biomolecules, simultaneous mass spectrometric detection of two biomolecules (e.g., proteins) spanning 6, 7, 8, 9, 10, 11, 12 or more orders of magnitude in a sample. For example, the two biomolecules may be desorbed and collected at concentrations within 6 orders of magnitude within a single sample, fragmented, and then submitted for mass spectrometric analysis.

In some cases, a type of sensor element (e.g., all sensor elements of a given type that are within contact of a single sample) adsorbs at least 100 to at least 300 types of proteins upon contacting a biological sample. A type of sensor element may adsorb at least 200 to at least 500 types of proteins upon contacting a biological sample. A type of sensor element may adsorb at least 300 to at least 800 types of proteins upon contacting a biological sample. A type of sensor element may adsorb at least 400 to at least 1000 types of proteins upon contacting a biological sample. A type of sensor element may adsorb at least 500 to at least 1200 types of proteins upon contacting a biological sample.

In some cases, the proteins collected from a plurality of sensor elements will be identified on the level of protein groups. The plurality of protein groups collected on sensor elements in a partition may comprise from 1 to 20,000 protein groups. The plurality of protein groups collected on sensor elements in a partition may comprise from 100 to 10,000 protein groups. The plurality of protein groups collected on sensor elements in a partition may comprise from 100 to 5,000 protein groups. The plurality of protein groups collected on sensor elements in a partition may comprise from 300 to 2,200 protein groups. The plurality of protein groups collected on sensor elements in a partition may comprise from 1,200 to 2,200 protein groups. The plurality of protein groups collected on sensor elements in a partition may comprise from 20,000 to 25,000 protein groups. The plurality of protein groups collected on sensor elements in a partition may comprise from 25,000 to 30,000 protein groups. The plurality of protein groups collected on sensor elements in a partition may comprise from 30,000 to 50,000 protein groups.

The methods of the present disclosure can result in the enrichment of low abundance biomolecules (e.g., proteins) from a biological sample. A low abundance biomolecule may be a biomolecule at a concentration of 10 ng/mL or less in a biological sample.

The methods of the present disclosure can result in the enrichment of biomolecules (e.g., proteins) present at a concentration that is at least 6 orders of magnitude lower than the concentration of the most abundant biomolecule of the same type in the same sample (e.g., a low abundance protein may be a protein whose concentration is at least 6 orders of magnitude lower than the most abundant protein in the sample). Databases, such as the Carr database (Keshishian et al., Mol. Cell Proteomics 14, 2375-2393 (2015), Plasma Proteome Database (plasmaproteomedatabase.org)) characterizing the plasma proteome, may provide a basis of comparison such that one can ascertain whether a protein or biomolecule detected is enriched relative to other biomolecule(s) present in a plasma sample. Similar databases may be used for other types of biological samples.

In particular cases, the biological sample comprises blood, plasma, or serum, and a biomolecule corona comprises a lower proportion of albumin to non-albumin proteins than the biological sample. The ratio of albumin to non-albumin proteins may be 20%, 30%, 40%, 50%, 60%, or 70% lower in a biomolecule corona than in the sample from which proteins were adsorbed.

The concentration range of a plurality of biomolecules may be compressed upon formation of a biomolecule corona. For example, the automated apparatus may increase the number of types of biomolecules whose concentrations are within 6 orders of magnitude of the most concentrated biomolecule in the sample by at least 25%, 50%, 100%, 200%, 300%, 500%, or 1000%. Analogously, the compressed dynamic range may comprise an increase in the number of types of proteins whose concentrations are within 6 orders of magnitude of the most abundant biomolecule in the sample. The automated apparatus may increase the number of types of proteins whose concentrations are within 6 orders of magnitude of the most concentrated protein in the sample by at least 25%, 50%, 100%, 200%, 300%, 500%, or 1000%. The automated apparatus may enrich a subset of biomolecules from a biological sample, and the subset of biomolecules may comprise at least 10% of the types of biomolecules from the biological sample within a 6 order of magnitude concentration range. The automated apparatus may enrich a subset of biomolecules from a biological sample, and the subset of biomolecules may comprise at least 20% of the types of biomolecules from the biological sample within a 6 order of magnitude concentration range. The automated apparatus may enrich a subset of biomolecules from a biological sample, and the subset of biomolecules may comprise at least 30% of the types of biomolecules from the biological sample within a 6 order of magnitude concentration range. The automated apparatus may enrich a subset of biomolecules from a biological sample, and the subset of biomolecules may comprise at least 40% of the types of biomolecules from the biological sample within a 6 order of magnitude concentration range. The automated apparatus may enrich a subset of biomolecules from a biological sample, and the subset of biomolecules may comprise at least 50% of the types of biomolecules from the biological sample within a 6 order of magnitude concentration range. The automated apparatus may enrich a subset of biomolecules from a biological sample, and the subset of biomolecules may comprise at least 60% of the types of biomolecules from the biological sample within a 6 order of magnitude concentration range. The automated apparatus may enrich a subset of biomolecules from a biological sample, and the subset of biomolecules may comprise at least 70% of the types of biomolecules from the biological sample within a 6 order of magnitude concentration range. The automated apparatus may enrich a subset of biomolecules from a biological sample, and the subset of biomolecules may comprise at least 10% of the types of proteins from the biological sample within a 6 order of magnitude concentration range. The automated apparatus may enrich a subset of biomolecules from a biological sample, and the subset of biomolecules may comprise at least 20% of the types of proteins from the biological sample within a 6 order of magnitude concentration range. The automated apparatus may enrich a subset of biomolecules from a biological sample, and the subset of biomolecules may comprise at least 30% of the types of proteins from the biological sample within a 6 order of magnitude concentration range. The automated apparatus may enrich a subset of biomolecules from a biological sample, and the subset of biomolecules may comprise at least 40% of the types of proteins from the biological sample within a 6 order of magnitude concentration range. The automated apparatus may enrich a subset of biomolecules from a biological sample, and the subset of biomolecules may comprise at least 50% of the types of proteins from the biological sample within a 6 order of magnitude concentration range. The automated apparatus may enrich a subset of biomolecules from a biological sample, and the subset of biomolecules may comprise at least 60% of the types of proteins from the biological sample within a 6 order of magnitude concentration range. The automated apparatus may enrich a subset of biomolecules from a biological sample, and the subset of biomolecules may comprise at least 70% of the types of proteins from the biological sample within a 6 order of magnitude concentration range.

The methods and sensor elements of the present disclosure may be tailored so that biomolecule corona composition is invariant with respect to sample lipid concentration. Changes of at most 10% in the lipid concentration in a biological sample may result in changes of less than 5%, 2%, 1%, or 0.1% in the composition of the proteins in a biomolecule corona. Changes of at most 10% in the lipid concentration in a biological sample may result in changes of less than 5%, 2%, 1%, or 0.1% in the number of types of proteins in a biomolecule corona. Changes of at most 10% in the lipid concentration in a biological sample may result in changes of less than 5%, 2%, 1%, or 0.1% in the total number of proteins in a biomolecule corona.

In some embodiments, the method further comprises washing the digested sample in the automated apparatus. In some embodiments, quantifying the proteomic data comprises providing the proteomic data to a mass spectrometer. In some embodiments, the biological sample is a biofluid. In some embodiments, the biofluid is serum or plasma.

In some cases, the entire assay time from a single sample, such as a pooled plasma sample, including sample preparation and LC-MS, can be about 8 hours. The entire assay time from a single sample, such as a pooled plasma sample, including sample preparation and LC-MS, can be about at least 1 hour, at least 2 hours, at least 3 hours, at least 4 hours, at least 5 hours, at least 6 hours, at least 7 hours, at least 8 hours, at least 9 hours, at least 10 hours, under 20 hours, under 19 hours, under 18 hours, under 17 hours, under 16 hours, under 15 hours, under 14 hours, under 13 hours, under 12 hours, under 11 hours, under 10 hours, under 9 hours, under 8 hours, under 7 hours, under 6 hours, under 5 hours, under 4 hours, under 3 hours, under 2 hours, under 1 hour, at least 5 min to 10 min, at least 10 min to 20 min, at least 20 min to 30 min, at least 30 min to 40 min, at least 40 min to 50 min, at least 50 min to 60 min, at least 1 hour to 1.5 hours, at least 1.5 hour to 2 hours, at least 2 hour to 2.5 hours, at least 2.5 hour to 3 hours, at least 3 hour to 3.5 hours, at least 3.5 hour to 4 hours, at least 4 hour to 4.5 hours, at least 4.5 hour to 5 hours, at least 5 hour to 5.5 hours, at least 5.5 hour to 6 hours, at least 6 hour to 6.5 hours, at least 6.5 hour to 7 hours, at least 7 hour to 7.5 hours, at least 7.5 hour to 8 hours, at least 8 hour to 8.5 hours, at least 8.5 hour to 9 hours, at least 9 hour to 9.5 hours, or at least 9.5 hour to 10 hours.

Dynamic Range

The biomolecule corona analysis methods described herein may comprise assaying biomolecules in a sample of the present disclosure across a wide dynamic range. The dynamic range of biomolecules assayed in a sample may be a range of measured signals of biomolecule abundances as measured by an assay method (e.g., mass spectrometry, chromatography, gel electrophoresis, spectroscopy, or immunoassays) for the biomolecules contained within a sample. For example, an assay capable of detecting proteins across a wide dynamic range may be capable of detecting proteins of very low abundance to proteins of very high abundance. The dynamic range of an assay may be directly related to the slope of assay signal intensity as a function of biomolecule abundance. For example, an assay with a low dynamic range may have a low (but positive) slope of the assay signal intensity as a function of biomolecule abundance, e.g., the ratio of the signal detected for a high abundance biomolecule to the ratio of the signal detected for a low abundance biomolecule may be lower for an assay with a low dynamic range than an assay with a high dynamic range. In specific cases, dynamic range may refer to the dynamic range of proteins within a sample or assaying method.

The biomolecule corona analysis methods described herein may compress the dynamic range of an assay. The dynamic range of an assay may be compressed relative to another assay if the slope of the assay signal intensity as a function of biomolecule abundance is lower than that of the other assay. For example, a plasma sample assayed using protein corona analysis with mass spectrometry may have a compressed dynamic range compared to a plasma sample assayed using mass spectrometry alone, directly on the sample or compared to provided abundance values for plasma proteins in databases (e.g., the database provided in Keshishian et al., Mol. Cell Proteomics 14, 2375-2393

Figure 13:
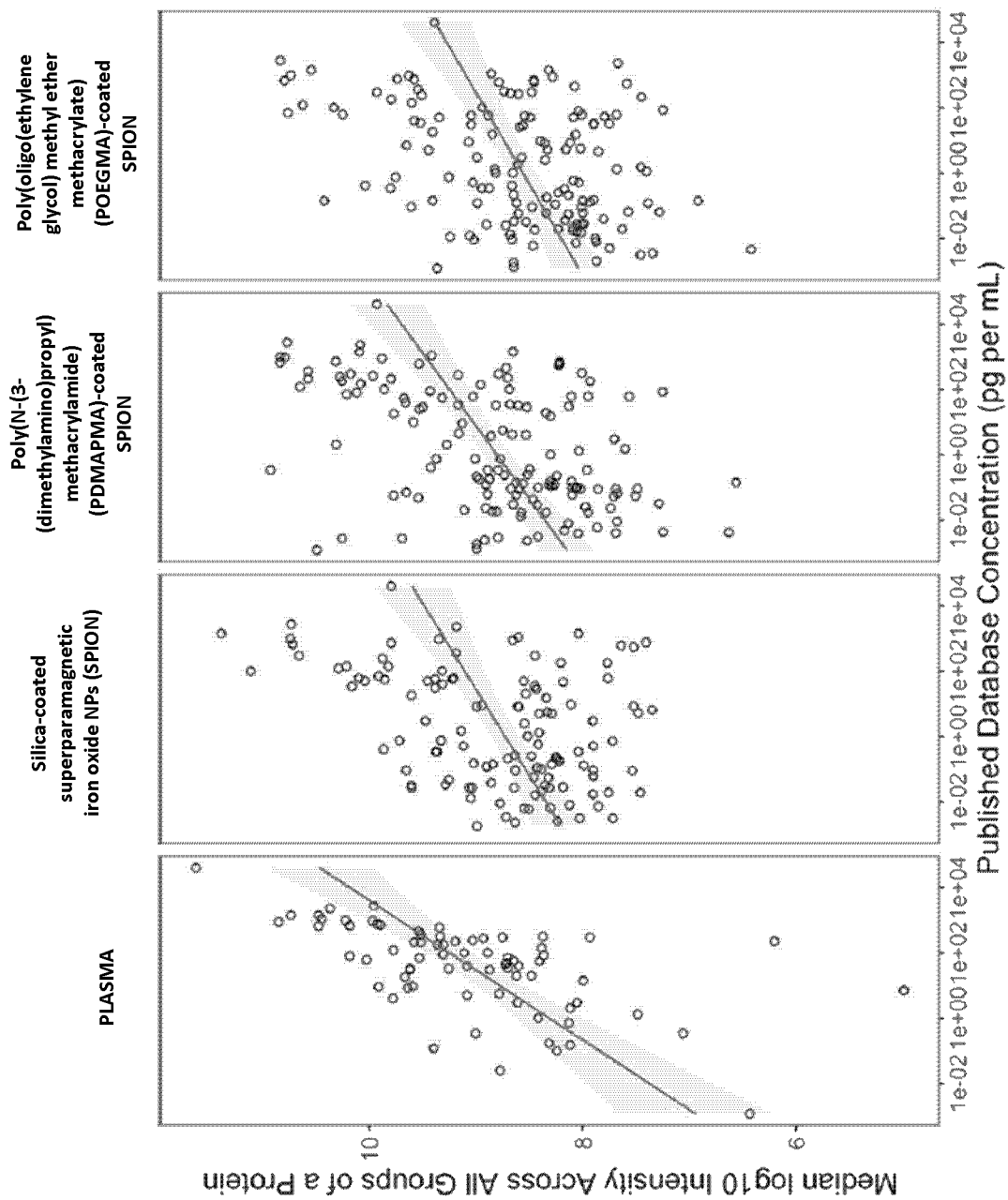
FIG. 13 shows correlation of the maximum intensities of particle corona proteins and plasma proteins to the published concentration of the same proteins. The blue plotted lines are linear regression models to the data and the shaded regions represent the standard error of the model fit. The dynamic range of the samples assayed with particles ("S-003," "S-007," and "S-011", detailed in TABLE 1) exhibited a compressed dynamic range as compared to the plasma sample not assayed with particles ("Plasma"), as shown by the decrease in slopes of the linear fits. The slopes of each plot are 0.47, 0.19, 0.22, and 0.18 for, plasma without particles, plasma with S-003 particles, plasma with S-007 particles, and plasma with S-011 particles, respectively.
Figure 14:
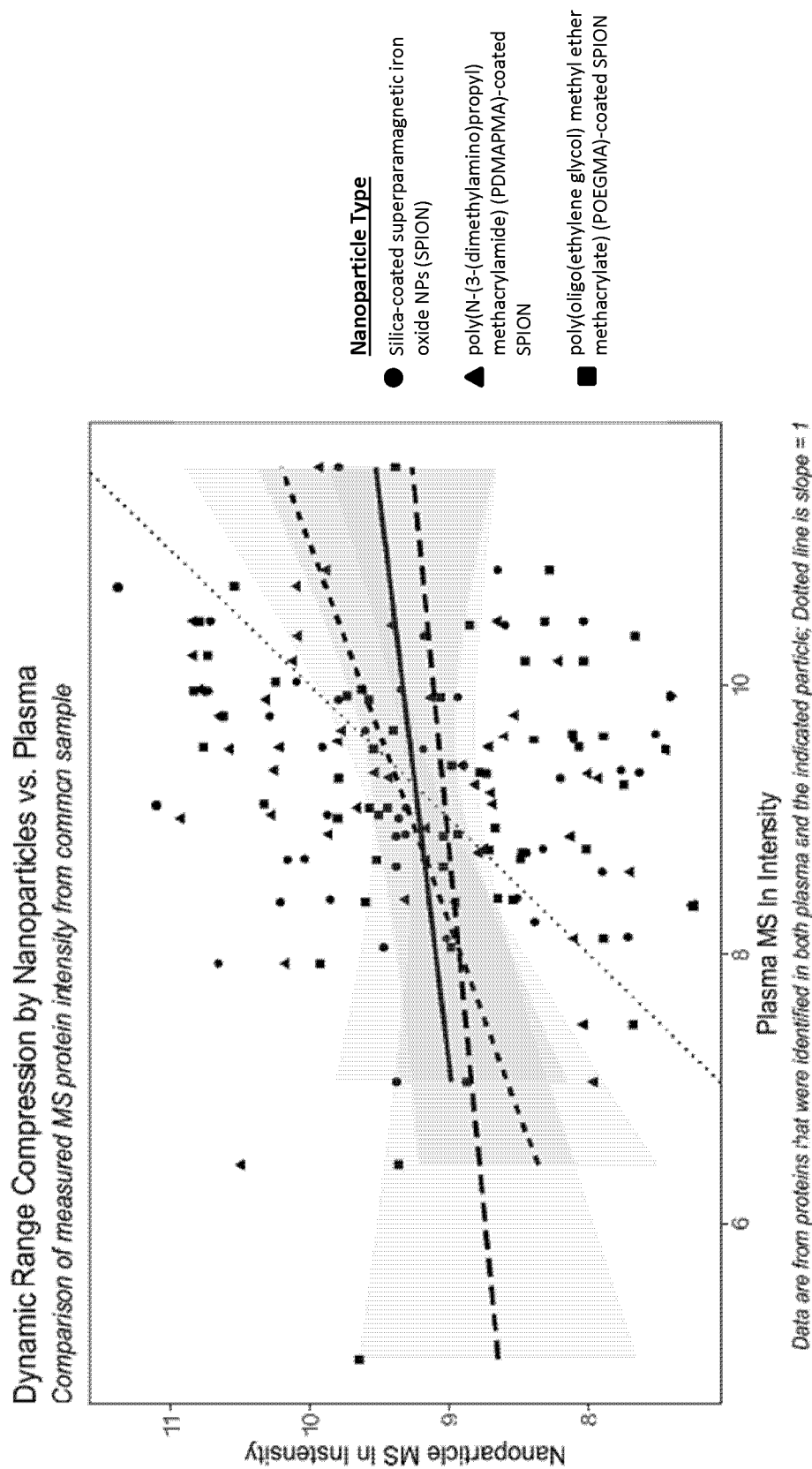
FIG. 14 shows the dynamic range compression of a protein corona analysis assay with mass spectrometry as compared to mass spectrometry without particle corona formation. Protein intensities of common proteins identified in particle corona in the plasma samples assayed in FIG. 13 ("Nanoparticle MS In Intensity") are plotted against the protein intensity identified by mass spectrometry of plasma without particles ("Plasma MS In Intensity"). The lightest dotted line shows a slope of 1, indicating the dynamic range of mass spectrometry without particles. The slopes of the linear fits to the protein intensity was 0.12, 0.36, and 0.093 for S-003, S-007, and S-011 particles, respectively. The grayed area indicates the standard error region of the regression fit.

(2015), also referred to herein as the "Carr database"), as shown in FIG. 13 and FIG. 14. The compressed dynamic range may enable the detection of more low abundance biomolecules in a biological sample using biomolecule corona analysis with mass spectrometry than using mass spectrometry alone.

In some embodiments, the dynamic range of a proteomic analysis assay may be the ratio of the signal produced by highest abundance proteins (e.g., the highest 10% of proteins by abundance) to the signal produced by the lowest abundance proteins (e.g., the lowest 10% of proteins by abundance). Compressing the dynamic range of a proteomic analysis may comprise decreasing the ratio of the signal produced by the highest abundance proteins to the signal produced by the lowest abundance proteins for a first proteomic analysis assay relative to that of a second proteomic analysis assay. The protein corona analysis assays disclosed herein may compress the dynamic range relative to the dynamic range of a total protein analysis method (e.g., mass spectrometry, gel electrophoresis, or liquid chromatography).

Provided herein are several methods for compressing the dynamic range of a biomolecular analysis assay to facilitate the detection of low abundance biomolecules relative to high abundance biomolecules. For example, a particle type of the present disclosure can be used to serially interrogate a sample. Upon incubation of the particle type in the sample, a biomolecule corona comprising forms on the surface of the particle type. If biomolecules are directly detected in the sample without the use of said particle types, for example by direct mass spectrometric analysis of the sample, the dynamic range may span a wider range of concentrations, or more orders of magnitude, than if the biomolecules are directed on the surface of the particle type. Thus, using the particle types disclosed herein may be used to compress the dynamic range of biomolecules in a sample. Without being limited by theory, this effect may be observed due to more capture of higher affinity, lower abundance biomolecules in the biomolecule corona of the particle type and less capture of lower affinity, higher abundance biomolecules in the biomolecule corona of the particle type.

A dynamic range of a proteomic analysis assay may be the slope of a plot of a protein signal measured by the proteomic analysis assay as a function of total abundance of the protein in the sample. Compressing the dynamic range may comprise decreasing the slope of the plot of a protein signal measured by a proteomic analysis assay as a function of total abundance of the protein in the sample relative to the slope of the plot of a protein signal measured by a second proteomic analysis assay as a function of total abundance of the protein in the sample. The protein corona analysis assays disclosed herein may compress the dynamic range relative to the dynamic range of a total protein analysis method (e.g., mass spectrometry, gel electrophoresis, or liquid chromatography).

Automated Systems

Various aspects of the present disclosure provide an automated system comprising an automated apparatus configured to isolate a subset of biomolecules from a biological sample, a mass spectrometer configured to receive the subset of biomolecules and to generate data comprising mass spectrometric or tandem mass spectrometric signals, and a computer comprising one or more computer processors and a computer readable medium comprising machine-executable code that, upon execution of the code, generates a biological fingerprint and assigns a biological state based on the biological fingerprint.

In many cases, the automated apparatus comprises a sensor element or plurality of sensor elements which adsorb biomolecules from biological solutions, thereby forming biomolecule coronas. They type, amount, and categories of the biomolecules that make up these biomolecule coronas are strongly related to the physicochemical properties of the sensor elements themselves and the complex interactions between the different biomolecules themselves and the sensor elements. These interactions lead to the production of a unique biomolecule corona signature for each sensor element. In other words, depending on which biomolecules interact with the sensor element not only influences the makeup of the biomolecule corona but also can alter which other different biomolecules can also interact with that specific sensor element.

Different sensor elements each with their own biomolecule corona signature can be contacted with a sample to produce a unique biomolecule fingerprint for that sample. This fingerprint can then be used to determine a disease state of a subject. A plurality of sensor elements may be able to bind a plurality of biomolecules in a sample to produce a biomolecule corona signature. A plurality of sensor elements may have distinct biomolecule corona signatures. In particular cases, each type of sensor element has a distinct biomolecule corona signature. For example, a plurality of particles comprising 5 µM of each of 5 types of particles could have one biomolecule corona signature for each particle type.

The plurality of sensor elements when contacted with a sample produces a plurality of biomolecule corona signatures which together form a biomolecule fingerprint. The "biomolecule fingerprint" is the combined composition or pattern of biomolecules of at least two biomolecule corona signatures for the plurality of sensor elements. The biomolecule fingerprint may comprise at least 5, 10, 20, 40, 80, 150, or 200 distinct biomolecule corona signatures.

In some cases, the automated system is configured so that the biomolecule corona may be assayed separately for each sensor element, allowing the biomolecule corona signature to be determined for each element. More broadly, the automated system may be configured so that each sample partition (e.g., each well in the substrate) can be assayed separately, so that the combined set of biomolecule corona signatures may be determined for each partition.

Analogously, the computer may be configured to compare data from multiple biomolecule corona signatures, partitions, or separate subsets of biomolecules collected from an individual partition (e.g., through multiple rounds of desorption). This can provide a profiling sensitivity that is not possible with conventional methods. Many biological states (such as many pre-disease states) create minute variance in a patient's biological sample (e.g., blood, urine, etc.) that are often not discernible from biomarker analysis alone. The power of the present apparatuses, systems, methods, and sensor elements in part, stems from the interdependence of sensor element characteristics and biological sample composition on biomolecule corona composition, so that a small change in the populations, chemical states (e.g., post-translational modification status), or even conformations of sparsely populated biomolecules can have a major impact on the biomolecule corona signature for a particular sensor element. Furthermore, a biological state which may not be evident from a single set of data may be clearly elucidated by the correlation between disparate biomolecule abundances across multiple biomolecule corona signatures or sample partition measurements. Thus, a combination of nearly identical biomolecule corona signatures can distinguish healthy subjects from cancer-ridden subjects with a high degree of accuracy.

In some cases, the computer is configured to process the data comprising the intensity, APEX, spectral count or number of peptides, Ion mobility behavior of the mass spectrometric or tandem mass spectrometric signal between a plurality of the distinct biomolecule corona signatures. The computer may be configured to process between 5,000 and 5,000,000 signals between a plurality of the distinct biomolecule corona signatures or sample partitions. The computer may be configured to process between 10,000 and 5,000,000 signals between a plurality of the distinct biomolecule corona signatures or sample partitions. The computer may be configured to compare between 20,000 and 200,000 signals between a plurality of the distinct biomolecule corona signatures or sample partitions. The computer may be configured to compare between 400,000 and 1,000,000 signals between a plurality of the distinct biomolecule corona signatures or sample partitions. The computer may be configured to compare between 600,000 and 2,000,000 signals between a plurality of the distinct biomolecule corona signatures or sample partitions. The computer may be configured to compare between 1,000,000 and 5,000,000 signals between a plurality of the distinct biomolecule corona signatures or sample partitions. In some cases, the signals comprise mass spectrometric or tandem mass spectrometric signals.

An aspect of the present disclosure provides methods for generating a biomolecule fingerprint from one or more sets of mass spectrometric data, tandem mass spectrometric data, chromatographic data, ion mobility data, or any combination thereof. In some cases, mass spectrometric data, tandem mass spectrometric data, chromatographic data, or ion mobility data may be used to determine the concentration of a biomolecule from a biological sample. A plurality of sample partitions may be subjected to a separate mass spectrometric or tandem mass spectrometric runs. A plurality of sample partitions may also be pooled and collectively analyzed in a single mass spectrometric or tandem mass spectrometric run. Multiple mass spectrometric runs may be coupled with multiple different chromatographic methods (e.g., different columns, buffers, or gradients). A single mass spectrometric or tandem mass spectrometric run is performed in less than two hours, less than one hour, or less than half an hour.

Aspects of the present disclosure provide methods for identifying biological states and biomolecules with high degrees of certainty and accuracy. The computer may be configured to identify a biomolecule or characterize an unidentified molecular feature based on a mass spectrometric or tandem mass spectrometric signal and or ion mobility and chromatographic behavior with a probability or certainty threshold of at least 95%. The computer may associate a biomolecule fingerprint with a biological state with at least 70% accuracy, at least 75% accuracy, at least 80% accuracy, at least 85% accuracy, at least 90% accuracy, at least 92% accuracy, at least 95% accuracy, at least 96% accuracy, at least 97% accuracy, at least 98% accuracy, at least 99% accuracy, or 100% accuracy. The computer may associate a biomolecule fingerprint with a biological state with at least 70% sensitivity, at least 75% sensitivity, at least 80% sensitivity, at least 85% sensitivity, at least 90% sensitivity, at least 92% sensitivity, at least 95% sensitivity, at least 96% sensitivity, at least 97% sensitivity, at least 98% sensitivity, at least 99% sensitivity, or 100% sensitivity. The computer may be capable of distinguishing between two biological states associated with biological fingerprints that differ by less than 20%, 15%, 10%, or 8%, 5%, 3%, 2%, or 1%. In some aspects, a biomolecule identification is validated if a threshold level of diagnostic signals are detected. For example, if a threshold number of three uniquely assignable peptide fragment signals is provided for protein group identification in a mass spectrometric assay, then two peptide fragment signals corresponding to a particular protein group will not be counted.

Sensor Elements

As used herein, the term "sensor element" refers to elements that are able to bind to a plurality of biomolecules when in contact with a sample and encompasses the term "particle". The sensor element may be an element from about 5 nanometers (nm) to about 50000 nm in at least one direction. Suitable sensor elements include, for example, but not limited to a sensor element from about 5 nm to about 50,000 nm in at least one direction, including, about 5 nm to about 40000 nm, alternatively about 5 nm to about 30000 nm, alternatively about 5 nm to about 20,000 nm, alternatively about 5 nm to about 10,000 nm, alternatively about 5 nm to about 5000 nm, alternatively about 5 nm to about 1000 nm, alternatively about 5 nm to about 500 nm, alternatively about 5 nm to 50 nm, alternatively about 10 nm to 100 nm, alternatively about 20 nm to 200 nm, alternatively about 30 nm to 300 nm, alternatively about 40 nm to 400 nm, alternatively about 50 nm to 500 nm, alternatively about 60 nm to 600 nm, alternatively about 70 nm to 700 nm, alternatively about 80 nm to 800 nm, alternatively about 90 nm to 900 nm, alternatively about 100 nm to 1000 nm, alternatively about 1000 nm to 10000 nm, alternatively about 10000 nm to 50000 nm and any combination or amount in between (e.g. 5 nm, 10 nm, 15 nm, 20 nm, 25 nm, 30 nm, 35 nm, 40 nm, 45 nm, S0 nm, 55 nm, 60 nm, 65 nm, 70 nm, 80 nm, 90 nm, 100 nm, 125 nm, 150 nm, 175 nm, 200 nm, 225 nm, 250 nm, 275 nm, 300 nm, 350 nm, 400 nm, 450 nm, 500 nm, 550 nm, 600 nm, 650 nm, 700 nm, 750 nm, 800 nm, 850 nm, 900 nm, 1000 nm, 1200 nm, 1300 nm, 1400 nm, 1500 nm, 1600 nm, 1700 nm, 1800 nm, 1900 nm, 2000 nm, 2500 nm, 3000 nm, 3500 nm, 4000 nm, 4500 nm, 5000 nm, 5500 nm, 6000 nm, 6500 nm, 7000 nm, 7500 nm, 8000 nm, 8500 nm, 9000 nm, 10000 nm, 11000 nm, 12000 nm, 13000 nm, 14000 nm, 15000 nm, 16000 nm, 17000 nm, 18000 nm, 19000 nm, 20000 nm, 25000 nm, 30000 nm, 35000 nm, 40000 nm, 45000 nm, 50000 nm and any number in between). A nanoscale sensor element refers to a sensor element that is less than 1 micron in at least one direction. Suitable examples of ranges of nanoscale sensor elements include, but are not limited to, for example, elements from about 5 nm to about 1000 nm in one direction, including, from example, about 5 nm to about 500 nm, alternatively about 5 nm to about 400 nm, alternatively about 5 nm to about 300 nm, alternatively about 5 nm to about 200 nm, alternatively about 5 nm to about 100 nm, alternatively about 5 nm to about 50 nm, alternatively about 10 nm to about 1000 nm, alternatively about 10 nm to about 750 nm, alternatively about 10 nm to about 500 nm, alternatively about 10 nm to about 250 nm, alternatively about 10 nm to about 200 nm, alternatively about 10 nm to about 100 nm, alternatively about S0 nm to about 1000 nm, alternatively about 50 nm to about 500 nm, alternatively about 50 nm to about 250 nm, alternatively about 50 nm to about 200 nm, alternatively about 50 nm to about 100 nm, and any combinations, ranges or amount in-between (e.g. 5 nm, 10 nm, 15 nm, 20 nm, 25 nm, 30 nm, 35 nm, 40 nm, 45 nm, S0 nm, 55 nm, 60 nm, 65 nm, 70 nm, 80 nm, 90 nm, 100 nm, 125 nm, 150 nm, 175 nm, 200 nm, 225 nm, 250 nm, 275 nm, 300 nm, 350 nm, 400 nm, 450 nm, 500 nm, 550 nm, 600 nm, 650 nm, 700 nm, 750 nm, 800 nm, 850 nm, 900 nm, 1000 nm, etc.). In reference to the sensor arrays described herein, the use of the term sensor element includes the use of a nanoscale sensor element for the sensor element and associated methods.

The term "plurality of sensor elements" refers to more than one, for example, at least two sensor elements. In some embodiments, the plurality of sensor elements includes at least two sensor elements to at least $10^{15}$ sensor elements. In some embodiments, the plurality of sensor elements includes $10^6$-$10^7$, $10^6$-$10^8$, $10^6$-$10^9$, $10^6$-$10^{10}$, $10^6$-$10^{11}$, $10^6$-$10^{12}$, $10^6$-$10^{13}$, $10^6$-$10^{14}$, $10^6$-$10^{15}$, $10^7$-$10^8$, $10^7$-$10^9$, $10^7$-$10^{10}$, $10^7$-$10^{11}$, $10^7$-$10^{12}$, $10^7$-$10^{13}$, $10^7$-$10^{14}$, $10^7$-$10^{15}$, $10^8$-$10^9$, $10^8$-$10^{10}$, $10^8$-$10^{11}$, $10^8$-$10^{12}$, $10^8$-$10^{13}$, $10^8$-$10^{14}$, $10^8$-$10^{15}$, $10^9$-$10^{10}$, $10^9$-$10^{11}$, $10^9$-$10^{12}$, $10^9$-$10^{13}$, $10^9$-$10^{14}$, $10^9$-$10^{15}$, $10^{10}$-$10^{11}$, $10^{10}$-$10^{12}$, $10^{10}$-$10^{13}$, $10^{10}$-$10^{14}$, $10^{10}$-$10^{15}$, $10^{11}$-$10^{12}$, $10^{11}$-$10^{13}$, $10^{11}$-$10^{14}$, $10^{11}$-$10^{15}$, $10^{12}$-$10^{13}$, $10^{12}$-$10^{14}$, $10^{12}$-$10^{15}$, $10^{13}$-$10^{14}$, $10^{13}$-$10^{15}$, or $10^{14}$-$10^{15}$ different sensor elements.

In some embodiments, a plurality of sensor elements comprises a plurality of types of sensor elements. A plurality of sensor elements may comprise at least two to at least 1000 types of sensor elements, alternatively at least two to at least 50 types of sensor elements, alternatively at least 2 to 30 types of sensor elements, alternatively at least 2 to 20 types of sensor elements, alternatively at least 2 to 10 types of sensor elements, alternatively at least 3 to at least 50 types of sensor elements, alternatively at least 3 to at least 30 types of sensor elements, alternatively at least 3 to at least 20 types of sensor elements, alternatively at least 3 to at least 10 types of sensor elements, alternatively at least 4 to at least 50 types of sensor elements, alternatively at least 4 to at least 30 types of sensor elements, alternatively at least 4 to at least 20 types of sensor elements, alternatively at least 4 to at least 10 types of sensor elements, and including any number of types of sensor elements contemplated in between (e.g., at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, 200, 225, 250, 300, 350, 400, 450, 500, 550, 600, 650, 700, 750, 800, etc.). The plurality of sensor elements may comprise at least 6 types of sensor elements to at least 20 types of sensor elements, or alternatively at least 6 types of sensor elements to at least 10 types of sensor elements.

Figure 10:
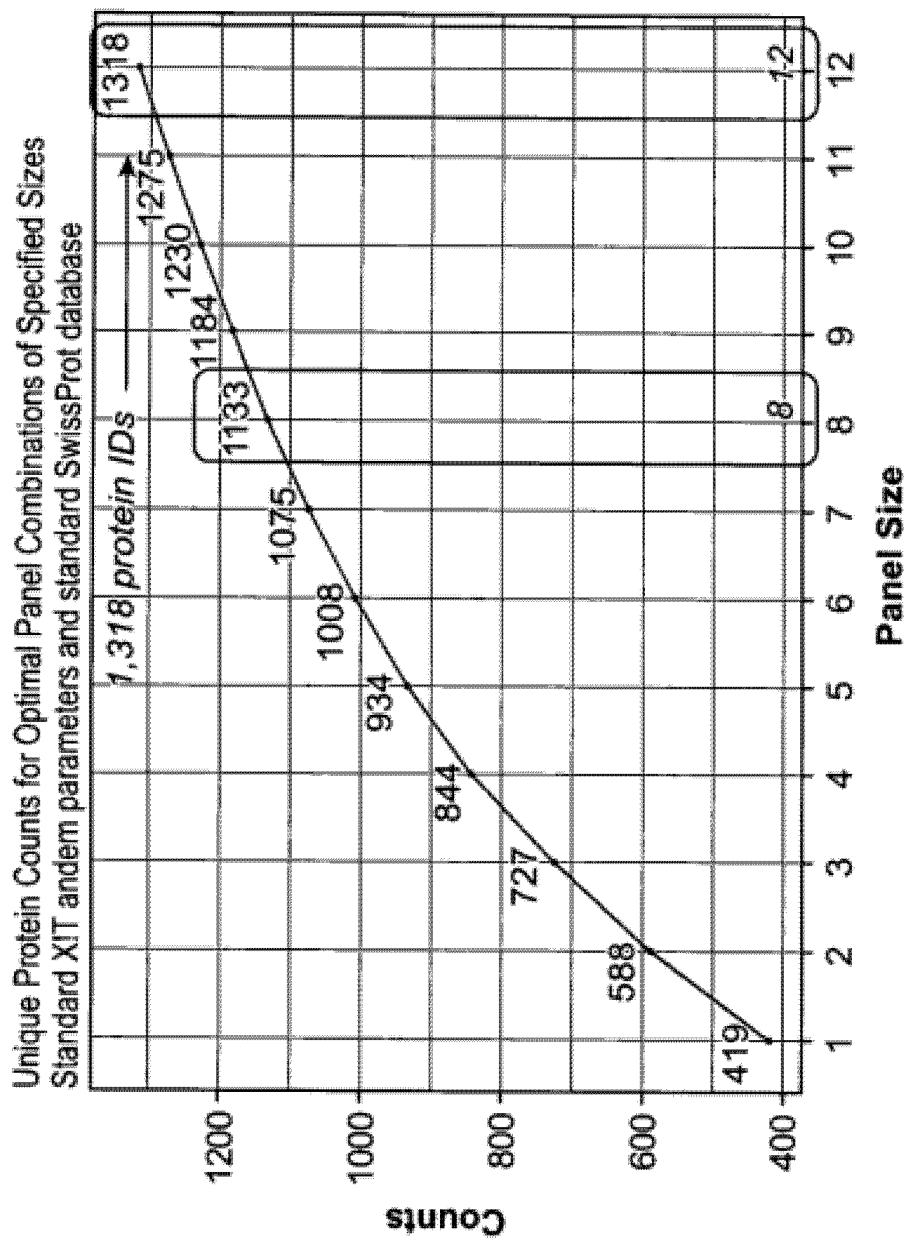
FIG. 10 shows the protein counts (number of proteins identified from corona analysis) collected on pluralities of particles comprising from 1 particle type to 12 particle types. Each particle from among a plurality of particles may be comprise unique materials, surface functionalization, and/or physical property (e.g., size or shape). Pooled plasma from a group of healthy subjects was used. Counts are the numbers of unique proteins collected from a plurality of particles and observed in about 2 hour mass spectrometry (MS) runs. 1318 proteins were identified from the sample contacted with a plurality of particles comprising 12 particle types.

In some cases, increasing the number of sensor elements can be a method for increasing the number of biomolecules (e.g., proteins) that can be identified in a given sample. An example of how increasing panel size may increase the number of identified proteins is shown in FIG. 10. This figure shows the number of proteins identified from corona analysis in assays utilizing panels with 1 to 12 particle types. In these assays, distinct proteins, as opposed to protein groups, were identified through mass spectrometric analysis. The number of types of proteins identified increased with increasing number of particle types, spanning from 419 unique identified proteins when one particle type was used to collect proteins, to 1318 unique identified proteins for when 12 types of particles were used to collect proteins.

The sensor elements may be functionalized to have a wide range of physicochemical properties. Suitable methods of functionalizing the sensor elements are known in the art and depend on composition of the sensor element (e.g. gold, iron oxide, silica, silver, etc.), and include, but are not limited to, for example aminopropyl functionalized, amine functionalized, boronic acid functionalized, carboxylic acid functionalized, methyl functionalized, succinimidyl ester functionalized, PEG functionalized, streptavidin functionalized, methyl ether functionalized, triethoxylpropylaminosilane functionalized, thiol functionalized, PCP functionalized, citrate functionalized, lipoic acid functionalized, BPEI functionalized, carboxyl functionalized, hydroxyl functionalized, and the like. In one embodiment, the sensor elements may be functionalized with an amine group (—$NH_2$ or a carboxyl group (COOH). In some embodiments, the nanoscale sensor elements are functionalized with a polar functional group. Non-limiting examples of the polar functional group comprise carboxyl group, a hydroxyl group, a thiol group, a cyano group, a nitro group, an ammonium group, an imidazolium group, a sulfonium group, a pyridinium group, a pyrrolidinium group, a phosphonium group or any combination thereof. In some embodiments, the functional group is an acidic functional group (e.g., sulfonic acid group, carboxyl group, and the like), a basic functional group (e.g., amino group, cyclic secondary amino group (such as pyrrolidyl group and piperidyl group), pyridyl group, imidazole group, guanidine group, etc.), a carbamoyl group, a hydroxyl group, an aldehyde group and the like. In some embodiments, the polar functional group is an ionic functional group. Non-limiting examples of the ionic function group comprise an ammonium group, an imidazolium group, a sulfonium group, a pyridinium group, a pyrrolidinium group, a phosphonium group. In some embodiments, the sensor elements are functionalized with a polymerizable functional group. Non-limiting examples of the polymerizable functional group include a vinyl group and a (meth) acrylic group. In some embodiments, the functional group is pyrrolidyl acrylate, acrylic acid, methacrylic acid, acrylamide, 2-(dimethylamino)ethyl methacrylate, hydroxyethyl methacrylate and the like.

The physicochemical properties of the sensor elements may be modified by modification of the surface charge. For example, the surface can be modified to provide a net neutral charge, a net positive surface charge, a net negative surface charge, or a zwitterionic charge. The charge of the surface can be controlled either during synthesis of the element or by post-synthesis modification of the charge through surface functionalization. For polymeric sensor elements (e.g., polymeric particles), differences in charge can be obtained during synthesis by using different synthesis procedures, different charged comonomers, and in inorganic substances by having mixed oxidation states.

Non-limiting examples of the plurality of sensor elements include, but are not limited to, (a) a plurality of sensor elements made of the same material but differing in physiochemical properties, (b) a plurality of sensor elements where one or more sensor element is made of a different material with the same or differing physiochemical properties, (c) a plurality of sensor elements made of the same material differing in size, (d) a plurality of sensor elements made of different material with relatively the same size; (e) a plurality of sensor elements made of different material and made of different sizes, (f) a plurality of sensor elements in which each element is made of a different material, (g) a plurality of sensor elements having different charges, among others. The plurality of sensor elements can be in any suitable combination of two or more sensor elements in which each sensor element provides a unique biomolecule corona signature. For example, the plurality of sensor elements may include one or more liposomes and one or more particles described herein. In one embodiment, the plurality of sensor elements can be a plurality of liposomes with varying lipid content and/or varying charges (cationic/anionic/neutral). In another embodiment, the plurality of sensors may contain one or more nanoparticle made of the same material but of varying sizes and physiochemical properties. In another embodiment, the plurality of sensors may contain one or more particle made of differing materials (e.g. silica and polystyrene) with similar or varying sizes and/or physiochemical properties (e.g. modifications, for example, —NH$_2$, —COOH functionalization). These combinations are purely provided as examples and are non-limiting to the scope of the disclosure.

A sensor element may comprise a particle, such as a nanoparticle or a microparticle. A sensor element may be a particle, such as a nanoparticle or a microparticle. A sensor element may comprise a surface or a portion of a surface of a material. A sensor element may comprise a porous material (e.g., a polymer matrix) into which biomolecules can intercalate. A sensor element may comprise a material with projections, such as polymers, oligomers, or metal dendrites. A sensor element may comprise an aggregate of particles, such as a nanoworm.

Particle Materials

A plurality of particles disclosed herein can be made of a variety of different materials. A plurality of particles can comprise specific types of nanoparticles to identify a broad range of proteins in the sample, or to selectively assay for a particular protein or set of proteins of interest.

A plurality of particles may comprise at least 1 particle distinct type, at least 2 distinct particle types, at least 3 distinct particle types, at least 4 distinct particle types, at least 5 distinct particle types, at least 6 distinct particle types, at least 7 distinct particle types, at least 8 distinct particle types, at least 9 distinct particle types, at least 10 distinct particle types, at least 11 distinct particle types, at least 12 distinct particle types, at least 13 distinct particle types, at least 14 distinct particle types, at least 15 distinct particle types, at least 16 distinct particle types, at least 17 distinct particle types, at least 18 distinct particle types, at least 19 distinct particle types, at least 20 distinct particle types, at least 25 distinct particle types, at least 30 distinct particle types, at least 35 distinct particle types, at least 40 distinct particle types, at least 45 distinct particle types, at least 50 distinct particle types, at least 55 distinct particle types, at least 60 distinct particle types, at least 65 distinct particle types, at least 70 distinct particle types, at least 75 distinct particle types, at least 80 distinct particle types, at least 85 distinct particle types, at least 90 distinct particle types, at least 95 distinct particle types, at least 100 distinct particle types, from 1 to 5 distinct particle types, from 5 to 10 distinct particle types, from 10 to 15 distinct particle types, from 15 to 20 distinct particle types, from 20 to 25 distinct particle types, from 25 to 30 distinct particle types, from 30 to 35 distinct particle types, from 35 to 40 distinct particle types, from 40 to 45 distinct particle types, from 45 to 50 distinct particle types, from 50 to 55 distinct particle types, from 55 to 60 distinct particle types, from 60 to 65 distinct particle types, from 65 to 70 distinct particle types, from 70 to 75 distinct particle types, from 75 to 80 distinct particle types, from 80 to 85 distinct particle types, from 85 to 90 distinct particle types, from 90 to 95 distinct particle types, from 95 to 100 distinct particle types, from 1 to 100 distinct particle types, from 20 to 40 distinct particle types, from 5 to 10 distinct particle types, from 3 to 7 distinct particle types, from 2 to 10 distinct particle types, from 6 to 15 distinct particle types, or from 10 to 20 distinct particle types. A plurality of particles may comprise from 3 to 10 particle types. A plurality of particles may comprise from 4 to 11 distinct particle types. A plurality of particles may comprise from 5 to 15 distinct particle types. A plurality of particles may comprise from 5 to 15 distinct particle types. A plurality of particles may comprise from 8 to 12 distinct particle types. A plurality of particles may comprise from 9 to 13 distinct particle types. A plurality of particles may comprise 10 distinct particle types. The particle types may include nanoparticles.

For example, the present disclosure a plurality of particles having at least 2 distinct particle types, at least 3 different surface chemistries, at least 4 different surface chemistries, at least 5 different surface chemistries, at least 6 different surface chemistries, at least 7 different surface chemistries, at least 8 different surface chemistries, at least 9 different surface chemistries, at least 10 different surface chemistries, at least 11 different surface chemistries, at least 12 different surface chemistries, at least 13 different surface chemistries, at least 14 different surface chemistries, at least 15 different surface chemistries, at least 20 different surface chemistries, at least 25 different surface chemistries, at least 30 different surface chemistries, at least 35 different surface chemistries, at least 40 different surface chemistries, at least 45 different surface chemistries, at least 50 different surface chemistries, at least 100 different surface chemistries, at least 150 different surface chemistries, at least 200 different surface chemistries, at least 250 different surface chemistries, at least 300 different surface chemistries, at least 350 different surface chemistries, at least 400 different surface chemistries, at least 450 different surface chemistries, at least 500 different surface chemistries, from 2 to 500 different surface chemistries, from 2 to 5 different surface chemistries, from 5 to 10 different surface chemistries, from 10 to 15 different surface chemistries, from 15 to 20 different surface chemistries, from 20 to 40 different surface chemistries, from 40 to 60 different surface chemistries, from 60 to 80 different surface chemistries, from 80 to 100 different surface chemistries, from 100 to 500 different surface chemistries, from 4 to 15 different surface chemistries, or from 2 to 20 different surface chemistries.

The present disclosure provides a plurality of particles having at least 2 different physical properties, at least 3 different physical properties, at least 4 different physical properties, at least 5 different physical properties, at least 6 different physical properties, at least 7 different physical properties, at least 8 different physical properties, at least 9 different physical properties, at least 10 different physical properties, at least 11 different physical properties, at least 12 different physical properties, at least 13 different physical properties, at least 14 different physical properties, at least 15 different physical properties, at least 20 different physical properties, at least 25 different physical properties, at least 30 different physical properties, at least 35 different physical properties, at least 40 different physical properties, at least 45 different physical properties, at least 50 different physical properties, at least 100 different physical properties, at least 150 different physical properties, at least 200 different physical properties, at least 250 different physical properties, at least 300 different physical properties, at least 350 different physical properties, at least 400 different physical properties, at least 450 different physical properties, at least 500 different physical properties, from 2 to 500 different physical properties, from 2 to 5 different physical properties, from 5 to 10 different physical properties, from 10 to 15 different physical properties, from 15 to 20 different physical properties, from 20 to 40 different physical properties, from 40 to 60 different physical properties, from 60 to 80 different physical properties, from 80 to 100 different physical properties, from 100 to 500 different physical properties, from 4 to 15 different physical properties, or from 2 to 20 different physical properties.

Particles can be made from various materials. For example, nanoparticle materials consistent with the present disclosure include metals, polymers, magnetic materials, and lipids. Magnetic nanoparticles may be iron oxide nanoparticles. Examples of metal materials include any one of or any combination of gold, silver, copper, nickel, cobalt, palladium, platinum, iridium, osmium, rhodium, ruthenium, rhenium, vanadium, chromium, manganese, niobium, molybdenum, tungsten, tantalum, iron and cadmium, or any other material described in U.S. Pat. No. 7,749,299.

Examples of polymers include any one of or any combination of polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, or polyamines, a polyalkylene glycol (e.g., polyethylene glycol (PEG)), a polyester (e.g., poly(lactide-co-glycolide) (PLGA), polylactic acid, or polycaprolactone), or a copolymer of two or more polymers, such as a copolymer of a polyalkylene glycol (e.g., PEG) and a polyester (e.g., PLGA). In some embodiments, the polymer is a lipid-terminated polyalkylene glycol and a polyester, or any other material disclosed in U.S. Pat. No. 9,549,901. A polymer may also be a liposome.

Examples of lipids that can be used to form the nanoparticles of the present disclosure include cationic, anionic, and neutrally charged lipids. For example, nanoparticles can be made of any one of or any combination of dioleoylphosphatidylglycerol (DOPG), diacylphosphatidylcholine, diacylphosphatidylethanolamine, ceramide, sphingomyelin, cephalin, cholesterol, cerebrosides and diacylglycerols, dioleoylphosphatidylcholine (DOPC), dimyristoylphosphatidylcholine (DMPC), and dioleoylphosphatidylserine (DOPS), phosphatidylglycerol, cardiolipin, diacylphosphatidylserine, diacylphosphatidic acid, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), lecithin, lysolecithin, phosphatidylethanolamine, lysophosphatidylethanolamine, dioleoylphosphatidylethanolamine (DOPE), dipalmitoyl phosphatidyl ethanolamine (DPPE), dimyristoylphosphoethanolamine (DMPE), distearoyl-phosphatidyl-ethanolamine (DSPE), palmitoyloleoyl-phosphatidylethanolamine (POPE) palmitoyloleoylphosphatidylcholine (POPC), egg phosphatidylcholine (EPC), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), palmitoyloleyolphosphatidylglycerol (POPG), 16-O-monomethyl PE, 16-O-dimethyl PE, 18-1-trans PE, palmitoyloleoyl-phosphatidylethanolamine (POPE), 1-stearoyl-2-oleoyl-phosphatidyethanolamine (SOPE), phosphatidylserine, phosphatidylinositol, sphingomyelin, cephalin, cardiolipin, phosphatidic acid, cerebrosides, dicetylphosphate, and cholesterol, or any other material listed in U.S. Pat. No. 9,445,994.

In various cases, the core of the nanoparticles can include an organic particle, an inorganic particle, or a particle including both organic and inorganic materials. For example, the particles can have a core structure that is or includes a metal particle, a quantum dot particle, a metal oxide particle, or a core-shell particle. For example, the core structure can be or include a polymeric particle or a lipid-based particle, and the linkers can include a lipid, a surfactant, a polymer, a hydrocarbon chain, or an amphiphilic polymer. For example, the linkers can include polyethylene glycol or polyalkylene glycol, e.g., the first ends of the linkers can include a lipid bound to polyethelene glycol (PEG) and the second ends can include functional groups bound to the PEG. A particle may have a core-shell structure. In some cases, a particle has a core comprising a first material or composite and a plurality of shells comprising different materials or composites. In some cases, a particle has a magnetic core surrounded by a non-magnetic or plurality of non-magnetic shells. For example, a particle may comprise a magnetic iron oxide core surrounded by a non-magnetic polymer shell. In some cases, magnetic core has a 10 nm to 500 nm diameter, and the shell has a 5 nm to 100 nm thickness.

Figure 7:
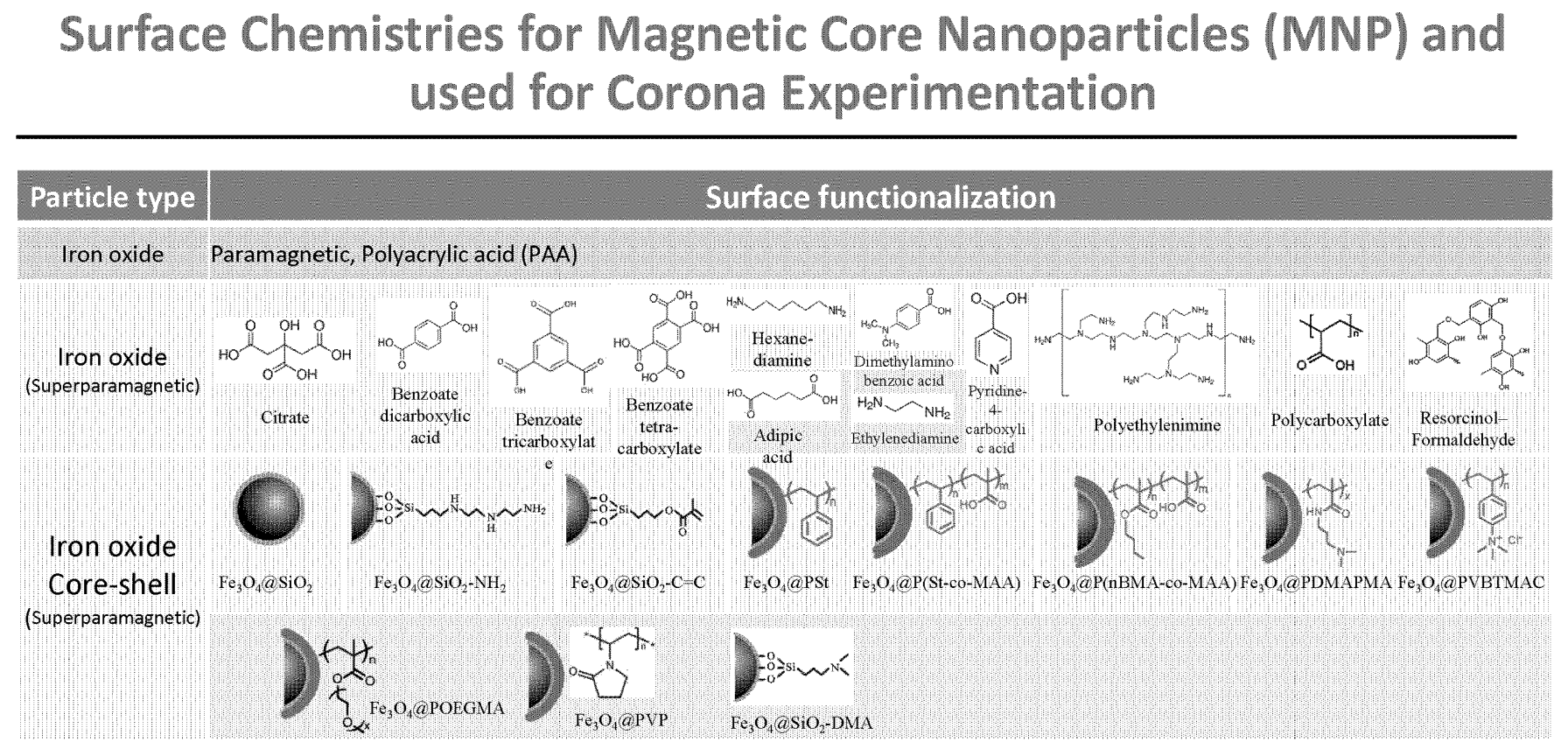

Examples of particle types consistent with the present disclosure are shown in TABLE 1 below. Additional examples of particles, such as magnetic core nanoparticles (MNP) and corresponding surface chemistries are illustrated in FIG. 7.

TABLE 1

Particle Types

| P# | Description | Vendor |
|---|---|---|
| HX-13 or S-001 | Carboxylate (Citrate) | Seer |
| HX-19 or S-002 | Phenol-formaldehyde coated | Seer |
| HX-31 or S-004 | Polystyrene coated | Seer |
| HX-38 or S-005 | Polystyrene/carboxylate coated | Seer |
| HX-42 or S-006 | Silica coated, amine | Seer |
| HX-57 or S-008 | Benzoic acid | Seer |
| HX-58 or S-009 | PVBTMAC coated (Vinylbenzyltrimethylammonium chloride) | Seer |
| HX-59 or S-010 | Carboxylate, PAA coated | Seer |
| P-033 | Carboxylate | Polysciences |
| P-039 | Polystyrene Carboxyl | Micro Particles |
| P-041 | Carboxylic acid | OceanNanoTech |
| P-047 | Silica | OceanNanoTech |
| P-048 | Carboxylic acid | OceanNanoTech |
| P-053 | Amino | Spherotech |
| P-056 | Silica Amino | Spherotech |
| P-063 | Jeffamine | Spherotech |
| P-064 | Polystyrene | Spherotech |
| P-065 | Silica | Spherotech |
| P-069 | Original coating | OceanNanoTech |
| P-073 | Dextran based | Kisker Biotech |
| P-074 | Silica Silanol | Kisker Biotech |
| HX-20 or S-003 | Silica-coated superparamagnetic iron oxide NPs (SPION) | Seer |
| HX-56 or S-007 | poly(N-(3-(dimethylamino)propyl) methacrylamide) (PDMAPMA)-coated SPION | Seer |
| HX-86 or S-011 | poly(oligo(ethylene glycol) methyl ether methacrylate) (POEGMA)-coated SPION | Seer |

Properties of Particles

Nanoparticles that are consistent with the present disclosure can be made and used in methods of forming protein coronas after incubation in a biofluid at a wide range of sizes. For example, the nanoparticles disclosed herein can be at least 10 nm, at least 100 nm, at least 200 nm, at least 300 nm, at least 400 nm, at least 500 nm, at least 600 nm, at least 700 nm, at least 800 nm, at least 900 nm, from 10 nm to 50 nm, from 50 nm to 100 nm, from 100 nm to 150 nm, from 150 nm to 200 nm, from 200 nm to 250 nm, from 250 nm to 300 nm, from 300 nm to 350 nm, from 350 nm to 400 nm, from 400 nm to 450 nm, from 450 nm to 500 nm, from 500 nm to 550 nm, from 550 nm to 600 nm, from 600 nm to 650 nm, from 650 nm to 700 nm, from 700 nm to 750 nm, from 750 nm to 800 nm, from 800 nm to 850 nm, from 850 nm to 900 nm, from 100 nm to 300 nm, from 150 nm to 350 nm, from 200 nm to 400 nm, from 250 nm to 450 nm, from 300 nm to 500 nm, from 350 nm to 550 nm, from 400 nm to 600 nm, from 450 nm to 650 nm, from 500 nm to 700 nm, from 550 nm to 750 nm, from 600 nm to 800 nm, from 650 nm to 850 nm, from 700 nm to 900 nm, or from 10 nm to 900 nm.

Additionally, particles can have a homogenous size distribution or a heterogeneous size distribution. Polydispersity index (PDI), which can be measured by techniques such as dynamic light scattering, is a measure of the size distribution. A low PDI indicates a more homogeneous size distribution and a higher PDI indicates a more heterogeneous size distribution. In some cases, a plurality of particles has a PDI of 0.01 to 0.1, 0.1 to 0.5, 0.5 to 1, 1 to 5, 5 to 20, or greater than 20.

Particles disclosed herein can have a range of different surface charges. Particles can be negatively charged, positively charged, or neutral in charge. In some embodiments, particles have a surface charge of −500 mV to −450 mV, −450 mV to −400 mV, −400 mV to −350 mV, −350 mV to −300 mV, −300 mV to −250 mV, −250 mV to −200 mV, −200 mV to −150 mV, −150 mV to −100 mV, −100 mV to −90 mV, −90 mV to −80 mV, −80 mV to −70 mV, −70 mV to −60 mV, −60 mV to −50 mV, −50 mV to −40 mV, −40 mV to −30 mV, −30 mV to −20 mV, −20 mV to −10 mV, −10 mV to 0 mV, 0 mV to 10 mV, 10 mV to 20 mV, 20 mV to 30 mV, 30 mV to 40 mV, 40 mV to 50 mV, 50 mV to 60 mV, 60 mV to 70 mV, 70 mV to 80 mV, 80 mV to 90 mV, 90 mV to 100 mV, 100 mV to 110 mV, 110 mV to 120 mV, 120 mV to 130 mV, 130 mV to 140 mV, 140 mV to 150 mV, 150 mV to 200 mV, 200 mV to 250 mV, 250 mV to 300 mV, 300 mV to 350 mV, 350 mV to 400 mV, 400 mV to 450 mV, 450 mV to 500 mV, −500 my to −400 mV, −400 my to −300 mV, −300 my to −200 mV, −200 my to −100 mV, −100 my to 0 mV, 0 my to 100 mV, 100 my to 200 mV, 200 my to 300 mV, 300 my to 400 mV, or 400 my to 500 mV.

Various particle morphologies are consistent with the particle types in panels of the present disclosure. For example, particles may be spherical, colloidal, square shaped, rods, wires, cones, pyramids, or oblong.

Biomolecule Coronas

Provided herein are automated apparatuses, systems, methods, and sensor elements capable of generating biomolecule coronas comprising, consisting essentially of or consisting of a plurality of sensor elements wherein the plurality of sensor elements differ from each other in at least one physicochemical property. The plurality of sensor elements may comprise a plurality of particles (e.g., nanoparticles). The plurality of sensor elements may be a plurality of particles. A plurality of sensor elements may be able to bind a plurality of biomolecules in a complex biological sample to produce a biomolecule corona signature. A plurality of sensor elements may comprise a plurality of distinct biomolecule corona signatures.

A biomolecule of interest (e.g., a low abundance protein) may be enriched in a biomolecule corona relative to the untreated sample (e.g., a sample that is not assayed using particles). The biomolecule of interest may be a protein. The biomolecule corona may be a protein corona. A level of enrichment may be the percent increase or fold increase in relative abundance of the biomolecule of interest (e.g., number of copies of the biomolecule of interest versus the total number of biomolecules) in the biomolecule corona as compared to the biological sample from which the biomolecule corona was collected. A biomolecule of interest may be enriched in a biomolecule corona by increasing the abundance of the biomolecule of interest in the biomolecule corona as compared to the sample that has not been contacted to the sensor element. A biomolecule of interest may be enriched by decreasing the abundance of a biomolecule that is in high abundance biological sample.

A biomolecule corona analysis assay may be used to rapidly identify low abundance biomolecules in a biological sample (e.g., a biofluid). Biomolecule corona analysis may be used to identify at least about 500 low abundance biomolecules in a biological sample in no more than about 8 hours from first contacting the biological sample with a sensor element (e.g., a particle). Biomolecule corona analysis may identify at least about 1000 low abundance biomolecules in a biological sample in no more than about 8 hours from first contacting the biological sample with a sensor element. Biomolecule corona analysis may identify at least about 500 low abundance biomolecules in a biological sample in no more than about 4 hours from first contacting the biological sample with a sensor element. Biomolecule corona analysis may identify at least about 1000 low abundance biomolecules in a biological sample in no more than about 4 hours from first contacting the biological sample with a sensor element.

A biomolecule corona signature may comprise a protein, a peptide, a polysaccharide, an oligosaccharide, a monosaccharide, a metabolite, a lipid, a nucleic acid, or any combination thereof. The biomolecule corona signature may be a protein corona signature. The biomolecule corona signature may be a polysaccharide corona signature. The biomolecule corona signature may be a metabolite corona signature. The biomolecule corona signature may be a lipidomic corona signature. The biomolecule corona signature may comprise the biomolecules found in a soft corona and a hard corona. The soft corona may be a soft protein corona. The hard corona may be a hard protein corona.

The biomolecule corona signature refers to the composition, signature or pattern of different biomolecules that are bound to each separate sensor element or each nanoparticle. In some cases, the biomolecule corona signature is a protein corona signature. In another case, the biomolecule corona signature is a polysaccharide corona signature. In yet another case, the biomolecule corona signature is a metabolite corona signature. In some cases, the biomolecule corona signature is a lipidomic corona signature. The signature can refer to the different biomolecules. It can also refer to the differences in the amount, level or quantity of the biomolecule bound to the sensor element or the nanoparticle, or differences in the conformational state of the biomolecule that is bound to the sensor element or the particle. It is contemplated that the biomolecule corona signatures of each sensor elements may contain some of the same biomolecules, may contain distinct biomolecules with regard to the other sensor elements or nanoparticles, and/or may differ in level or quantity, type or confirmation of the biomolecule. The biomolecule corona signature may depend on not only the physicochemical properties of the sensor element or the particle, but also the nature of the sample and the duration of exposure. In some embodiments, the biomolecule corona signature comprises the biomolecules found in a soft corona and a hard corona.

In some embodiments, a plurality of sensor elements includes a first sensor element that produces a first biomolecule corona signature and at least one second sensor element (e.g., at least one nanoparticle) that produces at least one second biomolecule corona signature when the sensor array is contacted with a complex biological sample. In some cases, each type of sensor element from among a plurality of sensor elements produces a different biomolecule corona signature.

The plurality of sensor elements when contacted with a sample produces a plurality of biomolecule corona signatures which together can form a biomolecule fingerprint. The "biomolecule fingerprint" refers to the combined composition or pattern of biomolecules of at least two biomolecule corona signatures for the plurality of sensor elements. It is contemplated that the biomolecule fingerprint can be made from at least two biomolecule corona signatures to as many different biomolecule signatures are assayed, e.g. at least 1000 different biomolecule corona signatures. The biomolecule corona can be assayed separately for each sensor element to determine the biomolecule corona signature for each sensor element (e.g., each nanoparticle or each liposome) and combined to form the biomolecule fingerprint. In some cases, the biomolecule fingerprint can be developed by assaying the two or more biomolecule coronas simultaneously.

Identified Proteins

The automated apparatuses, systems, methods, and sensor elements (e.g., particles) disclosed herein can be used to identify a number of biomolecules, proteins, peptides, or protein groups. Feature intensities, as disclosed herein, refers to the intensity of a signal from an analytical measurement, for example the intensity of a mass to charge ratio from a mass spectrometry run of a sample. Using the data analysis methods described herein, feature intensities of peptides and peptide fragments can be sorted into protein groups. Protein groups refer to two or more proteins that are identified by a shared peptide sequence. Alternatively, a protein group can refer to one protein that is identified using a unique identifying sequence. For example, if in a sample, a peptide sequence is assayed that is shared between two proteins (Protein 1: XYZZX and Protein 2: XYZYZ), a protein group could be the "XYZ protein group" having two members (protein 1 and protein 2). Alternatively, if the peptide sequence is unique to a single protein (Protein 1), a protein group could be the "ZZX" protein group having one member (Protein 1). Each protein group can be supported by more than one peptide sequence. Protein detected or identified according to the instant disclosure can refer to a distinct protein detected in the sample (e.g., distinct relative other proteins detected using mass spectrometry). Thus, analysis of proteins present in distinct coronas corresponding to the distinct sensor element types yields a high number of feature intensities. This number decreases as feature intensities are processed into distinct peptides, further decreases as distinct peptides are processed into distinct proteins, and further decreases as peptides are grouped into protein groups (two or more proteins that share a distinct peptide sequence).

The automated apparatuses, systems, methods, and sensor elements (e.g., particles) disclosed herein can be used to identify at least at least 100 protein groups, at least 200 protein groups, at least 300 protein groups, at least 400 protein groups, at least 500 protein groups, at least 600 protein groups, at least 700 protein groups, at least 800 protein groups, at least 900 protein groups, at least 1000 protein groups, at least 1100 protein groups, at least 1200 protein groups, at least 1300 protein groups, at least 1400 protein groups, at least 1500 protein groups, at least 1600 protein groups, at least 1700 protein groups, at least 1800 protein groups, at least 1900 protein groups, at least 2000 protein groups, at least 2100 protein groups, at least 2200 protein groups, at least 2300 protein groups, at least 2400 protein groups, at least 2500 protein groups, at least 2600 protein groups, at least 2700 protein groups, at least 2800 protein groups, at least 2900 protein groups, at least 3000 protein groups, at least 3100 protein groups, at least 3200 protein groups, at least 3300 protein groups, at least 3400 protein groups, at least 3500 protein groups, at least 3600 protein groups, at least 3700 protein groups, at least 3800 protein groups, at least 3900 protein groups, at least 4000 protein groups, at least 4100 protein groups, at least 4200 protein groups, at least 4300 protein groups, at least 4400 protein groups, at least 4500 protein groups, at least 4600 protein groups, at least 4700 protein groups, at least 4800 protein groups, at least 4900 protein groups, at least 5000 protein groups, at least 10000 protein groups, at least 20000 protein groups, at least 100000 protein groups, from 100 to 5000 protein groups, from 200 to 4700 protein groups, from 300 to 4400 protein groups, from 400 to 4100 protein groups, from 500 to 3800 protein groups, from 600 to 3500 protein groups, from 700 to 3200 protein groups, from 800 to 2900 protein groups, from 900 to 2600 protein groups, from 1000 to 2300 protein groups, from 1000 to 3000 protein groups, from 3000 to 4000 protein groups, from 4000 to 5000 protein groups, from 5000 to 6000 protein groups, from 6000 to 7000 protein groups, from 7000 to 8000 protein groups, from 8000 to 9000 protein groups, from 9000 to 10000 protein groups, from 10000 to 11000 protein groups, from 11000 to 12000 protein groups, from 12000 to 13000 protein groups, from 13000 to 14000 protein groups, from 14000 to 15000 protein groups, from 15000 to 16000 protein groups, from 16000 to 17000 protein groups, from 17000 to 18000 protein groups, from 18000 to 19000 protein groups, from 19000 to 20000 protein groups, from 20000 to 25000 protein groups, from 25000 to 30000 protein groups, from 10000 to 20000 protein groups, from 10000 to 50000 protein groups, from 20000 to 100000 protein groups, from 2000 to 20000 protein groups, from 1800 to 20000 protein groups, or from 10000 to 100000 protein groups.

The automated apparatuses, systems, methods, and sensor elements (e.g., particles) disclosed herein can be used to identify at least at least 100 proteins, at least 200 proteins, at least 300 proteins, at least 400 proteins, at least 500 proteins, at least 600 proteins, at least 700 proteins, at least 800 proteins, at least 900 proteins, at least 1000 proteins, at least 1100 proteins, at least 1200 proteins, at least 1300 proteins, at least 1400 proteins, at least 1500 proteins, at least 1600 proteins, at least 1700 proteins, at least 1800 proteins, at least 1900 proteins, at least 2000 proteins, at least 2100 proteins, at least 2200 proteins, at least 2300 proteins, at least 2400 proteins, at least 2500 proteins, at least 2600 proteins, at least 2700 proteins, at least 2800 proteins, at least 2900 proteins, at least 3000 proteins, at least 3100 proteins, at least 3200 proteins, at least 3300 proteins, at least 3400 proteins, at least 3500 proteins, at least 3600 proteins, at least 3700 proteins, at least 3800 proteins, at least 3900 proteins, at least 4000 proteins, at least 4100 proteins, at least 4200 proteins, at least 4300 proteins, at least 4400 proteins, at least 4500 proteins, at least 4600 proteins, at least 4700 proteins, at least 4800 proteins, at least 4900 proteins, at least 5000 proteins, from 100 to 5000 proteins, from 200 to 4700 proteins, from 300 to 4400 proteins, from 400 to 4100 proteins, from 500 to 3800 proteins, from 600 to 3500 proteins, from 700 to 3200 proteins, from 800 to 2900 proteins, from 900 to 2600 proteins, from 1000 to 2300 proteins, from 1000 to 3000 proteins, from 3000 to 4000 proteins, from 4000 to 5000 proteins, from 5000 to 6000 proteins, from 6000 to 7000 proteins, from 7000 to 8000 proteins, from 8000 to 9000 proteins, from 9000 to 10000 proteins, from 10000 to 11000 proteins, from 11000 to 12000 proteins, from 12000 to 13000 proteins, from 13000 to 14000 proteins, from 14000 to 15000 proteins, from 15000 to 16000 proteins, from 16000 to 17000 proteins, from 17000 to 18000 proteins, from 18000 to 19000 proteins, from 19000 to 20000 proteins, from 20000 to 25000 proteins, from 25000 to 30000 proteins, or from 10000 to 20000 proteins.

The sensor elements disclosed herein can be used to identify the number of distinct proteins disclosed herein, and/or any of the specific proteins disclosed herein, over a wide dynamic range. For example, a plurality of particles disclosed herein comprising distinct particle types, can enrich for proteins in a sample, which can be identified using the methods of the present disclosure, over the entire dynamic range at which proteins are present in a sample (e.g., a plasma sample). A particle panel may include any number of distinct particle types disclosed herein, and may enrich and identify biomolecules over a concentration range of at least 2 to at least 12 orders of magnitude in a sample.

Disease Detection

The systems and methods described herein can be used for detection of markers in a sample from a subject, which are consistent with a particular biological (e.g., disease) state. The biological state may be a disease, disorder, or tissue abnormality. The disease state may be an early phase or intermediate phase disease state.

The systems and methods of the present disclosure can be used to detect a wide range of disease states in a given sample. For example, the systems and methods of the present disclosure can be used to detect a cancer. The cancer may be brain cancer, lung cancer, pancreatic cancer, glioblastoma, meningioma, myeloma, or pancreatic cancer.

In some cases, a biomolecule fingerprint can be used to determine the disease state of a subject, diagnose or prognose a disease in a subject or identify unique patterns of biomarkers that are associated with a disease state or a disease or disorder. For example, the changes in the biomolecule fingerprint in a subject over time (days, months, years) allows for the ability to track a disease or disorder in a subject (e.g. disease state) which may be broadly applicable to determination of a biomolecule fingerprint that can be associated with the early stage of a disease or any other disease state. As disclosed herein, the ability to detect a disease early on, for example cancer, even before it fully develops or metastasizes allows for a significant increase in positive outcomes for those patients and the ability to increase life expectancy and lower mortality associated with that disease.

The automated apparatuses, systems, methods, and sensor elements (e.g., particles) disclosed herein can provide a unique opportunity to be able to develop biomolecule fingerprints associated with the pre-stages or precursor states of the disease in a high-throughput fashion. The present disclosure provides for large scale, fast processing of samples to generate biomolecule fingerprints in a high throughput manner, thereby allowing for large scale determination of disease state of a subject, diagnosis or prognosis a disease in a subject or identification of unique patterns of biomarkers that are associated with a disease state or a disease or disorder, across many subjects.

In some embodiments, a method of detecting a disease or disorder in a subject are provided. The method comprises the steps of (a) obtaining a sample from the subject; (b) contacting the sample with a sensor array as described herein, and (c) determining a biomolecule fingerprint associated with the sample, wherein the biomolecule fingerprint differentiates the health of subject in a disease state, for example, from no disease or disorder, having a precursor of a disease or disorder, and having disease or disorder.

Determining whether a biomolecule fingerprint associated with the sample may comprise detecting the biomolecule corona signature for at least two sensor elements, wherein the combination of the at least two biomolecule corona signatures produces the biomolecule fingerprint. In some embodiments, the biomolecule corona signatures of the at least two sensor elements are assayed separately, and the results combined to determine the biomolecule fingerprint. In some embodiments the biomolecule corona signatures of the at least two elements are assayed at the same time or in the same sample.

The automated apparatuses, systems, sensor arrays, and methods described herein can be used to determine a disease state, and/or prognose or diagnose a disease or disorder. The diseases or disorders contemplated include, but are not limited to, for example, cancer, cardiovascular disease, endocrine disease, inflammatory disease, a neurological disease and the like.

In one embodiment, the disease or disorder is cancer. The term "cancer" is meant to encompass any cancer, neoplastic and preneoplastic disease that is characterized by abnormal growth of cells, including tumors and benign growths. Cancer may, for example, be lung cancer, pancreatic cancer, or skin cancer. In suitable embodiments, the automated apparatuses, systems, sensor arrays, and methods described herein are not only able to diagnose cancer (e.g. determine if a subject (a) does not have cancer, (b) is in a pre-cancer development stage, (c) is in early stage of cancer, (d) is in a late stage of cancer) but in some embodiments is able to determine the type of cancer. As demonstrated in the examples below, a sensor array comprising six sensor elements was able to accurately determine the disease state of the presence or absence of cancer. Additionally, the Examples demonstrate that a sensor array comprising six sensor elements was able to distinguish between different cancer types (e.g. lung cancer, glioblastoma, meningioma, myeloma and pancreatic cancer).

The automated apparatuses, systems, sensor arrays, and methods of the present disclosure can additionally be used to detect other cancers, such as acute lymphoblastic leukemia (ALL); acute myeloid leukemia (AML); cancer in adolescents; adrenocortical carcinoma; childhood adrenocortical carcinoma; unusual cancers of childhood; AIDS-related cancers; kaposi sarcoma (soft tissue sarcoma); AIDS-related lymphoma (lymphoma); primary cns lymphoma (lymphoma); anal cancer; appendix cancer—see gastrointestinal carcinoid tumors; astrocytomas, childhood (brain cancer); atypical teratoid/rhabdoid tumor, childhood, central nervous system (brain cancer); basal cell carcinoma of the skin—see skin cancer; bile duct cancer; bladder cancer; childhood bladder cancer; bone cancer (includes ewing sarcoma and osteosarcoma and malignant fibrous histiocytoma); brain tumors; breast cancer; childhood breast cancer; bronchial tumors, childhood; burkitt lymphoma—see non-hodgkin lymphoma; carcinoid tumor (gastrointestinal); childhood carcinoid tumors; carcinoma of unknown primary; childhood carcinoma of unknown primary; cardiac (heart) tumors, childhood; central nervous system; atypical teratoid/rhabdoid tumor, childhood (brain cancer); embryonal tumors, childhood (brain cancer); germ cell tumor, childhood (brain cancer); primary cns lymphoma; cervical cancer; childhood cervical cancer; childhood cancers; cancers of childhood, unusual; cholangiocarcinoma—see bile duct cancer; chordoma, childhood; chronic lymphocytic leukemia (CLL); chronic myelogenous leukemia (CML); chronic myeloproliferative neoplasms; colorectal cancer; childhood colorectal cancer; craniopharyngioma, childhood (brain cancer); cutaneous t-cell lymphoma—see lymphoma (mycosis fungoides and sézary syndrome); ductal carcinoma in situ (DCIS)—see breast cancer; embryonal tumors, central nervous system, childhood (brain cancer); endometrial cancer (uterine cancer); ependymoma, childhood (brain cancer); esophageal cancer; childhood esophageal cancer; esthesioneuroblastoma (head and neck cancer); ewing sarcoma (bone cancer); extracranial germ cell tumor, childhood; extragonadal germ cell tumor; eye cancer; childhood intraocular melanoma; intraocular melanoma; retinoblastoma; fallopian tube cancer; fibrous histiocytoma of bone, malignant, and osteosarcoma; gallbladder cancer; gastric (stomach) cancer; childhood gastric (stomach) cancer; gastrointestinal carcinoid tumor; gastrointestinal stromal tumors (GIST) (soft tissue sarcoma); childhood gastrointestinal stromal tumors; germ cell tumors; childhood central nervous system germ cell tumors (brain cancer); childhood extracranial germ cell tumors; extragonadal germ cell tumors; ovarian germ cell tumors; testicular cancer; gestational trophoblastic disease; hairy cell leukemia; head and neck cancer; heart tumors, childhood; hepatocellular (liver) cancer; histiocytosis, langerhans cell; hodgkin lymphoma; hypopharyngeal cancer (head and neck cancer); intraocular melanoma; childhood intraocular melanoma; islet cell tumors, pancreatic neuroendocrine tumors; kaposi sarcoma (soft tissue sarcoma); kidney (renal cell) cancer; langerhans cell histiocytosis; laryngeal cancer (head and neck cancer); leukemia; lip and oral cavity cancer (head and neck cancer); liver cancer; lung cancer (non-small cell and small cell); childhood lung cancer; lymphoma; male breast cancer; malignant fibrous histiocytoma of bone and osteosarcoma; melanoma; childhood melanoma; melanoma, intraocular (eye); childhood intraocular melanoma; merkel cell carcinoma (skin cancer); mesothelioma, malignant; childhood mesothelioma; metastatic cancer; metastatic squamous neck cancer with occult primary (head and neck cancer); midline tract carcinoma with nut gene changes; mouth cancer (head and neck cancer); multiple endocrine neoplasia syndromes; multiple myeloma/plasma cell neoplasms; mycosis fungoides (lymphoma); myelodysplastic syndromes, myelodysplastic/myeloproliferative neoplasms; myelogenous leukemia, chronic (cml); myeloid leukemia, acute (aml); myeloproliferative neoplasms, chronic; nasal cavity and paranasal sinus cancer (head and neck cancer); nasopharyngeal cancer (head and neck cancer); neuroblastoma; non-hodgkin lymphoma; non-small cell lung cancer; oral cancer, lip and oral cavity cancer and oropharyngeal cancer (head and neck cancer); osteosarcoma and malignant fibrous histiocytoma of bone; ovarian cancer; childhood ovarian cancer; pancreatic cancer; childhood pancreatic cancer; pancreatic neuroendocrine tumors (islet cell tumors); papillomatosis (childhood laryngeal); paraganglioma; childhood paraganglioma; paranasal sinus and nasal cavity cancer (head and neck cancer); parathyroid cancer; penile cancer; pharyngeal cancer (head and neck cancer); pheochromocytoma; childhood pheochromocytoma; pituitary tumor; plasma cell neoplasm/multiple myeloma; pleuropulmonary blastoma; pregnancy and breast cancer; primary central nervous system (CNS) lymphoma; primary peritoneal cancer; prostate cancer; rectal cancer; recurrent cancer; renal cell (kidney) cancer; retinoblastoma; rhabdomyosarcoma, childhood (soft tissue sarcoma); salivary gland cancer (head and neck cancer); sarcoma; childhood rhabdomyosarcoma (soft tissue sarcoma); childhood vascular tumors (soft tissue sarcoma); ewing sarcoma (bone cancer); kaposi sarcoma (soft tissue sarcoma); osteosarcoma (bone cancer); soft tissue sarcoma; uterine sarcoma; sézary syndrome (lymphoma); skin cancer; childhood skin cancer; small cell lung cancer; small intestine cancer; soft tissue sarcoma; squamous cell carcinoma of the skin—see skin cancer; squamous neck cancer with occult primary, metastatic (head and neck cancer); stomach (gastric) cancer; childhood stomach (gastric) cancer; t-cell lymphoma, cutaneous—see lymphoma (mycosis fungoides and sézary syndrome); testicular cancer; childhood testicular cancer; throat cancer (head and neck cancer); nasopharyngeal cancer; oropharyngeal cancer; hypopharyngeal cancer; thymoma and thymic carcinoma; thyroid cancer; transitional cell cancer of the renal pelvis and ureter (kidney (renal cell) cancer); carcinoma of unknown primary; childhood cancer of unknown primary; unusual cancers of childhood; ureter and renal pelvis, transitional cell cancer (kidney (renal cell) cancer; urethral cancer; uterine cancer, endometrial; uterine sarcoma; vaginal cancer; childhood vaginal cancer; vascular tumors (soft tissue sarcoma); vulvar cancer; wilms tumor and other childhood kidney tumors; or cancer in young adults.

In some cases, the disease or disorder is cardiovascular disease. As used herein, the terms "cardiovascular disease" (CVD) or "cardiovascular disorder" are used to classify numerous conditions affecting the heart, heart valves, and vasculature (e.g., veins and arteries) of the body and encompasses diseases and conditions including, but not limited to atherosclerosis, myocardial infarction, acute coronary syndrome, angina, congestive heart failure, aortic aneurysm, aortic dissection, iliac or femoral aneurysm, pulmonary embolism, atrial fibrillation, stroke, transient ischemic attack, systolic dysfunction, diastolic dysfunction, myocarditis, atrial tachycardia, ventricular fibrillation, endocarditis, peripheral vascular disease, and coronary artery disease (CAD). Further, the term cardiovascular disease refers to subjects that ultimately have a cardiovascular event or cardiovascular complication, referring to the manifestation of an adverse condition in a subject brought on by cardiovascular disease, such as sudden cardiac death or acute coronary syndrome, including, but not limited to, myocardial infarction, unstable angina, aneurysm, stroke, heart failure, non-fatal myocardial infarction, stroke, angina pectoris, transient ischemic attacks, aortic aneurysm, aortic dissection, cardiomyopathy, abnormal cardiac catheterization, abnormal cardiac imaging, stent or graft revascularization, risk of experiencing an abnormal stress test, risk of experiencing abnormal myocardial perfusion, and death.

As used herein, the ability to detect, diagnose or prognose cardiovascular disease, for example, atherosclerosis, can include determining if the patient is in a pre-stage of cardiovascular disease, has developed early, moderate or severe forms of cardiovascular disease, or has suffered one or more cardiovascular event or complication associated with cardiovascular disease.

Atherosclerosis (also known as arteriosclerotic vascular disease or ASVD) is a cardiovascular disease in which an artery-wall thickens as a result of invasion and accumulation and deposition of arterial plaques containing white blood cells on the innermost layer of the walls of arteries resulting in the narrowing and hardening of the arteries. The arterial plaque is an accumulation of macrophage cells or debris, and contains lipids (cholesterol and fatty acids), calcium and a variable amount of fibrous connective tissue. Diseases associated with atherosclerosis include, but are not limited to, atherothrombosis, coronary heart disease, deep venous thrombosis, carotid artery disease, angina pectoris, peripheral arterial disease, chronic kidney disease, acute coronary syndrome, vascular stenosis, myocardial infarction, aneurysm or stroke. In one embodiment the automated apparatuses, compositions, and methods of the present disclosure may distinguish the different stages of atherosclerosis, including, but not limited to, the different degrees of stenosis in a subject.

In some cases, the disease or disorder is an endocrine disease. The term "endocrine disease" is used to refer to a disorder associated with dysregulation of endocrine system of a subject. Endocrine diseases may result from a gland producing too much or too little of an endocrine hormone causing a hormonal imbalance, or due to the development of lesions (such as nodules or tumors) in the endocrine system, which may or may not affect hormone levels. Suitable endocrine diseases able to be treated include, but are not limited to, e.g., Acromegaly, Addison's Disease, Adrenal Cancer, Adrenal Disorders, Anaplastic Thyroid Cancer, Cushing's Syndrome, De Quervain's Thyroiditis, Diabetes, Follicular Thyroid Cancer, Gestational Diabetes, Goiters, Graves' Disease, Growth Disorders, Growth Hormone Deficiency, Hashimoto's Thyroiditis, Hurthle Cell Thyroid Cancer, Hyperglycemia, Hyperparathyroidism, Hyperthyroidism, Hypoglycemia, Hypoparathyroidism, Hypothyroidism, Low Testosterone, Medullary Thyroid Cancer, MEN 1, MEN 2A, MEN 2B, Menopause, Metabolic Syndrome, Obesity, Osteoporosis, Papillary Thyroid Cancer, Parathyroid Diseases, Pheochromocytoma, Pituitary Disorders, Pituitary Tumors, Polycystic Ovary Syndrome, Prediabetes, Silent, Thyroiditis, Thyroid Cancer, Thyroid Diseases, Thyroid Nodules, Thyroiditis, Turner Syndrome, Type 1 Diabetes, Type 2 Diabetes, and the like.

In some cases, the disease or disorder is an inflammatory disease. As referred to herein, inflammatory disease refers to a disease caused by uncontrolled inflammation in the body of a subject. Inflammation is a biological response of the subject to a harmful stimulus which may be external or internal such as pathogens, necrosed cells and tissues, irritants etc. However, when the inflammatory response becomes abnormal, it results in self-tissue injury and may lead to various diseases and disorders. Inflammatory diseases can include, but are not limited to, asthma, glomerulonephritis, inflammatory bowel disease, rheumatoid arthritis, hypersensitivities, pelvic inflammatory disease, autoimmune diseases, arthritis; necrotizing enterocolitis (NEC), gastroenteritis, pelvic inflammatory disease (PID), emphysema, pleurisy, pyelitis, pharyngitis, angina, acne vulgaris, urinary tract infection, appendicitis, bursitis, colitis, cystitis, dermatitis, phlebitis, rhinitis, tendonitis, tonsillitis, vasculitis, autoimmune diseases; celiac disease; chronic prostatitis, hypersensitivities, reperfusion injury; sarcoidosis, transplant rejection, vasculitis, interstitial cystitis, hay fever, periodontitis, atherosclerosis, psoriasis, ankylosing spondylitis, juvenile idiopathic arthritis, Behcet's disease, spondyloarthritis, uveitis, systemic lupus erythematosus, and cancer. For example, the arthritis includes rheumatoid arthritis, psoriatic arthritis, osteoarthritis or juvenile idiopathic arthritis, and the like.

The disease or disorder may be a neurological disease. Neurological disorders or neurological diseases are used interchangeably and refer to diseases of the brain, spine and the nerves that connect them. Neurological diseases include, but are not limited to, brain tumors, epilepsy, Parkinson's disease, Alzheimer's disease, ALS, arteriovenous malformation, cerebrovascular disease, brain aneurysms, epilepsy, multiple sclerosis, Peripheral Neuropathy, Post-Herpetic Neuralgia, stroke, frontotemporal dementia, demyelinating disease (including but are not limited to, multiple sclerosis, Devic's disease (i.e. neuromyelitis optica), central pontine myelinolysis, progressive multifocal leukoencephalopathy, leukodystrophies, Guillain-Barre syndrome, progressing inflammatory neuropathy, Charcot-Marie-Tooth disease, chronic inflammatory demyelinating polyneuropathy, and anti-MAG peripheral neuropathy) and the like. Neurological disorders also include immune-mediated neurological disorders (IMNDs), which include diseases with at least one component of the immune system reacts against host proteins present in the central or peripheral nervous system and contributes to disease pathology. IMNDs may include, but are not limited to, demyelinating disease, paraneoplastic neurological syndromes, immune-mediated encephalomyelitis, immune-mediated autonomic neuropathy, myasthenia gravis, autoantibody-associated encephalopathy, and acute disseminated encephalomyelitis.

Methods, systems, and/or apparatuses of the present disclosure may be able to accurately distinguish between patients with or without Alzheimer's disease. These may also be able to detect patients who are pre-symptomatic and may develop Alzheimer's disease several years after the screening. This provides advantages of being able to treat a disease at a very early stage, even before development of the disease.

The systems, methods, and apparatuses of the present disclosure can detect a pre-disease stage of a disease or disorder. A pre-disease stage is a stage at which the patient has not developed any signs or symptoms of the disease. A pre-cancerous stage would be a stage in which cancer or tumor or cancerous cells have not be identified within the subject. A pre-neurological disease stage would be a stage in which a person has not developed one or more symptom of the neurological disease. The ability to diagnose a disease before one or more sign or symptom of the disease is present allows for close monitoring of the subject and the ability to treat the disease at a very early stage, increasing the prospect of being able to halt progression or reduce the severity of the disease.

The automated apparatuses, systems, sensor arrays, and methods of the present disclosure in some embodiments are able to detect the early stages of a disease or disorder. Early stages of the disease can refer to when the first signs or symptoms of a disease may manifest within a subject. The early stage of a disease may be a stage at which there are no outward signs or symptoms. For example, in Alzheimer's disease an early stage may be a pre-Alzheimer's stage in which no symptoms are detected yet the patient will develop Alzheimer's months or years later.

Identifying a disease in either pre-disease development or in the early states may often lead to a higher likelihood for a positive outcome for the patient. For example, diagnosing cancer at an early stage (stage 0 or stage 1) can increase the likelihood of survival by over 80%. Stage 0 cancer can describe a cancer before it has begun to spread to nearby tissues. This stage of cancer is often highly curable, usually by removing the entire tumor with surgery. Stage 1 cancer may usually be a small cancer or tumor that has not grown deeply into nearby tissue and has not spread to lymph nodes or other parts of the body.

Figure 8:
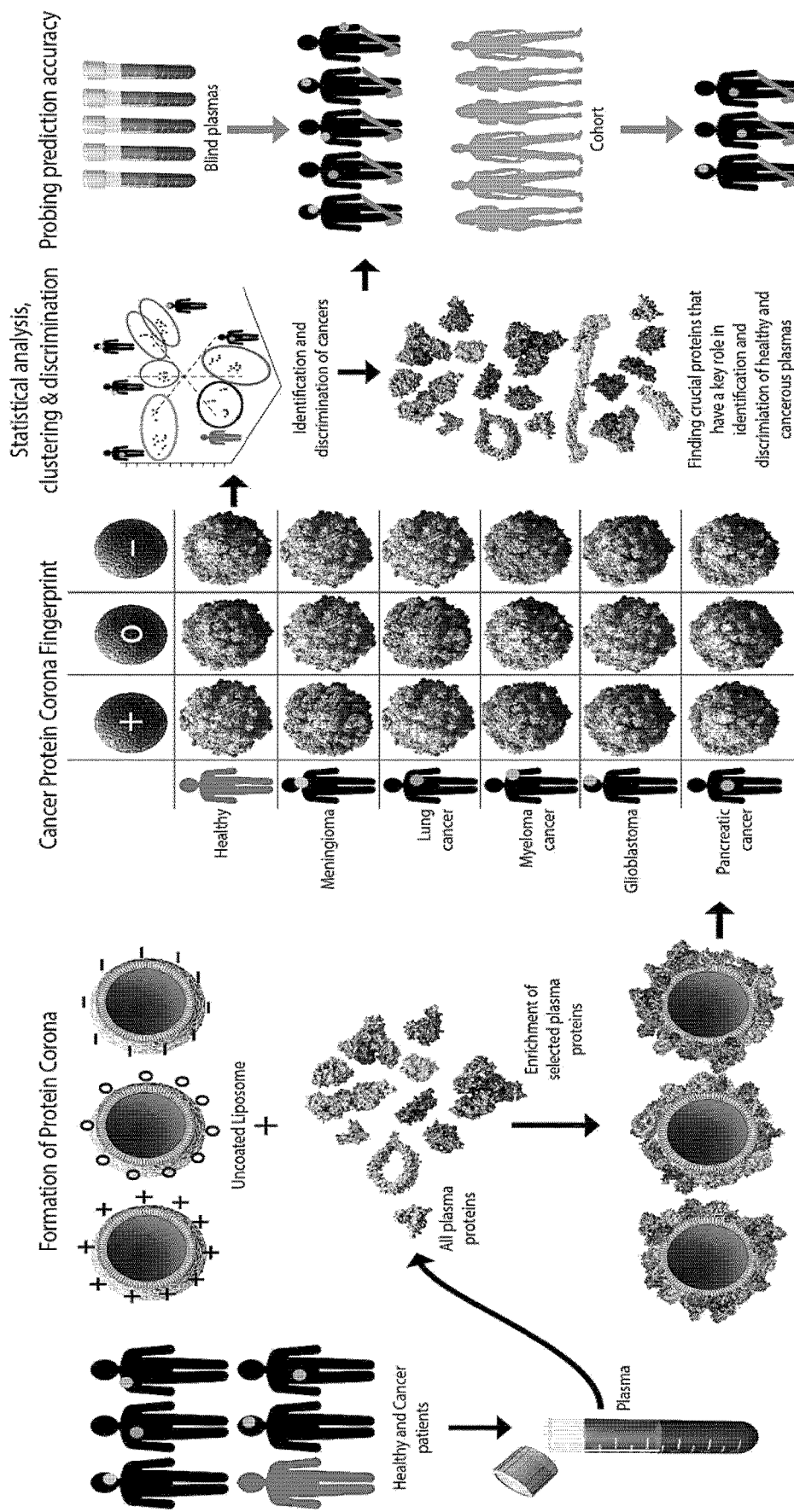
FIG. 8 shows an example of protein corona-based methods for detecting disease biomarkers in a cancer patient (referring to US20180172694A1, incorporated by reference in its entirety herein).

FIG. 8 presents a schematic overview of a cancer detection method that can be performed using the automated apparatus of the present disclosure. Whole blood samples can be collected from a range of patients, including healthy patients and patients with different types and stages of cancer. The whole blood can be fractionated into plasma samples, and then contacted with a plurality of types of particles, including positively charged, negatively charged, and neutral particles. Each particle type collects different types of proteins from the plasma samples, leading to each patient having a unique biomolecule fingerprint. The biomolecule fingerprint not only comprise the relative abundances of proteins on each particle type, but also the relative abundances of proteins across particle types. For example, an increase in the abundance of fibronectin on a first particle type may be a relevant indicator only when the abundance of complement component 4 is low on a second particle type. The biomolecule fingerprints can not only be used to determine which patients have cancer, but also to determine the stages and types of the cancers.

In some embodiments, the automated apparatuses, systems, sensor arrays, and methods are able to detect intermediate stages of the disease. Intermediate states of the disease describe stages of the disease that have passed the first signs and symptoms and the patient is experiencing one or more symptom of the disease. For example, for cancer, stage II or III cancers are considered intermediate stages, indicating larger cancers or tumors that have grown more deeply into nearby tissue. In some instances, stage II or III cancers may have also spread to lymph nodes but not to other parts of the body.

Further, the automated apparatuses, systems, sensor arrays, and methods are able to detect late or advanced stages of the disease. Late or advanced stages of the disease may also be called "severe" or "advanced" and usually indicates that the subject is suffering from multiple symptoms and effects of the disease. For example, severe stage cancer includes stage IV, where the cancer has spread to other organs or parts of the body and is sometimes referred to as advanced or metastatic cancer.

The methods of the present disclosure can include processing the biomolecule fingerprint of the sample against a collection of biomolecule fingerprints associated with a plurality of diseases and/or a plurality of disease states to determine if the sample indicates a disease and/or disease state. For example, samples can be collected from a population of subjects over time. Once the subjects develop a disease or disorder, the present disclosure allows for the ability to characterize and detect the changes in biomolecule fingerprints over time in the subject by computationally analyzing the biomolecule fingerprint of the sample from the same subject before they have developed a disease to the biomolecule fingerprint of the subject after they have developed the disease. Samples can also be taken from cohorts of patients who all develop the same disease, allowing for analysis and characterization of the biomolecule fingerprints that are associated with the different stages of the disease for these patients (e.g. from pre-disease to disease states).

In some cases, the apparatuses, systems, compositions, and methods of the present disclosure are able to distinguish not only between different types of diseases, but also between the different stages of the disease (e.g. early stages of cancer). This can comprise distinguishing healthy subjects from pre-disease state subjects. The pre-disease state may be stage 0 or stage 1 cancer, a neurodegenerative disease, dementia, a coronary disease, a kidney disease, a cardiovascular disease (e.g., coronary artery disease), diabetes, or a liver disease. Distinguishing between different stages of the disease can comprise distinguishing between two stages of a cancer (e.g., stage 0 vs stage 1 or stage 1 vs stage 3).

Sample

The panels of the present disclosure can be used to generate proteomic data from protein coronas and subsequently associated with any of the biological states described herein. Samples consistent with the present disclosure include biological samples from a subject. The subject may be a human or a non-human animal. Biological samples may be a biofluid. For example, the biofluid may be plasma, serum, CSF, urine, tear, or saliva. Said biological samples can contain a plurality of proteins or proteomic data, which may be analyzed after adsorption of proteins to the surface of the various sensor element (e.g., particle) types in a panel and subsequent digestion of protein coronas. Proteomic data can comprise nucleic acids, peptides, or proteins.

A wide range of biological samples are compatible for use within the automated apparatuses of the present disclosure. The biological sample may comprise plasma, serum, urine, cerebrospinal fluid, synovial fluid, tears, saliva, whole blood, milk, nipple aspirate, ductal lavage, vaginal fluid, nasal fluid, ear fluid, gastric fluid, pancreatic fluid, trabecular fluid, lung lavage, sweat, crevicular fluid, semen, prostatic fluid, sputum, fecal matter, bronchial lavage, fluid from swabbings, bronchial aspirants, fluidized solids, fine needle aspiration samples, tissue homogenates, lymphatic fluid, cell culture samples, or any combination thereof. The biological sample may comprise multiple biological samples (e.g., pooled plasma from multiple subjects, or multiple tissue samples from a single subject). The biological sample may comprise a single type of biofluid or biomaterial from a single source.

The biological sample may be diluted or pre-treated. The biological sample may undergo depletion (e.g., the biological sample comprises serum) prior to use within the automated apparatus. The biological sample may also undergo physical (e.g., homogenization or sonication) or chemical treatment prior to use within the automated apparatus. The biological sample may be diluted prior to use within the automated apparatus. The dilution medium may comprise buffer or salts, or be purified water (e.g., distilled water). Different partitions of a biological sample may undergo different degrees of dilution. A biological sample or sample partition may undergo a 1.1-fold, 1.2-fold, 1.3-fold, 1.4-fold, 1.5-fold, 2-fold, 3-fold, 4-fold, 5-fold, 6-fold, 8-fold, 10-fold, 12-fold, 15-fold, 20-fold, 30-fold, 40-fold, 50-fold, 75-fold, 100-fold, 200-fold, 500-fold, or 1000-fold dilution.

In some embodiments, the panels of the present disclosure provide identification and measurement of particular proteins in the biological samples by processing of the proteomic data via digestion of coronas formed on sensor elements. Examples of proteins that can be identified and measured include highly abundant proteins, proteins of medium abundance, and low-abundance proteins. Examples of proteins that are highly abundant proteins include albumin and IgG.

In some embodiments, examples of proteins that can be measured and identified include albumin, immunoglobulin G (IgG), lysozyme, carcino embryonic antigen (CEA), receptor tyrosine-protein kinase erbB-2 (HER-2/neu), bladder tumor antigen, thyroglobulin, alpha-fetoprotein, prostate specific antigen (PSA), mucin 16 (CA125), carbohydrate antigen 19-9 (CA19.9), carcinoma antigen 15-3 (CA15.3), leptin, prolactin, osteopontin, insulin-like growth factor 2 (IGF-II), 4F2 cell-surface antigen heavy chain (CD98), fascin, sPigR, 14-3-3 eta, troponin I, B-type natriuretic peptide, breast cancer type 1 susceptibility protein (BRCA1), c-Myc proto-oncogene protein (c-Myc), interleukin-6 (IL-6), fibrinogen. Epidermal growth factor receptor (EGFR), gastrin, PH, Granulocyte colony-stimulating factor (G CSF), desmin, enolase 1 (NSE), folice-stimulating hormone (FSH), vascular endothelial growth factor (VEGF), P21, Proliferating cell nuclear antigen (PCNA), calcitonin, pathogenesis-related proteins (PR), luteinizing hormone (LH), somatostatin. S100, insulin. alpha-prolactin, Adrenocorticotropic hormone (ACTH), B-cell lymphoma 2 (Bcl 2), estrogen receptor alpha (ER alpha), antigen k (Ki-67), tumor protein (p53), cathepsin D, beta catenin, von Willebrand factor (VWF), CD15, k-ras, caspase 3, ENTH domain-containing protein (EPN), CD10, FAS, breast cancer type 2 susceptibility protein (BRCA2), CD30L, CD30, CGA, CRP, prothrombin, CD44, APEX, transferrin, GM-CSF, E-cadherin, interleukin-2 (IL-2), Bax, IFN-gamma, beta-2-MG, tumor necrosis factor alpha (TNF alpha), cluster of differentiation 340, trypsin, cyclin D1, MG B, XBP-1, HG-1, YKL-40, S-gamma, NESP-55, netrin-1, geminin, GADD45A, CDK-6, CCL21, breast cancer metastasis suppressor 1 (BrMS1), 17betaHDI, platelet-derived growth factor receptor A (PDGRFA), P300/CBP-associated factor (Pcaf), chemokine ligand 5 (CCL5), matrix metalloproteinase-3 (MMP3), claudin-4, and claudin-3.

Methods of Analysis

The proteomic data of the sample can be identified, measured, and quantified using a number of different analytical techniques. For example, proteomic data can be analyzed using sodium dodecyl sulfate polyacrylamide gel electrophoresis (SDS-PAGE) or any gel-based separation technique. Peptides and proteins can also be identified, measured, and quantified using an immunoassay, such as an enzyme-linked immunosorbent assay (ELISA). Alternatively, proteomic data can be identified, measured, and quantified using mass spectrometry, high performance liquid chromatography, LC-MS/MS, and other protein separation techniques.

In some cases, the method of determining the biomolecule fingerprint comprises detecting and determining the biomolecular corona signatures of the at least two sensor elements. This step can be done by separating the plurality of biomolecules attached to each sensor element (e.g. separating the biomolecule corona from the sensor element) and assaying the plurality of biomolecules to determine the composition of the plurality of biomolecule coronas to determine a biomolecule fingerprint. In some cases, the composition of each biomolecule corona signature of each sensor element is assayed independently, and the results are combined to produce the biomolecule fingerprint (e.g. each sensor element is in a separate channel or compartment wherein the specific composition of the biomolecule corona for that specific sensor element can be separately analyzed (e.g. either by detaching the biomolecules and assaying by mass spectrometry and/or chromatography or by detecting the plurality of biomolecules still attached to the sensor element by fluorescence, luminescence or other means). The at least two sensor elements may also be in the same partition and the composition of the biomolecule corona for the at least two sensor elements is assayed at the same time by dissociating the biomolecule corona from both sensor elements into one solution and assaying that solution to determining a biomolecule signature.

Methods of assaying the plurality of biomolecules that make up the biomolecule corona signature or the biomolecule fingerprint may include, but are not limited to, for example, gel-electrophoresis, liquid chromatography, mass spectrometry, nuclear magnetic resonance spectroscopy (NMR), Fourier transform infrared spectroscopy (FTIR), circular dichroism, Raman spectrometry, and a combination thereof. In some cases, the assaying comprises an analyte specific identification technique, such as ELISA, immunostaining, or nucleic acid capture by hybridization. In a preferred embodiment, the assaying comprises liquid chromatography, mass spectrometry or a combination thereof.

As disclosed herein, nucleic acids may be processed by standard molecular biology techniques for downstream applications. Embodiments of the methods and compositions disclosed herein relate to nucleic acid (polynucleotide) sequencing. In some methods and compositions described herein, the nucleotide sequence of a portion of a target nucleic acid or fragment thereof may be determined using a variety of methods and devices. Examples of sequencing methods include electrophoretic, sequencing by synthesis, sequencing by ligation, sequencing by hybridization, single-molecule sequencing, and real time sequencing methods. In some embodiments, the process to determine the nucleotide sequence of a target nucleic acid or fragment thereof may be an automated process. In some embodiments, capture probes may function as primers permitting the priming of a nucleotide synthesis reaction using a polynucleotide from the nucleic acid sample as a template. In this way, information regarding the sequence of the polynucleotides supplied to the array may be obtained. In some embodiments, polynucleotides hybridized to capture probes on the array may serve as sequencing templates if primers that hybridize to the polynucleotides bound to the capture probes and sequencing reagents are further supplied to the array. Methods of sequencing using arrays have been described previously in the art.

In some embodiments involving sequencing on a substrate such as an array, paired end reads may be obtained on nucleic acid clusters. Methods for obtaining paired end reads are described in WO/07010252 and WO/07091077, each of which is incorporated herein by reference in its entirety. Paired end sequencing facilitates reading both the forward and reverse template strands of each cluster during one paired-end read. Generally, template clusters may be amplified on the surface of a substrate (e.g. a flow-cell) by bridge amplification and sequenced by paired primers sequentially. Upon amplification of the template strands, a bridged double stranded structure may be produced. This may be treated to release a portion of one of the strands of each duplex from the surface. The single stranded nucleic acid may be available for sequencing, primer hybridization and cycles of primer extension. After the first sequencing run, the ends of the first single stranded template may be hybridized to the immobilized primers remaining from the initial cluster amplification procedure. The immobilized primers may be extended using the hybridized first single strand as a template to resynthesize the original double stranded structure. The double stranded structure may be treated to remove at least a portion of the first template strand to leave the resynthesized strand immobilized in single stranded form. The resynthesized strand may be sequenced to determine a second read, whose location originates from the opposite end of the original template fragment obtained from the fragmentation process.

Nucleic acid sequencing may be single-molecule sequencing or sequencing by synthesis. Sequencing may be massively parallel array sequencing (e.g., Illumina™ sequencing), which may be performed using template nucleic acid molecules immobilized on a support, such as a flow cell. For example, sequencing may comprise a first-generation sequencing method, such as Maxam-Gilbert or Sanger sequencing, or a high-throughput sequencing (e.g., next-generation sequencing or NGS) method. A high-throughput sequencing method may sequence simultaneously (or substantially simultaneously) at least about 10,000, 100,000, 1 million, 10 million, 100 million, 1 billion, or more polynucleotide molecules. Sequencing methods may include, but are not limited to: pyrosequencing, sequencing-by synthesis, single-molecule sequencing, nanopore sequencing, semiconductor sequencing, sequencing-by-ligation, sequencing-by-hybridization, Digital Gene Expression (Helicos), massively parallel sequencing, e.g., Helicos, Clonal Single Molecule Array (Solexa/Illumina), sequencing using PacBio, SOLiD, Ion Torrent, or Nanopore platforms.

A sensor element may comprise a complex with a first component and a polymer fluorophore or other quencher component chemically complementary to the first component where such a complex having an initial background or reference fluorescence. Once the first component comes into contact with a biomolecule (e.g., upon formation of a biomolecule corona), it can affect the quenching of the fluorophore and this change in fluorescence can be measured. After the sensor is irradiated and/or excited with a laser, the effect and/or change in fluorescence for each sensor element can be measured and compared to or processed against the background fluorescence to produce the biomolecule fingerprint.

Computer Systems

The present disclosure provides computer control systems that are programmed to implement methods of the disclosure. This determination, analysis or statistical classification is done by methods known in the art, including, but not limited to, for example, a wide variety of supervised and unsupervised data analysis and clustering approaches such as hierarchical cluster analysis (HCA), principal component analysis (PCA), Partial least squares Discriminant Analysis (PLSDA), machine learning (also known as random forest), logistic regression, decision trees, support vector machine (SVM), k-nearest neighbors, naive bayes, linear regression, polynomial regression, SVM for regression, K-means clustering, and hidden Markov models, among others. The computer system can perform various aspects of analyzing the protein sets or protein corona of the present disclosure, such as, for example, comparing/analyzing the biomolecule corona of several samples to determine with statistical significance what patterns are common between the individual biomolecule coronas to determine a protein set that is associated with the biological state. The computer system can be used to develop classifiers to detect and discriminate different protein sets or protein corona (e.g., characteristic of the composition of a protein corona). Data collected from the presently disclosed sensor array can be used to train a machine learning algorithm, specifically an algorithm that receives array measurements from a patient and outputs specific biomolecule corona compositions from each patient. Before training the algorithm, raw data from the array can be first denoised to reduce variability in individual variables.

Machine learning can be generalized as the ability of a learning machine to perform accurately on new, unseen examples/tasks after having experienced a learning data set. Machine learning may include the following concepts and methods. Supervised learning concepts may. include AODE; Artificial neural network, such as Backpropagation, Autoencoders, Hopfield networks, Boltzmann machines, Restricted Boltzmann Machines, and Spiking neural networks; Bayesian statistics, such as Bayesian network and Bayesian knowledge base; Case-based reasoning; Gaussian process regression; Gene expression programming; Group method of data handling (GMDH); Inductive logic programming; Instance-based learning; Lazy learning;

Learning Automata; Learning Vector Quantization; Logistic Model Tree; Minimum message length (decision trees, decision graphs, etc.), such as Nearest Neighbor Algorithm and Analogical modeling; Probably approximately correct learning (PAC) learning; Ripple down rules, a knowledge acquisition methodology; Symbolic machine learning algorithms; Support vector machines; Random Forests; Ensembles of classifiers, such as Bootstrap aggregating (bagging) and Boosting (meta-algorithm); Ordinal classification; Information fuzzy networks (IFN); Conditional Random Field; ANOVA; Linear classifiers, such as Fisher's linear discriminant, Linear regression, Logistic regression, Multinomial logistic regression, Naive Bayes classifier, Perceptron, Support vector machines; Quadratic classifiers; k-nearest neighbor; Boosting; Decision trees, such as C4.5, Random forests, ID3, CART, SLIQ SPRINT; Bayesian networks, such as Naive Bayes; and Hidden Markov models. Unsupervised learning concepts may include; Expectation-maximization algorithm; Vector Quantization; Generative topographic map; Information bottleneck method; Artificial neural network, such as Self-organizing map; Association rule learning, such as, Apriori algorithm, Eclat algorithm, and FPgrowth algorithm; Hierarchical clustering, such as Singlelinkage clustering and Conceptual clustering; Cluster analysis, such as, K-means algorithm, Fuzzy clustering, DBSCAN, and OPTICS algorithm; and Outlier Detection, such as Local Outlier Factor. Semi-supervised learning concepts may include; Generative models; Low-density separation; Graph-based methods; and Co-training.

Reinforcement learning concepts may include; Temporal difference learning; Q-learning; Learning Automata; and SARSA. Deep learning concepts may include; Deep belief networks; Deep Boltzmann machines; Deep Convolutional neural networks; Deep Recurrent neural networks; and Hierarchical temporal memory. A computer system may be adapted to implement a method described herein. The system includes a central computer server that is programmed to implement the methods described herein. The server includes a central processing unit (CPU, also "processor") which can be a single core processor, a multi core processor, or plurality of processors for parallel processing. The server also includes memory (e.g., random access memory, read-only memory, flash memory); electronic storage unit (e.g. hard disk); communications interface (e.g., network adaptor) for communicating with one or more other systems; and peripheral devices which may include cache, other memory, data storage, and/or electronic display adaptors. The memory, storage unit, interface, and peripheral devices are in communication with the processor through a communications bus (solid lines), such as a motherboard. The storage unit can be a data storage unit for storing data. The server is operatively coupled to a computer network ("network") with the aid of the communications interface. The network can be the Internet, an intranet and/or an extranet, an intranet and/or extranet that is in communication with the Internet, a telecommunication or data network. The network in some cases, with the aid of the server, can implement a peer-to-peer network, which may enable devices coupled to the server to behave as a client or a server.

The storage unit can store files, such as subject reports, and/or communications with the data about individuals, or any aspect of data associated with the present disclosure.

The computer server can communicate with one or more remote computer systems through the network. The one or more remote computer systems may be, for example, personal computers, laptops, tablets, telephones, Smart phones, or personal digital assistants.

In some applications the computer system includes a single server. In other situations, the system includes multiple servers in communication with one another through an intranet, extranet and/or the internet.

The server can be adapted to store measurement data or a database as provided herein, patient information from the subject, such as, for example, medical history, family history, demographic data and/or other clinical or personal information of potential relevance to a particular application. Such information can be stored on the storage unit or the server and such data can be transmitted through a network.

Methods as described herein can be implemented by way of machine (or computer processor) executable code (or software) stored on an electronic storage location of the server, such as, for example, on the memory, or electronic storage unit. During use, the code can be executed by the processor. In some cases, the code can be retrieved from the storage unit and stored on the memory for ready access by the processor. In some situations, the electronic storage unit can be precluded, and machine-executable instructions are stored on memory.

Alternatively, the code can be executed on a second computer system.

Aspects of the systems and methods provided herein, such as the server, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical, and electromagnetic waves, such as used across physical interfaces between local devices, through wired and optical landline networks and over various air-links. The physical elements that carry such waves, such as wired or wireless likes, optical links, or the like, also may be considered as media bearing the software. As used herein, unless restricted to non-transitory, tangible "storage" media, terms such as computer or machine "readable medium" can refer to any medium that participates in providing instructions to a processor for execution.

The computer systems described herein may comprise computer-executable code for performing any of the algorithms or algorithms-based methods described herein. In some applications the algorithms described herein will make use of a memory unit that is comprised of at least one database.

Data relating to the present disclosure can be transmitted over a network or connections for reception and/or review by a receiver. The receiver can be but is not limited to the subject to whom the report pertains; or to a caregiver thereof, e.g., a health care provider, manager, other health care professional, or other caretaker; a person or entity that performed and/or ordered the analysis. The receiver can also be a local or remote system for storing such reports (e.g. servers or other systems of a "cloud computing" architecture). In one embodiment, a computer-readable medium includes a medium suitable for transmission of a result of an analysis of a biological sample using the methods described herein.

Aspects of the systems and methods provided herein can be embodied in programming. Various aspects of the technology may be thought of as "products" or "articles of manufacture" typically in the form of machine (or processor) executable code and/or associated data that is carried on or embodied in a type of machine readable medium. Machine executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide nontransitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (TR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

EXAMPLES

The following examples are included to further describe some aspects of the present disclosure and should not be used to limit the scope of the disclosure.

Example 1: Formation of Protein Coronas with Magnetic Nanoparticles and Biofluid with Full Resuspension This exemplary procedure applies to creating protein coronas manually in biofluid samples using a panel of magnetic nanoparticles with full resuspension of nanoparticles. The systems and methods of the present disclosure may apply the procedures described herein.

Materials

The materials used in creating protein coronas is shown in TABLE 2.

TABLE 2

| Equipment and reagents used in creating protein coronas | | |
|---|---|---|
| Equipment and Reagent | Supplier | Part number or Model Number |
| Reagent Grade Water | TEKNOVA | W1210 or equivalent |
| Reagent Grade Water | Corning | 46-002-LF or equivalent |
| Microplate F-Bottom | Greiner | 655901 |
| Aluminum Adhesive Plate Sealers | VWR | 29445-080 or equivalent |
| Microplate Shaker | VWR | 12620-926 or equivalent |
| Vortexer | VWR | 33570 or equivalent |
| Analytical Balance | Mettler Toledo | XP205 |
| Single-channel pipettes (100-1000 μL) | Rainin | L-1000 or equivalent |
| Single-channel pipettes(20-200 μL) | Rainin | L-200 or equivalent |
| Multi-channel pipette (100-1200 μL) | Rainin | E12-1200 or equivalent |
| Pipette tips (1000 μL) | Rainin | GPS-L1000 or equivalent |
| Pipette tips (20-200 μL) | Rainin | GPS-L250 or equivalent |
| 50 mL Reagent Reservoirs | VWR | 82026-355 or equivalent |
| 1x TE pH 7.4 | Quality Biological | 351-010-131 |
| CHAPS | Fisher | BP571-5 |
| Potassium Chloride (KCl) | J. T. Baker | 4001-01 |
| Corning 1 L bottle | Corning | 430518 |
| Nalgene Rapid Flow 1000 mL 0.1 μm or 0.2 μm filter set | Nalgene | 567-0010 or 567-0020 |

Storage and Handling

The following reagents were stored at room temperature, as shown in TABLE 3:

TABLE 3

| Reagents stored at room temperature | | |
|---|---|---|
| Reagent | Supplier | Part Number |
| 1x TE pH 7.4 | Quality Biological | 351-010-131 |
| CHAPS | Fisher | BP571-5 |
| Potassium Chloride (KCl) | J. T. Baker | 4001-01 |
| Reagent Grade Water | TEKNOVA | W1210 |
| Reagent Grade Water | Corning | 46-002-LF |
| TE 150 mM KCl 0.05% CHAPS | Seer Inc. | SOP003 |

The following reagents were stored at about 2-8° C., as shown in TABLE 4:

TABLE 4

| Reagents stored at 2-8° C. | | |
|---|---|---|
| Reagent | Supplier | Part number |
| TE 150 mM KCl 0.05% CHAPS | Seer Inc. | SOP003 |

Preparation

Biofluid samples were removed from the freezer and thawed thoroughly. The nanoparticles were sonicated and vortexed about 10 minutes before use. The TE 150 mM KCl 0.050% CHAPS buffer was prepared before beginning the assay.

TE 150 mM KCl 0.050% CHAPS Buffer Preparation. 11.18 g potassium chloride and 500 mg CHAPS were added to a Corning 1 L bottle. 998.3 g of 1×TE pH7.4 buffer was added. Using a house vacuum, the buffer was filtered with a 0.1 m or 0.2 μm 1000 mL filter set. The buffer can be stored at room temperature (for about 1 month) or at 2-8° C. (for longer than 1 month). The buffer was mixed well before use.

Nanoparticles Preparation. The nanoparticles (aqueous) were diluted in Reagent Grade water to appropriate designated concentration. For dry powder nanoparticles, the dry powder nanoparticles were measured out on a scale before adding the appropriate volume of water to create needed concentration.

Samples Preparation. The samples were removed from the freezer. The samples were thawed thoroughly, and the samples were centrifuged at 16,000 G for about 2 minutes. The samples were either diluted with TE 150 mM KCl 0.05% CHAPS Buffer (1:5) or kept as neat.

Figure 9:
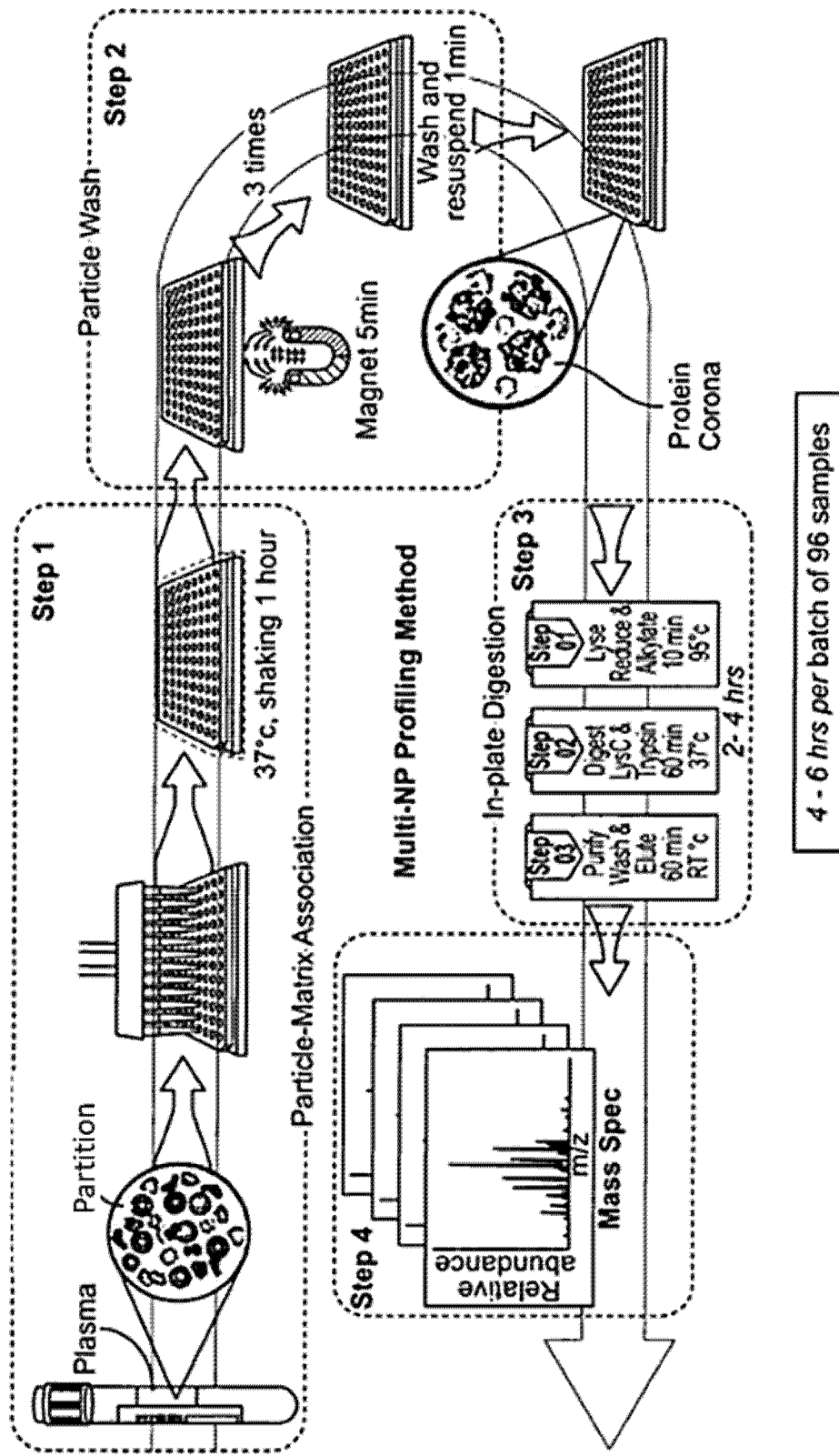
FIG. 9 shows a process for proteomic analysis. The process is tailored for high-throughput and automation that can be run in hours and across multiple samples in parallel. The process includes particle-matrix association, particle wash (×3), formation of the protein corona, in-plate digestion, and mass spectrometry. Using the process, it may take only 4 to 6 hours per batch of 96 samples. One nanoparticle, or more, at a time may be incubated with a sample.

FIG. 9 illustrates a sample preparation method consistent with the present disclosure. This method comprises 4 steps that generate a subset of biomolecules from a biological sample and then use the subset of biomolecules to generate a biomolecule fingerprint. The first step comprises transferring a plasma sample into a plurality of partitions (e.g., wells within a well plate) which comprises a plurality of sensor elements (e.g., magnetic nanoparticles). The sample is incubated within the partitions for 1 hour at 37° C. with shaking, thereby generating biomolecule coronas on the sensor elements. The plurality of partitions is then subjected to a magnetic field that is sufficiently strong to immobilize the sensor elements within the plurality of partitions. The plurality of partitions are then subjected to three washes (e.g., sequential addition and removal of a resuspension buffer) to remove biomolecules that did not adsorb to the sensor elements. After the 3$^{rd}$ wash, the particles are resuspended in buffer, resulting in the desorption of a subset of biomolecules from the biomolecule coronas. The subset of biomolecules is then subjected to a set of denaturation and chemical treatment steps, including heating to 95° C., reduction and alkylation, protease digestion, and further washes. The subset of biomolecules is then submitted for mass spectrometric analysis, which generates a biomolecule fingerprint for the sample.

Procedure

The reagents and equipment were prepared as described in the previous section (see "Preparation"). 100 μL of diluted nanoparticles were loaded into each well using a multichannel pipette. 100 μL of diluted samples per nanoparticle well were added using a pipette. The wells were mixed by aspiration with a pipette about 10 times. The plate was covered with an adhesive plate sealer and incubated for about 1 hours at 37° C. on a plate shaker set to 300 rpm. After the about 1-hour incubation, the adhesive plate sealer was removed, and the plate was placed on a magnet for about 5 minutes to form a nanoparticle corona pellet at the well bottom. For washing, the supernatant was removed with a multichannel pipette. About 200 μL of TE 150 mM KCl 0.05% CHAPS Buffer was added using a pipette and fully resuspended the nanoparticles. The solution was placed back on the magnet for about 5 minutes. The washing step was repeated 3 times. The nanoparticle pellet was resuspended in an appropriate reagent for BCA, gel or trypsin digestion.

Example 2: Trypsin Gold Digest

Materials

The materials used in the trypsin gold digest is shown in TABLE 5.

TABLE 5

Reagents used in the trypsin gold digest

| Reagent | Supplier | Part Number |
| --- | --- | --- |
| Seppro Ammonium Bicarbonate | Sigma | 52454-200 mL |
| Urea | Fisher | BP169-500 |
| DL-Dithiothreitol (DTT) | Sigma | 4381-5G |
| Iodoacetamide (IAA) | GBiosciences | 786-078 |
| Trypsin Gold | Promega | V5280 |
| Acetic Acid | VWR | BDH3096-2.5LPC |

Preparation 50 mM ABC (Ammonium Bicarbonate). 0.25 mL of 2M ABC was added to 9.75 mL of water to yield 10 mL of 50 mM ABC. The solution was vortexed and stored at 4° C. for up to a week.

8M Urea. 4.8 g of urea was weighed and 50 mM of ABC was added until close to about the 10 mL mark. The solution was vortexed and optionally swirled in 37° C. incubator to help dissolve. 50 mM ABC was added to the 10 mL mark and vortexed.

200 mM DTT. 0.031 g of DTT was weighed and 1 mL 50 mM ABC was added. The solution was vortexed and stored away from light at 4° C.

200 mM IAA. 400 uL 50 mM ABC was added to 0.015 g of premeasured IAA. The solution was vortexed and stored at 4° C. The solution was made right before use.

Trypsin Gold Reconstitution. The solution was prepared as per manufacture PI instructions. 100 uL of 50 mM Acetic Acid was added to 100 ug of trypsin, and vortexed. The final concentration was 1 μg/uL trypsin.

Sample/Trypsin Preparation 40 uL of 8M of urea was added to each sample. The solution was vortexed and sonicated for about 1 min. 2 uL of 200 mM DTT was added to each sample, and vortexed. The solution was incubated at room temperature for about 30 min in the dark. 8 uL of 200 mM IAA was added to each sample, and vortexed. The solution was incubated at room temperature for about 30 min in the dark. 8 uL of 200 mM DTT was added to each sample, and vortexed. The solution was incubated at room temperature for about 30 min in the dark. 50 mM ABC was added so that the added urea was less than 2M. 110 uL of 50 mM ABC was added into 58 uL of sample. The appropriate amount of trypsin was added to the samples. 3 uL of reconstituted trypsin was added to each tube. The ratio of protein:trypsin=~30 ug protein:1 ug trypsin. The solution was incubated at 37° C. overnight. 17 uL of 10% FA was added to stop digestion.

Example 3: Proteomic Analysis of NSCLC Samples and Healthy Controls

This example describes proteomic analysis of NSCLC samples and healthy controls. To demonstrate the utility of the corona analysis platform, the platform's ability was evaluated using a single particle type, poly(N-(3-(dimethylamino)propyl) methacrylamide) (PDMAPMA)-coated SPIONs, and serum samples from 56 subjects (28 with Stage IV NSCLC and 28 age- and gender-matched controls) to observe differences between the groups. The selected subject samples represented a reasonably balanced study to identify potential MS features that are different between the groups.

Full data on subject annotation including disease status and co-morbidities are compiled in TABLE 5.

TABLE 6

Gender and age information for the patients from whom the serum samples were obtained.

| Class | Gender | Age Mean (Standard Deviation) | Number |
|---|---|---|---|
| Healthy (Control) | Female | 71.1(7.7) | 19 |
|  | Male | 72.4(11.1) | 9 |
| Non Small Cell Lung Cancer (Diseased) | Female | 70.7(7.5) | 19 |
|  | Male | 75.6(13.6) | 9 |

Figure 11:
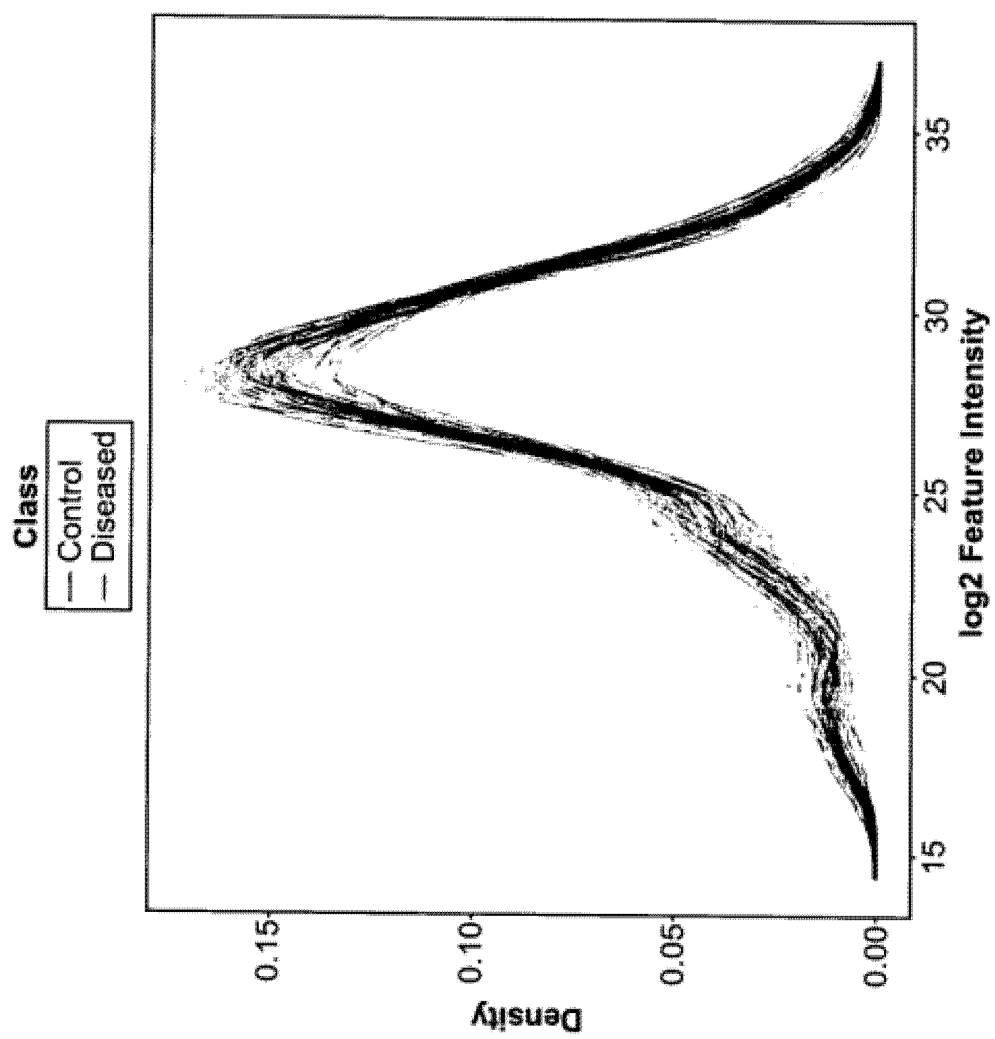
FIG. 11 shows the distribution of the presence-filtered, cluster quality-filtered, median-normalized MS feature intensities for the 56-sample NSCLC comparative study. Each line represents the density of the $\log_2$ feature intensity for either a diseased sample or a control sample. Density is plotted from 0.00 to 0.15 on the y-axis, and $\log_2$ feature intensity is plotted from 15 to 35 on the x-axis. At the highest peak located near a $\log_2$ feature intensity of about 28, with densities ranging from about 0.13 to about 0.17, the two highest traces correspond to control samples, while the lowest trace corresponds to a diseased sample. The remaining control and diseased traces are distributed between the highest and lowest traces. At the two shoulder peaks, occurring at about 20 $\log_2$ feature intensity and about 23 $\log_2$ feature intensity, the highest two traces are control traces and the lowest two traces are control traces at the 20 $\log_2$ feature intensity peak, and the highest traces is a diseased trace at the 23 $\log_2$ feature intensity.

After collection and filtering of the MS1 features followed by log 2 transformation of their intensity, the datasets were median scaled without respect to class. FIG. 11 shows the normalized intensity distributions for all 56 subject datasets. All 56 sample MS raw data files from the NSCLC versus control study were processed by OpenMS pipeline scripts to extract MS1 features and their intensities and cluster them into feature groups based on overlapping mz and RT values within specified tolerances. Only those feature groups were retained that 1) had at least 50% presence of a feature in the group from at least one of the arms of the comparison and 2) had a feature group cluster quality above the 25th percentile. The retained features were median normalized without respect to class and used for subsequent univariate analytical comparison. There were no outliers by inspection of the distributions and all datasets were retained for the univariate analysis.

Figure 12:
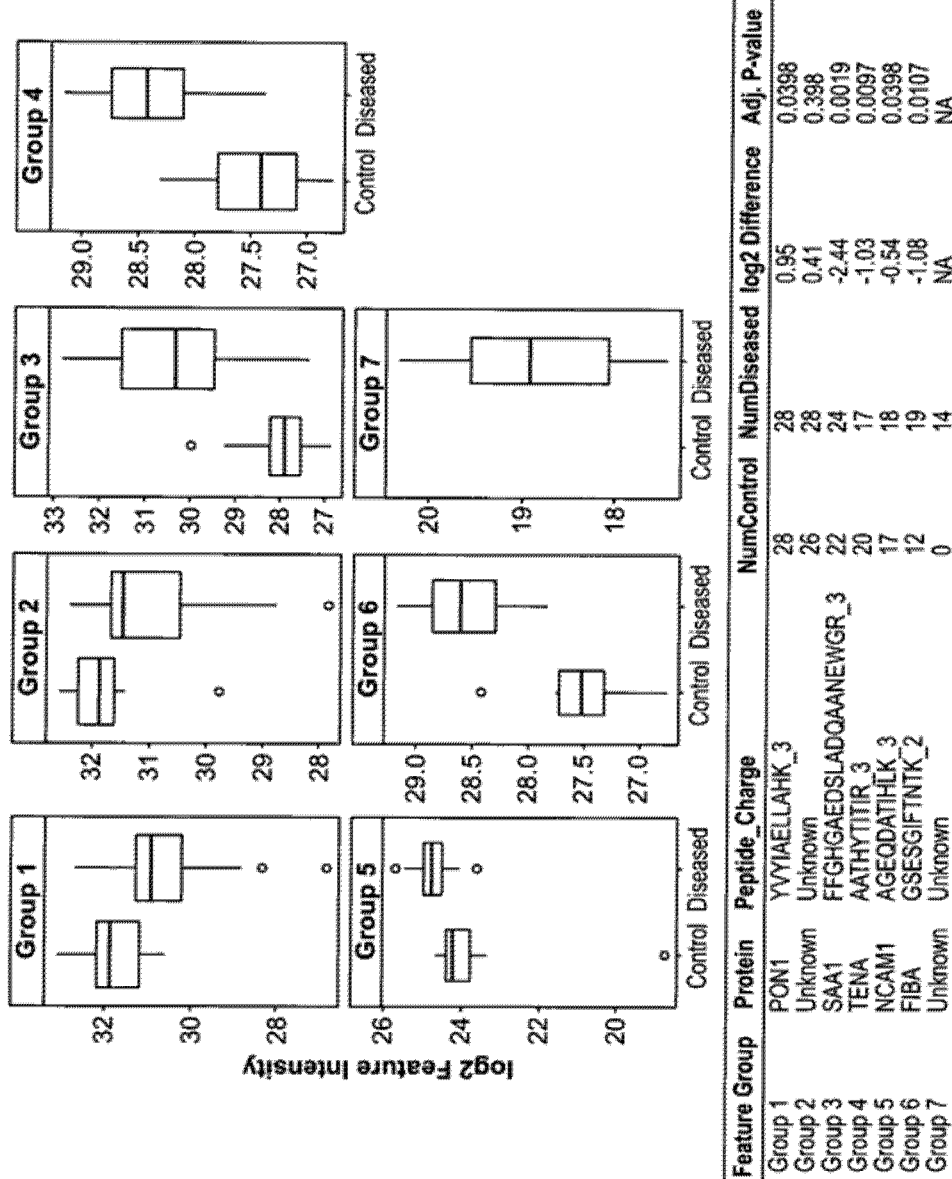
FIG. 12 shows changed features in a non-small cell lung cancer (NSCLC) pilot study using poly(N-(3-(dimethylamino)propyl) methacrylamide) (PDMAPMA)-coated SPION particles. Seven MS features were identified as statistically, significantly different between 28 subjects with Stage IV NSCLC (with associated co-morbidities and treatment effects) and 28 age- and gender-matched, apparently healthy subjects. The table at bottom is a list of the seven proteins that were significantly different. This includes 5 known proteins and 2 unknown proteins. If a peptide-spectrum match was made for MS2 data associated with the feature, that peptide sequence (and charge) as well as the potential parent protein are indicated; if an MS2 match was not associated with the feature, both the peptide and the protein are marked as "Unknown".

There did not appear to be any outlier datasets by inspection. Univariate comparison of feature group intensities between the classes was performed with a non-parametric, Wilcoxon Test (two-sided). The resulting p-value for the comparison was corrected for multiple testing using the method of Benjamini-Hochberg. Using an adjusted p-value cut-off of 0.05, a total of seven feature groups demonstrated statistical significance, as summarized in FIG. 12.

All five of the proteins identified as differentially abundant between the NSCLC-diseased and control groups have previously been implicated in cancer if not actually NSCLC itself. PON1, or paraoxanase-1, has a complicated pattern in lung cancer including the involvement of a relatively common minor allele variant (Q192R) as a risk factor. At the protein level, PON1 is modestly decreased in lung adenocarcinoma. SAA1 is an acute phase protein that has been shown to be overexpressed in NSCLC in MS-related studies, and the identified peptide was found to be increased 5.4-fold in diseased subjects. The matrisome factor tenascin C (TENA) has been shown to be increased in primary lung tumors and associated lymph node metastases compared with normal tissue, and the associated MS feature was found to be increased by 2-fold in this study. Neural cell adhesion molecule 1 (NCAM1) serves as a marker for diagnosing lung neuroendocrine tumors. FIBA peptides were identified by MS analysis with increased levels correlating with advancing progression of lung cancer. Of special note are the two unknown features, Group2 and Group7, which show differences between control and diseased subjects. Group2 was found in 54 out of 56 subjects and had a modest 33% decrease in diseased subjects. In contrast, Group7 was found only in diseased subjects (14 out of 28 members of the class). These results demonstrated the potential utility for the particle corona to aid in identifying known and unknown markers for different disease states.

Example 4: Dynamic Range Compression of Plasma Using Protein Corona Analysis

This example describes dynamic range compression using particles to collect proteins from a plasma sample.

In order to evaluate the ability of particles to compress the measured dynamic range, measured and identified protein feature intensities were compared to the published values for the concentration of the same protein. First, the resulting peptide features for each protein was selected with the maximum MS-determined intensity of all possible features for a protein (using the OpenMS MS data processing tools to extract monoisotopic peak values), and then the intensities were modeled against the published abundance levels for those same proteins. FIG. 13 shows correlation of the maximum intensities of particle corona proteins and plasma proteins to the published concentration of the same proteins. The blue plotted lines are linear regression models to the data and the shaded regions represent the standard error of the model fit. The dynamic range of the samples assayed with particles ("S-003," "S-007," and "S-011", detailed in TABLE 1) exhibited a compressed dynamic range as compared to the plasma sample not assayed with particles ("Plasma"), as shown by the decrease in slopes of the linear fits. The slopes of each plot are 0.47, 0.19, 0.22, and 0.18 for, plasma without particles, plasma with S-003 particles, plasma with S-007 particles, and plasma with S-011 particles, respectively. FIG. 14 shows the dynamic range compression of a protein corona analysis assay with mass spectrometry as compared to mass spectrometry without particle corona formation. Protein intensities of common proteins identified in particle coronas in the plasma samples assayed in FIG. 13 ("Nanoparticle MS In Intensity") are plotted against the protein intensity identified by mass spectrometry of plasma without particles ("Plasma MS In Intensity"). The lightest dotted line shows a slope of 1, indicating the dynamic range of mass spectrometry without particles. The slopes of the linear fits to the protein intensity was 0.12, 0.36, and 0.093 for S-003, S-007, and S-011 particles, respectively. The grayed area indicates the standard error region of the regression fit.

By comparing the regression model slopes and the intensity span of the measured data, the biomolecule coronas contain more proteins at lower abundances (measured or reported) than does plasma. The dynamic range of those measured values was compressed (the slope of the regression model is reduced) for particle measurements as compared to plasma measurements. This was consistent with previous observations that particle can effectively compress the measured dynamic range for abundances in the resulting corona as compared to the original dynamic range in plasma, which could be attributable to the combination of absolute concentration of a protein, its binding affinity to particles, and its interactions with neighboring proteins. The results indicated that the biomolecule corona strategy facilitated the identification of a broad spectrum of plasma proteins, particularly those in the low abundance that are challenging for rapid detection by conventional proteomic techniques.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An automated system for preparing a biological sample for mass spectrometry analysis using a plurality of magnetic particles comprising at least one physicochemical property, the system comprising:
   (a) a fluid transfer unit comprising a multichannel fluid transfer instrument for transferring fluid between units within the system;
   (b) a sample storage unit comprising a support for storing at least one biological sample;
   (c) a sensing unit comprising a magnetic sensor array, wherein the magnetic sensor array comprises at least two partitions that comprise the plurality of magnetic particles, wherein the plurality of magnetic particles comprises physicochemical properties configured to bind a population of proteins comprising at least 300 protein groups within a biological sample, wherein the plurality of magnetic particles comprises a polydispersity index of at least 0.5, and wherein the support is configured to immobilize the plurality of magnetic particles when the magnetic sensor array is transferred to the support;
   (d) a reagent storage unit comprising supports for storing a plurality of reagents;
   (e) a waste unit comprising supports for storing a reagent to be disposed of;
   (f) a magnetized support comprising a magnetic source; and
   (g) a control unit comprising one or more processors programmed to perform steps comprising:
      i. incubating the biological sample with the plurality of magnetic particles of the magnetic sensor array under conditions sufficient to bind the population of proteins comprising at least 300 protein groups;
      ii. applying the magnetized support to the magnetic sensor array to separate unbound sample from the plurality of magnetic particles;
      iii. separating unbound components within the partition from the population of proteins and the plurality of magnetic particles; and
      iv. preparing the population of proteins for mass spectrometry, wherein the preparing comprises incubating a digestion solution with the population of proteins and the plurality of magnetic particles.

2. The automated system of claim 1, wherein the automated system further comprises a thermal unit capable of maintaining a temperature while incubating the biological sample with the plurality of magnetic particles of the magnetic sensor array.

3. The automated system of claim 1, wherein the automated system further comprises a rotational unit capable of physically agitating or mixing a sample.

4. The automated system of claim 1, wherein the (i) incubating the biological sample with the plurality of magnetic particles of the magnetic sensor array comprises incubating about 10 microliters to about 100 microliters of the biological sample with the plurality of magnetic particles.

5. The automated system of claim 4, wherein the (i) incubating the biological sample with the plurality of magnetic particles of the magnetic sensor array comprises incubating about 1 mg/mL to about 3 mg/mL of the plurality of magnetic particles.

6. The automated system of claim 1, wherein the biological sample comprises plasma or serum.

7. The automated system of claim 1, wherein the (i) incubating the biological sample with the plurality of magnetic particles of the magnetic sensor array comprises an incubation time of at least 25 minutes.

8. The automated system of claim 7, wherein the (i) incubating the biological sample with the plurality of magnetic particles of the magnetic sensor array comprises an incubation above room temperature.

9. The automated system of claim 1, wherein the control unit comprising one or more processors is further programmed to perform a series of wash steps before (iv) preparing the population of proteins for mass spectrometry.

10. The automated system of claim 1, wherein the (i) incubating the biological sample with the plurality of magnetic particles of the magnetic sensor array comprises incubating the biological sample with the plurality of magnetic particles and a diluent, wherein the diluent comprises a buffer, and wherein the biological sample is diluted at least 3-fold with the diluent.

11. The automated system of claim 1, wherein the automated system generates the prepared population of proteins in less than 7 hours.

12. The automated system of claim 1, wherein the plurality of magnetic particles comprises a silica surface.

13. The automated system of claim 1, wherein the plurality of magnetic particles comprises a superparamagnetic iron oxide nanoparticle.

14. The automated system of claim 1, wherein the plurality of magnetic particles comprises a negative surface charge.

15. An automated system for preparing a biological sample for mass spectrometry analysis using a plurality of magnetic particles comprising at least one physicochemical property, the system comprising:
   (a) a fluid transfer unit comprising a multichannel fluid transfer instrument for transferring fluid between units within the system;
   (b) a sample storage unit comprising a support for storing at least one biological sample;
   (c) a sensing unit comprising a magnetic sensor array, wherein the magnetic sensor array comprises at least two partitions that comprise the plurality of magnetic particles wherein the plurality of magnetic particles comprises physicochemical properties configured to bind a population of proteins comprising at least 300 protein groups within a biological sample, wherein the plurality of magnetic particles comprises a poly(N-(3-(dimethylamino)propyl) methacrylamide) coating, and wherein the support is configured to immobilize the plurality of magnetic particles when the magnetic sensor array is transferred to the support;
   (d) a reagent storage unit comprising supports for storing a plurality of reagents;
   (e) a waste unit comprising supports for storing a reagent to be disposed of;
   (f) a magnetized support comprising a magnetic source; and
   (g) a control unit comprising one or more processors programmed to perform steps comprising:
      i. incubating the biological sample with the plurality of magnetic particles of the magnetic sensor array under conditions sufficient to bind the population of proteins comprising at least 300 protein groups;

ii. applying the magnetized support to the magnetic sensor array to separate unbound sample from the plurality of magnetic particles:

iii. separating unbound components within the at least two partitions from the population of proteins and the plurality of magnetic particles; and iv. preparing the population of proteins for mass spectrometry, wherein the preparing comprises incubating a digestion solution with the population of proteins and the plurality of magnetic particles.

16. An automated system for preparing a biological sample for mass spectrometry analysis using a plurality of magnetic particles comprising at least one physicochemical property, the system comprising:

(a) a fluid transfer unit comprising a multichannel fluid transfer instrument for transferring fluid between units within the system;

(b) a sample storage unit comprising a support for storing at least one biological sample;

(c) a sensing unit comprising a magnetic sensor array, wherein the magnetic sensor array comprises at least two partitions that comprise the plurality of magnetic particles wherein the plurality of magnetic particles comprises physicochemical properties configured to bind a population of proteins comprising at least 300 protein groups within a biological sample, wherein the plurality of magnetic particles comprises a polydispersity index of 0.01 to 0.1, and wherein the support is configured to immobilize the plurality of magnetic particles when the magnetic sensor array is transferred to the support;

(d) a reagent storage unit comprising supports for storing a plurality of reagents;

(e) a waste unit comprising supports for storing a reagent to be disposed of:

(f) a magnetized support comprising a magnetic source; and (g) a control unit comprising one or more processors programmed to perform steps comprising:

i. incubating the biological sample with the plurality of magnetic particles of the magnetic sensor array under conditions sufficient to bind the population of proteins comprising at least 300 protein groups;

ii. applying the magnetized support to the magnetic sensor array to separate unbound sample from the plurality of magnetic particles:

iii. separating unbound components within the at least two partitions from the population of proteins and the plurality of magnetic particles; and iv. preparing the population of proteins for mass spectrometry, wherein the preparing comprises incubating a digestion solution with the population of proteins and the plurality of magnetic particles.

17. The automated system of claim 1, wherein the plurality of magnetic particles is configured to bind the population of proteins that comprise from 300 to 2200 protein groups within the biological sample.

18. The automated system of claim 15, wherein the (i) incubating the biological sample with the plurality of magnetic particles of the magnetic sensor array comprises incubating about 10 microliters to about 100 microliters of the biological sample with the plurality of magnetic particles.

19. The automated system of claim 18, wherein the (i) incubating the biological sample with the plurality of magnetic particles of the magnetic sensor array comprises incubating about 1 mg/mL to about 3 mg/mL of the plurality of magnetic particles.

20. The automated system of claim 15, wherein the biological sample comprises plasma or serum.

21. The automated system of claim 15, wherein the plurality of magnetic particles comprises a superparamagnetic iron oxide nanoparticle.

22. The automated system of claim 15, wherein the (i) incubating the biological sample with the plurality of magnetic particles of the magnetic sensor array comprises an incubation above room temperature.

23. The automated system of claim 15, wherein the control unit comprising one or more processors is further programmed to perform a series of wash steps before (iv) preparing the population of proteins for mass spectrometry.

24. The automated system of claim 15, wherein the plurality of magnetic particles is configured to bind the population of proteins that comprise from 300 to 2200 protein groups within the biological sample.

25. The automated system of claim 15, wherein the automated system further comprises a thermal unit capable of maintaining a temperature while incubating the biological sample with the magnetic particles of the magnetic sensor array.

26. The automated system of claim 15, wherein the automated system further comprises a rotational unit capable of physically agitating or mixing a sample.

27. The automated system of claim 1, wherein the plurality of magnetic particles comprise microparticles.

28. The automated system of claim 10, wherein the buffer comprises tris(hydroxymethyl)aminomethane (TRIS).

29. The automated system of claim 10, wherein the biological sample is plasma or serum, and wherein the plurality of magnetic particles comprise microparticles with a negative surface charge.

30. The automated system of claim 15, wherein the preparing the population of proteins for mass spectrometry comprises purifying the digested proteins using solid-phase extraction.

* * * * *